US012600751B2

(12) United States Patent (10) Patent No.: US 12,600,751 B2
Kraemer-Kuehl et al. (45) Date of Patent: Apr. 14, 2026

(54) MODIFIED S2 SUBUNIT OF THE CORONAVIRUS SPIKE PROTEIN

(71) Applicant: Boehringer Ingelheim Vetmedica GMBH, Ingelheim am Rhein (DE)

(72) Inventors: Annika Kraemer-Kuehl, Seesen (DE); Thomas Min Stephan, Hannover (DE)

( * ) Notice: Subject to any disclaimer, the term of this patent is extended or adjusted under 35 U.S.C. 154(b) by 991 days.

(21) Appl. No.: 17/595,124

(22) PCT Filed: May 6, 2020

(86) PCT No.: PCT/EP2020/062528
§ 371 (c)(1),
(2) Date: Nov. 9, 2021

(87) PCT Pub. No.: WO2020/229249
PCT Pub. Date: Nov. 19, 2020

(65) Prior Publication Data
US 2022/0213148 A1 Jul. 7, 2022

(30) Foreign Application Priority Data

May 10, 2019 (EP) ..................................... 19173823

(51) Int. Cl.
*C07K 14/005* (2006.01)
*A61K 39/00* (2006.01)

(52) U.S. Cl.
CPC ............ *C07K 14/005* (2013.01); *A61K 39/00* (2013.01); *A61K 2039/5258* (2013.01)

(58) Field of Classification Search
CPC .................. C07K 14/005; A61K 39/00; A61K 2039/5258; A61K 2039/5254; A61K 39/12; C12N 2770/20052; C12N 7/00; C12N 2770/20021; C12N 2770/20022; C12N 2770/20034
See application file for complete search history.

(56) References Cited

U.S. PATENT DOCUMENTS

| | | | |
|---|---|---|---|
| 2,909,462 A | 10/1959 | Warfield | |
| 5,750,113 A | 5/1998 | Cook | |
| 8,828,407 B2 | 9/2014 | Britton et al. | |
| 9,296,991 B2 | 3/2016 | Geerligs et al. | |
| 10,772,953 B2 | 9/2020 | van Santen et al. | |
| 11,065,328 B2 | 7/2021 | Rottier et al. | |
| 11,224,649 B2 | 1/2022 | Kraemer-Kuehl et al. | |
| 11,512,115 B2 | 11/2022 | Kraemer-Kuehl et al. | |
| 11,696,947 B2 | 7/2023 | Kraemer-Kuehl et al. | |
| 11,744,888 B2 | 9/2023 | Kraemer-Kuehl et al. | |
| 11,999,766 B2 | 6/2024 | Kraemer-Kuehl et al. | |
| 2006/0257852 A1 | 11/2006 | Rappuoli et al. | |
| 2007/0154489 A1 | 7/2007 | Cavanagh et al. | |
| 2011/0097353 A1 | 4/2011 | Sellers et al. | |
| 2012/0177675 A1 | 7/2012 | Britton et al. | |
| 2014/0141043 A1 | 5/2014 | Toro Guzman et al. | |
| 2016/0030550 A1 | 2/2016 | Toro Guzman et al. | |
| 2016/0032253 A1 | 2/2016 | Sellers | |
| 2016/0060303 A1* | 3/2016 | Britton ................. C07K 14/005 | |
| | | | 435/364 |
| 2016/0106828 A1 | 4/2016 | Toro | |
| 2017/0096455 A1 | 4/2017 | Baric et al. | |
| 2018/0216082 A1 | 8/2018 | Jordan et al. | |
| 2019/0046634 A1 | 2/2019 | van Santen et al. | |
| 2022/0202931 A1 | 6/2022 | Mundt et al. | |
| 2023/0158138 A1 | 5/2023 | Talaat et al. | |
| 2025/0064920 A1 | 2/2025 | Albanese et al. | |

FOREIGN PATENT DOCUMENTS

| | | |
|---|---|---|
| CN | 101948812 A | 1/2011 |
| CN | 102574897 A | 7/2012 |
| CN | 103642759 A | 3/2014 |
| CN | 104353070 A | 2/2015 |
| CN | 104694488 A | 6/2015 |
| CN | 108300704 A | 7/2018 |
| CO | 2019000214 A2 | 1/2019 |
| CO | 2021005066 A2 | 4/2021 |
| CO | 2021005069 A2 | 4/2021 |
| WO | 1986005806 A1 | 10/1986 |
| WO | 2001000234 A2 | 1/2001 |
| WO | 2001009290 A2 | 2/2001 |
| WO | 01/64244 A2 | 9/2001 |
| WO | 2004078203 A2 | 9/2004 |
| WO | 2004092360 A2 | 10/2004 |
| WO | 11/004146 A1 | 1/2011 |
| WO | 2011004146 A1 | 1/2011 |
| WO | 2014177873 A1 | 11/2014 |
| WO | 2016012793 A1 | 1/2016 |
| WO | 2019046634 A1 | 3/2019 |
| WO | 2020089164 A1 | 5/2020 |

(Continued)

OTHER PUBLICATIONS

Bickerton, Erica, Giulia Dowgier, and Paul Britton. "Recombinant infectious bronchitis viruses expressing heterologous S1 subunits: potential for a new generation of vaccines that replicate in Vero cells." Journal of General Virology 99.12 (2018): 1681-1685.
Bickerton et al. 2018 The S2 Subunit of Infectious Bronchitis Virus Beaudette is a Determinant of Cellular Tropism 2018 J Virology 92:1-18.
Bijlenga et al. Development and use of the H strain of avian Infectious bronchitis virus from the Netherlands as a vaccine: a review 2004. Avian Pathol. 33:550-557.
Casais et al. Recombinant Avian Infectious Bronchitis Virus Expressing a Heterologous Spike Gene Demonstrates that the Spike Protein Is a Determinant of Cell Tropism 2003. J. Virol. 77; 9084-9089.
Cavanagh Coronavirus avian infectious bronchitis virus 2007. Vet. Res. 38:281-297.
Cook et al. The long view: 40 years of infectious bronchitis research 2012. Avian Pathol. 41:239-250.

(Continued)

*Primary Examiner* — Rachel B Gill
(74) *Attorney, Agent, or Firm* — Shanyun Lu

(57) ABSTRACT

A recombinant avian coronavirus spike protein or fragment thereof includes a mutation at amino acid position 865. An immunogenic composition includes an avian coronavirus with such spike protein.

22 Claims, 2 Drawing Sheets

Specification includes a Sequence Listing.

(56)                    References Cited

FOREIGN PATENT DOCUMENTS

| WO | 2020089166 A1 | 5/2020 |
| WO | 2020229248 A1 | 11/2020 |
| WO | 2020229249 A1 | 11/2020 |
| WO | 2020229257 A1 | 11/2020 |
| WO | 2022066683 A1 | 3/2022 |
| WO | 2025027551 A2 | 2/2025 |

OTHER PUBLICATIONS

Dolz et al. Antigenic and molecular characterization of isolates of the Italy 02 infectious bronchitis virus genotype 2006. Avian Pathology 35(2), 77-85.

Ellis et al. Recombinant Infectious Bronchitis Viruses Expressing Chimeric Spike Glycoproteins Induce Partial Protective Immunity against Homologous Challenge despite Limited Replication In Vivo 2018. J. Virol. 92(23):1-18.

Fang et al. Selection of and recombination between minor variants lead to the adaptation of an avian coronavirus to primate cells 2005. Biochemical and Biophysical Research Communication 336:417 to 423.

Farsang et al. Molecular epizootiology of infectious bronchitis virus in Sweden indicating the involvement of a vaccine strain 2002. Avian Pathology 31:229-236.

Feng et al. Analysis of S1 gene of avian infectious bronchitis virus isolated in southern China during 2011-2012. 2014 Virus Genes 49:292-303.

Hodgson et al. Recombinant Infectious Bronchitis Coronavirus Beaudette with the Spike Protein Gene of the Pathogenic M41 Strain Remains Attenuated but Induces Protective Immunity 2004. J Virol 78:13804-13811.

Kuo et al. Retargeting of Coronavirus by Substitution of the Spike Glycoprotein Ectodomain: Crossing the Host Cell Species Barrier 2000. J. Virol. 74:1393-1406.

Liu et al. Complete genome sequence analysis of a predominant infectious bronchitis virus (IBV) strain in China. 2009 Virus Genes 38:56-65.

Promkuntod et al. Mapping of the receptor-binding domain and amino acids critical for attachment in the spike protein of avian coronavirus infectious bronchitis virus 2014. Virology. 448:26-32.

Rauw et al. The positive adjuvant effect of chitosan on antigen-specific cell-mediated immunity after chickens vaccination with live Newcastle disease vaccine 2009. Vet Immunol Immunop 134:249-258.

Todd et al. Development of an adjuvant-active nonionic block copolymer for use in oil-free subunit vaccines formulations 1997. Vaccine 15:564-570.

Valastro et al. S1 gene-based phylogeny of infectious bronchitis virus: An attempt to harmonize virus classification. 2016. Infection, Genetics and Evolution 39:349-364.

Quatros Das Infektiose Bronchitis Virus (IBV): Molekularbiologische Untersuchungen zur Diagnostik und zum Vorkommen sowie zur Pathogenität des Genotyps IBV QX in spezifisch pathogenfreien (SPF) Broilern. 2011 Dissertation. Journal-Nr: 3518.

Wang et al. Intranasal immunization with live attenuated influenza vaccine plus chitosan as an adjuvant protects mice against homologous and heterologous virus challenge 2012. Arch Virol 157:1451-1461.

Worthington et al. A reverse transcriptase-polymerase chain reaction survey of infectious bronchitis virus genotypes in Western Europe from 2002 to 2006. 2008 Avian Pathology 37(3):247-257.

Shang, J. et al., Cryo-EM structure of infectious bronchitis coronavirus spike protein reveals structural and functional evolution of coronavirus spike proteins, PLoS Pathog, 2018, 14(4):e1007009. PDB ID 6CV0, Database: Protein Data Bank (PDB), https://doi.org/10.2210/pdb6CV0/pdb.

Niesters, H.G.M. et al., The peplomer protein sequence of the M41 strain of coronavirus IBV and its comparison with Beaudette strains, Virus Research, 5, 1986, 253-63, Sequence ID: P12651, Database: Uniprot, https://www.uniprot.org/uniprotkb/P12651/entry.

Rutten, L. et al. Impact of SARS-CoV-2 spike stability and RBD exposure on antigenicity and immunogenicity, Scientific Rep, 2024, 14, 5735.

Armesto, Maria, et al. "A recombinant avian infectious bronchitis virus expressing a heterologous spike gene belonging to the 4/91 serotype." PLoS One 6(8), 2011: e24352.

Abbas, Ghulam, et al. "Molecular characterization of infectious bronchitis virus strain HH06 isolated in a poultry farm in North-eastern China." Frontiers in Veterinary Science, 8, 2021: 794228.

Abstract in English for CN101948812A, 2011.

Abstract in English for CN103642759A, 2014.

Abstract in English for CN104694488A, 2015.

Abstract in English for CN108300704A, 2018.

Abstract in English for CO2019000214A2, 2019.

Abstract in English for CO2021005066A2, 2021.

Abstract in English for CO2021005069A2, 2021.

Abstract in English for WO01009290A2, 2001.

Ali, Ahmed, et al. "Safety and efficacy of attenuated classic and variant 2 infectious bronchitis virus candidate vaccines." Poultry science, 97(12), 2018: 4238-4244.

Britton, Paul, et al. "Generation of a recombinant avian coronavirus infectious bronchitis virus using transient dominant selection." J. Virol Methods 123(2), 2005: 203-11.

Britton, Paul, et al. "Modification of the avian coronavirus infectious bronchitis virus for vaccine development." Bioengineered Bugs, 3(2), 2012: 114-119.

Callison A, Scott et al. "Development and evaluation of a real-lime Taqman RT-PCR assay for the detection of infectious bronchitis virus from infected chickens." Journal of Virological Methods, 138, 2006:60-65.

Cavanagh, David et al. "Variation in the spike protein of the 793/B type of infectious bronchitis virus, in the field and during alternate passage in chickens and embryonated eggs." Avian Pathology, 34(1), 2005: 20-25.

Cevac: "Cevac Ibron", Jan. 1, 2017 (Jan. 1, 2017), XP093125209.

Chen, HY et al. "Infection of HeLa cells by avian infectious bronchitis virus is dependent on cell status." Avian Pathology, 36(4), 2007: 269-274.

Communication/Extended Search Report, PCT/EP2020/062526, Oct. 4, 2019.

Dancey, G F et al. "Effect of liposomal model membrane composition on immunogenicity." J Immunol., 120, 1978: 1109-13.

Franzo, Giovanni et al. "Molecular investigation of a full-length genome of a Q1-like IBV strain isolated in Italy in 2013." Virus Res., 2(2), 2015: 77-80.

Geerligs, Harm et al. "Efficacy and safety of an attenuated live QX-like infectious bronchitis virus strain as a vaccine for chickens." Avian Pathology, 40(1), 2011: 93-102.

Geilhausen, H E et al. The pathogenesis of virulent and avirulent avian infectious bronchitis virus. Archiv fur die gesamte Virusforschung, 40, 1973: 285-290.

GenBank: AKV60429.1. "Spike protein [Infectious bronchitis virus]." Dated Aug. 16, 2015.

GenBank: ATE90980.1. "Spike protein {Avian Coronavirus)." Dated Oct. 2, 2017.

GenBank: CAZ866699. 1. "Spike protein {Infectious bronchitis virus ITA/90254/2005)." Dated Oct. 23, 2009.

Goraichuk, I. V. et al. "First complete genome sequence of currently circulating infectious bronchitis virus strain DMV/1639 of the GI-17 lineage." Microbiology Resource Announcements, 8(34), 2019: doi: 10-1128.

Handberg, K J et al. ,,Detection and strain differentiation of infectious bronchitis virus in tracheal tissues from experimentally infected chickens by reverse transcription-polymerase chain reaction. Comparison with an immunohistochemical technique. Avian Pathology, 28, 1999: 327-335.

Hulswit, R. J. G. et al. "Coronavirus spike protein and tropism changes." Advances in Virus Research, 96, 2016: 29-57.

International Search Report and Written Opinion for PCT/EP2019/079389 (WO2020089164) mailed Feb. 6, 2020.

(56)          References Cited

OTHER PUBLICATIONS

International Search Report and Written Opinion for PCT/EP2019/079393 (WO2020/089166) mailed Feb. 18, 2019.

International Search Report and Written Opinion, PCT/EP2020/062526 (WO2020229248A1), Jun. 24, 2020.

International Search Report for PCT/IB2024/057434 (WO2025027551A2), mailed mailed on Apr. 25, 2025.

Jackwood, Mark W. et al. "Molecular evolution of infectious bronchitis virus and the emergence of variant viruses circulating in the United States." Avian Diseases, 65(4), 2021: 631-636.

Kalokhoran, Ali Yousefzadeh, et al. "Co-circulation of three clusters of 793/B-like avian infectious bronchitis virus genotypes in Iranian chicken flocks." Archives of virology, 162, 2017: 3183-3189.

Khanh, NP et al. "Molecular characterization of QX-like and variant infectious bronchitis virus strains in Malaysia based in partial genomic sequences comprising the S-3a/3b-E-M-intergenic region-5a/5b-N gene order." Avian Dis., 61(4), 2017: 442-452.

Li, Hua et al. "Sequence analysis of nephropathogenic infectious bronchitis virus strains of the Massachusetts genotype in Beijing." Avian Pathology, 30(5), 2001: 535-541.

Macdonald, J W et al. "An inverse age resistance of chicken kidneys to infectious bronchitis virus." Avian Pathology, 9, 1980: 245-259.

Merck Animal Health. "Utility and performance of Mildvac-Ma5 for IBV vaccination of broilers with DMV/1639 field challenge." 2022, US-MVC-220100001.

Moore, Kristi M., et al. "Sequence comparison of avian infectious bronchitis virus S1 glycoproteins of the Florida serotype and five variant isolates from Georgia and California." Virus Genes, 17, 1998: 63-83.

Rohaim, Mohammed A. et al. "Evolutionary analysis of infectious bronchitis virus reveals marked genetic diversity and recombination events." Genes, 11(6), 2020: 605.

Shan, Dan, et al. "Effects of hypervariable regions in spike protein on pathogenicity, tropism, and serotypes of infectious bronchitis virus." Virus research, 250, 2018: 104-113.

Shimazaki et al. "Isolation of 4/91 type of infectious bronchitis virus as a new variant in Japan and efficacy of vaccination against 4/91 type field isolate." Avian Diseases, 52, 2008: 618-622.

Song Chang-Seon, "Characteristics and prevention strategies of domestic avian infectious bronchitis (IB)." Feed Journal, 4(1), 2006: 126-133.

The Free Dictionary [Internet] "heterologous protein". Farlex Partner Medical Dictionary,; Farlex, 2012 [retrieved on Dec. 21, 2022].

Van Beurden et al. "Recombinant live attenuated avian coronavirus vaccines with deletions in the accessory genes 3ab and/or 5ab protect against infectious bronchitis in chickens." Vaccine, 36(8), 2018: 1085-1092.

Van Beurden, Steven J et al. "A reverse genetics system for avian coronavirus infectious bronchitis virus based on targeted RNA recombination." Virology Journal, 14, 2017: 1-13.

Wei, Yan-Quan, et al. "Development and characterization of a recombinant infectious bronchitis virus expressing the ectodomain region of S1 gene of H120 strain." Applied Microbiology and Biotechnology, 98(4), 2014: 1727-1735.

Written Opinion of the International Search Authority PCT/EP2020/062528 (WO2020229249A1), mailed on Jul. 17, 2020.

Written Opinion of the International Search Authority PCT/EP2020/062563 (WO2020229257A1), mailed on Jul. 31, 2020.

Written Opinion of the International Search Authority PCT/IB2024/057434 (WO2025027551A2), mailed on Apr. 25, 2025.

Xu, Peng-wei, et al. "Assembly and immunogenicity of baculovirus-derived infectious bronchitis virus-like particles carrying membrane, envelope and the recombinant spike proteins." Biotechnology letters, 38, 2016: 299-304.

Zhang, Tingting et al. "Serotype shift of a 793/B genotype infectious bronchitis coronavirus by natural recombination." Infect Genet Evol., 32, 2015: 377-387.

Zhou, Ying Shun, et al. "Establishment of reverse genetics system for infectious bronchitis virus attenuated vaccine Strain H120." Veterinary Microbiology, 162(1), 2013: 53-61.

Zhou, Yingshun, et al. "The establishment and characteristics of cell-adapted IBV strain H120." Archives of virology, 161(11), 2016: 3179-3187.

Zwaagstra, K. A. et al. "Rapid detection and identification of avian infectious bronchitis virus." Journal of Clinical Microbiology, 30(1), 1992: 79-84.

* cited by examiner

MODIFIED S2 SUBUNIT OF THE CORONAVIRUS SPIKE PROTEIN

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Avian coronavirus infectious bronchitis virus (IBV) is the prototype gammacoronavirus of the family Coronaviridae, order Nidovirales. Infectious bronchitis virus principally infects the upper respiratory epithelium of chickens, causing a respiratory disease, commonly complicated by secondary bacterial pathogens (Cook et al. 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-thirds of the viral genome comprise a large coding region (also designated as gene 1), divided into two open reading frames 1a and 1b, which encode for at least 15 nonstructural proteins involved in RNA cell tropismon, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms the ribonucleoprotein core along with the viral RNA. The coronavirus spike protein determines the host species tropism (Kuo et al. 2000. J. Virol. 74:1393-1406). It is a dimeric or trimeric transmembrane protein, which is proteolytically cleaved into two subunits, S1 and S2. The glycosylated S1 domain forms the 'head' of the spike protein and contains the receptor binding domain that interacts with 2,3-linked sialic acids on the host cell surface (Promkuntod et al. 2014. Virology. 448:26-32). The S2 domain contains the remaining part of the ectodomain (the 'stalk'), the transmembrane domain and an endodomain located in the cytoplasm.

The to date widely used live-attenuated IBV vaccine strains H52 and H120 were developed in the 1960s in the Netherlands, by serial passaging of a Massachusetts serotype IBV strain in embryonated chicken eggs (Bijlenga et al. 2004; Avian Pathol. 33:550-557). Said vaccine strains also have to be propagated in embroynated chicken eggs for production. Today, IBV vaccines (both inactivated and live vaccines) are still propagated in emryonated chicken eggs which is cumbersome and expensive.

The only cell-line adapted IBV described so far is the IBV strain Beaudette, which efficiently replicates in Vero and BHK cells. Casais et al 2003 (J. Virol. 77; 9084-9089) show that the S protein of Beaudette is the determinant of cell line tropism by generating recombinant IBVs using ectodomain sequences of the Beaudette spike, which were able to transfer the extended cell line tropism to another IBV (M41).

WO 2011/004146 discloses that the S2 subunit from Beaudette is responsible for the extended tissue tropism. A sequence within the S2 subunit, a heparan-sulphate binding site from Beaudette, has been identified to be responsible for the extended cell line tropism. Furthermore, Bickerton et al 2018 (Journal of Virology 92 (19)) disclose a Beaudette specific motif of eight amino acids. However, recombinant IBV's with a Beaudette spike S2 subunit are not suitable as vaccines. Ellis et al 2018 (J. Virol. 92(23)) describe that recombinant Beaudette with chimeric spikes with heterologous 51 subunits from M41 or QX in combination with Beaudette spike S2 subunit do not confer sufficient protection against 51 homologous challenges. Also, Beaudette wild type does not provide procection against homologous challenge like other licensed vaccines belonging to the Massachusetts serotype (Hodgson et al 2004: J Virol 78:13804-13811 or Geilhausen et al 1973: Archiv für die gesamte Virusforschung 40: 285-290).

Fang et al 2005 (Biochemical and Biophysical Research Communication 336; pages 417 to 423) disclose that the adaption of Beaudette for propagation in Vero cells resulted in 49 amino acid modifications, 26 located within the spike protein.

Taken together, providing IBV vaccines having an extended cell or tissue tropism by exchanging the spike protein to a heterologous Beaudette Spike protein would not result in IBV vaccines providing sufficient efficacy and with the Beaudette Spike sequence would be limited to protection against a Massachusetts serotype strain challenge and missing cross protection against further genotypes. Furthermore, the prior art motifs or sites identified in Beaudette have not been transferred into IBV vaccines showing both an extended cell culture or tissue tropism and efficacy in protection (no interference between extended tropism and vaccine efficacy has been shown).

Consequently, there is a need for single amino acids or short motifs that can be transferred into IBVs or IBV vaccines without influencing vaccine efficacy but enabling an extended cell or tissue tropism for production.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an avian coronavirus spike protein or fragment thereof comprising an aromatic amino acid at position 865, wherein the spike protein or fragment thereof is not from IBV strain M41.

Further, the present invention provides an avian coronavirus Spike Protein or fragment thereof, wherein at least a part of the S2 subunit is from an avian coronavirus with a restricted cell or tissue tropism, and wherein the amino acid at position 865 is an aromatic amino acid.

Further, the present invention provides a recombinant avian coronavirus spike protein or fragment thereof comprising a mutation at amino acid position 865.

Generally, the present invention provides an IBV spike protein or fragment thereof comprising an aromatic amino acid at position 865, wherein the spike protein or fragment thereof is not from IBV strain M41.

The present invention also provides an IBV spike protein or fragment thereof, wherein at least a part of the S2 subunit is from an IBV with a restricted cell or tissue tropism, and wherein the amino acid at position 865 is an aromatic amino acid.

Further, the present invention provides a recombinant IBV spike protein or fragment thereof comprising a mutation at amino acid position 865.

Advantageously, the experimental data show that coronavirus strains (strains such as exemplarily H52 and CR88 IBV strains) have an extended cell or tissue tropism after modifying a single position, position 865, into an aromatic amino acid (Histidine) within the spike protein.

The term "coronavirus" is well known to the person skilled in the art. In general coronaviruses are viruses of the subfamily Coronavirinae in the family Coronaviridae, in the order Nidovirales. Coronaviruses are enveloped viruses and have a positive-sense single-stranded RNA genome with a nucleocapsid of helical symmetry. The term "coronavirus" encompasses all strains, genotypes, protectotypes, and serotypes of infectious bronchitis virus. Examples of avian coronaviruses are infectious bronchitis virus (IBV); guinea fowl coronavirus (GfCoV) and turkey coronavirus (TCoV; turkey enteritis virus and bluecomb disease virus).

The term "IBV" refers to infectious bronchitis virus which is well known to the person skilled in the art. The term "IBV" encompasses all strains, genotypes, protectotypes, and serotypes of infectious bronchitis virus.

The term "mutation" comprises modifications in the viral RNA encoding proteins leading to an alteration of said encoded protein. Further, the term "mutation" comprises genetically engineered mutations. The term mutation relates to, but is not limited to, substitutions (replacement of one or several nucleotides/base pairs), deletions (removal of one, several or all nucleotides/base pairs), and/or insertions (addition of one or several nucleotides/base pairs). As used herein, a mutation may be a single mutation or several mutations, therefore, often the term "mutation(s)" used and relates to both a single mutation and several mutations. However, the term mutation is well known to the person skilled in the art and the person skilled in the art can generate mutations without further ado.

The term "spike" refers to a specific protein of the avian coronavirus or IBV that is well known by the person skilled in the art. The spike protein is the major inducer of antibodies and a protective immune response. Further, the spike (S) protein facilitates cell entry of the avian coronavirus or IBV by binding cellular receptors on the host cell and also by mediating virus-cell membrane fusion with the host cell membranes. In addition, it determines the cell and tissue tropism of the virus strain.

The terms "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

Mutation 865

In one aspect of the avian coronavirus or IBV spike protein or fragment thereof according to the present invention the aromatic amino acid at amino acid position 865 is introduced by a mutation. The wording "introduced" means that the mutation has been introduced by genetic engineering (artificially, e.g., by human intervention).

In another specific aspect of the avian coronavirus or IBV spike protein or fragment thereof according to the present invention the mutation is an amino acid substitution, deletion or insertion.

In another specific aspect of the avian coronavirus or IBV spike protein or fragment thereof according to the present invention the amino acid at amino acid position 865 is mutated to an aromatic amino acid; or a polar amino acid at amino acid position 865 is mutated to an aromatic amino acid; or a glutamine at amino acid position 865 is mutated into a histidine.

In another specific aspect of the avian coronavirus or IBV spike protein or fragment thereof according to the present invention the aromatic amino acid at amino acid position 865 is a histidine.

Extended Cell or Tissue Tropism

In another specific aspect of the avian coronavirus or IBV spike protein or fragment thereof according to the present invention the aromatic amino acid at amino acid position 865 or said mutation at amino acid position 865 leads to an extended cell or tissue tropism of the avian coronavirus or IBV.

The term "cell or tissue" is known by the person skilled in the art. The term cell encompasses cell lines such as the cell lines listed elsewhere herein as well as primary cells. The term tissue encompasses cells from tissues such as the ones listed elsewhere herein, exemplarily such as primary chicken embryo cells from lung or liver or primary chicken fibroblasts. The term encompasses the propagation of cells or tissue (cells) in culture outside the organism. The term "culture" relates to the propagation of cells (such as cell line cells or primary cells or tissue cells) outside an organism under defined culture conditions known by the person skilled in the art.

The term "extended tropism" means that the avian coronavirus or IBV of the invention can be propagated in cells (such as cell lines) or tissue cells (in addition to primary chicken embryo cells from kidney). In contrast, coronavirus vaccines (such as IBV vaccines) or non-cell culture adapted wildtype coronaviruses or IBVs (cell line adapted IBV Beaudette strains are described) can only be propagated in embryonated chicken eggs or primary chicken embryo cells from kidney (after adaption). Accordingly, a coronavirus (such as IBV) of the invention with extended cell or tissue tropism has the capacity to infect and/or replicate in one or more cell lines or tissue cells other than primary chicken embryo cells from kidney. Preferably, the coronavirus (such as IBV) of the invention with extended cell or tissue tropism has the capacity to infect and/or replicate in one or more cell lines as listed herein. Accordingly, a coronavirus or IBV with extended cell or tissue tropism may, for example, have the capacity to infect and/or replicate in BHK or EB66 cells.

The term "restricted tropism" means that the avian coronavirus or IBV can be propagated if at all only in primary chicken embryo cells from kidney. Accordingly, a coronavirus or IBV with restricted cell or tissue tropism does not have the capacity to infect and/or replicate in e.g. BHK or EB66 cells.

Advantageously, the experimental data show that IBV strains such as exemplarily H52 and CR88 have an extended cell or tissue tropism after modifying the single amino acid position 865 within the spike protein into an aromatic amino acid. Further, it has been shown that the modification to a Histidine at Position 865 is genetically stable.

In another specific aspect of the avian coronavirus or IBV spike protein or fragment thereof according to the present invention the avian coronavirus or IBV is infecting and/or replicating in at least one cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

In another specific aspect of the avian coronavirus or IBV spike protein or fragment thereof according to the present invention the avian coronavirus or IBV is infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+ (Spodoptera frugiperda).

In another specific aspect of the avian coronavirus or IBV spike protein or fragment thereof according to the present invention the avian coronavirus or IBV is infecting and/or replicating in at least one cell line selected from the list consisting of: DF-1, EB66, PBS-12, PBS-12SF, BHK, HEK 293T, Vero, MA104 and RK13.

Preferably, the IBV is infecting and/or replicating in EB66 or BHK cell line.

All mentioned cell lines are well known to the person skilled in the art and are commercially and/or publicly available. MDCK cells are exemplarily deposited at the American Tissue Culture Collection under accession number ATCC CCL-34 or ATCC CRL-2285. DF-1 cells are exemplarily deposited at the American Tissue Culture Collection under accession number ATCC CRL-12203). PBS-12SF cells are exemplarily deposited at the American Tissue Culture Collection under accession number ATCC PTA-8565 or deposited at RRID under CVCL 1K17. BHK-21 cells are exemplarily deposited at the American Tissue Culture Collection under accession number ATCC CCL-10. HEK 293T cells are exemplarily deposited at the American Tissue Culture Collection under accession number ATCC CRL-3216. Vero cells are exemplarily deposited at the American Tissue Culture Collection under accession number ATCC CCL-81. MA104 and cells are exemplarily deposited at the American Tissue Culture Collection under accession number ATCC CRL-2378. RK13 cells are exemplarily deposited at the American Tissue Culture Collection under accession number ATCC CCL-37.

Numbering of Amino Acid Position 865

In another specific aspect of the avian coronavirus or IBV spike protein or fragment thereof according to the present invention the numbering of amino acid position 865 refers to the amino acid position 865 in the spike protein of an IBV H52, an IBV H120 or an M41.

In another specific aspect of the avian coronavirus or IBV spike protein or fragment thereof according to the present invention the numbering of amino acid position 865 refers to the amino acid position 865 in the spike protein of an IBV H52.

In another specific aspect of the avian coronavirus or IBV spike protein or fragment thereof according to the present invention the numbering of amino acid position 865 refers to the amino acid position 865 in the spike protein as exemplarily given in SEQ ID NO:1.

In another specific aspect of the avian coronavirus or IBV spike protein or fragment thereof according to the present invention the amino acid sequence of SEQ ID NO:1 is used for determining the position numbering in the spike protein.

In another specific aspect of the avian coronavirus or IBV spike protein or fragment thereof according to the present invention for determining the amino position 865 in a spike protein the amino acid sequence is aligned to the amino acid sequence of SEQ ID NO:1.

In another specific aspect of the avian coronavirus or IBV spike protein or fragment thereof according to the present invention the amino acid position 865 is within the S2 subunit of the spike protein.

In another specific aspect of the avian coronavirus or IBV spike protein or fragment thereof according to the present invention the amino acid position 865 corresponds to amino acid position 867 of the spike protein sequence of IBV CR88.

In another specific aspect of the avian coronavirus or IBV spike protein or fragment thereof according to the present invention the amino acid position 865 corresponds to amino acid position 868 of the spike protein sequence of IBV QX.

In another specific aspect of the avian coronavirus or IBV spike protein or fragment thereof according to the present invention the amino acid position 865 corresponds to amino acid position 869 of the spike protein sequence of IBV Q1.

In another specific aspect of the avian coronavirus or IBV spike protein or fragment thereof according to the present invention the amino acid position 865 corresponds to amino acid position 868 of the spike protein sequence of IBV Var2.

In another specific aspect of the avian coronavirus or IBV spike protein or fragment thereof according to the present invention the amino acid position 865 corresponds to amino acid position 872 of the spike protein sequence of IBV Brazil.

In another specific aspect of the avian coronavirus or IBV spike protein or fragment thereof according to the present invention the amino acid position 865 corresponds to amino acid position 871 of the spike protein sequence of IBV Ark99.

In another specific aspect of the avian coronavirus or IBV spike protein or fragment thereof according to the present invention the spike protein has one or more of the following amino acids selected from the group consisting of:

862 is an alanine, and/or 864 is an alanine, and/or 866 is a valine, and/or 867 is an aspartate, and/or 868 is an arginine.

The numbering of said amino acid positions refer to the amino acid positions within the spike protein as exemplarily given in SEQ ID NO:1.

Spike

The present invention also provides a spike protein or fragment thereof as described above, wherein the spike protein or fragment thereof is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine haemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV). Thus, the present invention also provides a coronavirus spike protein or fragment thereof, wherein at least a part of the S2 subunit is from a coronavirus with a restricted cell or tissue tropism, and wherein the amino acid position 865 is an aromatic amino acid and wherein the spike protein is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine haemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV). Further, the present invention also provides a recombinant coronavirus spike protein or fragment thereof comprising a mutation at amino acid position 865, wherein the spike protein is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine haemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV).

In another specific aspect of the avian coronavirus spike protein or fragment thereof according to the present invention the avian coronavirus spike protein or fragment thereof is selected from the group consisting of: infectious bronchitis virus (IBV); guinea fowl coronavirus (GfCoV) and turkey coronavirus (TCoV; turkey enteritis virus and bluecomb disease virus).

In another specific aspect of the avian coronavirus spike protein or fragment thereof according to the present invention the avian coronavirus is IBV (infectious bronchitis virus).

IBV strains can be classified by serotype and genotype. Serotype classification involves treatment of the virus with neutralizing antibodies, whereas genotype classification generally involves examining the sequence of the S1 (spike) protein. However, the different IBV strains are well known to the person skilled in the art. Infectious bronchitis virus was first discovered in the United States in the 1930s.

The first IBV serotype identified was Massachusetts and remained the only serotype until the discovery of a different IBV serotype in 1956. Nowadays, several additional serotypes, including Arkansas and Delaware have been identified in the United States of America in addition to the originally identified Massachusetts type. Today, IBV Mass viruses can be identified in many countries of the world.

The IBV strain Beaudette is of Massachusetts serotype and was derived following at least 150 passages in chicken embryos. The IBV strain Beaudette was originally isolated by Beaudette and Hudson (J. Am. Vet. Med. A. 90, 51-60, 1937) and passaged in chicken embryos. Other Massachusetts serotype IBV strains besides Beaudette are H120, H52, and M41. The H120 strain was passaged 120 times in embryonated chickens eggs.

IBV QX is described as virulent field isolate of IBV which was originally isolated in China. However, the virus has spread towards Europe and has been identified in parts of Western Europe, predominantly in the Netherlands, but also in Germany, France, Belgium, Denmark and in the UK. In addition, the QX genotype or serotype has been described in several countries in Asia and Africa.

The strains designated "Italien-02" or "Italy-02" was isolated in the late 1990's in Italy. The sequence analysis of one of these isolates was published in 2002 (NCBI-BLAST, number AJ457137). However, studies have shown that this Italian-02 strain is widespread in Europe and that, apart from IBV variant strain 4/91 it has become one of the most predominant genotypes in the UK, Spain, France and The Netherlands.

Since 1996 a new Infectious Bronchitis virus (IBV) genotype, referred to as Q1, has circulated in China and was reported for the first time in Italy in 2011. Q1 is associated with an increase of mortality, kidney lesions and proventriculitis.

Furthermore, strains D274, B1648/D8880, D1466, V1397 and Arkansas have been identified in Europe as well.

It is in the general knowledge of a person skilled in the art where to obtain any IBV strains. IBV strains can be be commercially purchased, obtained from scientific Institutes or the genomes can be synthetical synthesized as complementary DNA as IBV strains have been sequenced and the sequences have been published and are, thus, available. Furthermore, IBV strains can be isolated from the field. The methods to isolate IBV strains and to characterize the IBV strains are well known to the person skilled in the art. Valter Leonardo de Quadros 2011 (Dissertation, Das Infektiöse Bronchitis Virus (IBV): Molekularbiologische Untersuchungen zur Diagnostik and zum Vorkommen sowie zur Pathogenität des Genotyps IBV QX in spezifisch pathogenfreien (SPF) Broilern, Freie Universität Berlin), Worthington et al. 2009 (Avian Pathology 37(3), 247-257), Liu et al. 2009 (Virus Genes 38: 56-65), Dolz et al. 2006 (Avian Pathology 35 (2): 77-85), Farsang et al. 2002 (Avian Pathology 31: 229-236) and Feng et al. 2014 (Virus Genes 49: 292-303) describe how to isolate and differentiate different IBV strains.

IBV strains are typically differentiated by the coding sequence of the 51 subunit of the spike protein (Valastro et al. 2016. Infect Genet Evol. 39:349-364) but can also be differentiated by their complete nucleotide sequence or the sequences of specific proteins such as the spike protein, nucleocapsid protein, envelope (E) protein or membrane (M) glycoprotein. Because the spike protein determines host tropism and antigenicity of IBV, the IBV genotypes are classified by the coding sequence of the subunit 1 of the spike proteins. Alternatively, IBV strains can be differentiated by their serotype. Serotype classification involves serological assays of the virus involving serotype-specific antibodies.

In another specific aspect of the IBV spike protein or fragment thereof according to the present invention the spike protein or fragment thereof is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as H52, H120, excluding M41), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV spike protein or fragment thereof according to the present invention the spike protein or fragment thereof is not from a Beaudette genotype or serotype.

In another specific aspect of the IBV spike protein or fragment thereof according to the present invention the spike protein or fragment thereof is not from IBV strain M41.

In another specific aspect of the IBV spike protein or fragment thereof according to the present invention the spike protein or fragment thereof is from an IBV selected from a list of genotypes or serotypes or strains consisting of: Massachusetts (not M41), 4/91, QX, Q1, Italy 02, Arkansas, Connecticut, Georgia, LDT3, PL84084, Variant 2 and Brazil.

The wording "not M41" is used equivalent to excluding M41. Thus, the wording "Massachusetts (not Beaudette)" means that spike proteins or fragments thereof from Massachusetts strains such as H52 and H120 are comprised, but spike proteins or fragments thereof from M41 strains are excluded.

In another specific aspect of the IBV spike protein or fragment thereof according to the present invention the spike protein or fragment thereof is from an IBV selected from a list of genotypes or serotypes consisting of: Massachusetts (not M41), 4/91, QX, Q1, Arkansas, Variant 2 and Brazil.

In another specific aspect of the IBV spike protein or fragment thereof according to the present invention the spike protein or fragment thereof is from an IBV selected from a list of genotypes or serotypes consisting of Massachusetts (not M41) and 4/91.

In another specific aspect of the IBV spike protein or fragment thereof according to the present invention the Massachusetts strain is selected from a list consisting of: H120, H52, Spain/98/308, IBMA5-1, SD/97/01 and Spain/96/334.

In another specific aspect of the IBV spike protein or fragment thereof according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

In another specific aspect of the IBV spike protein or fragment thereof according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV spike protein or fragment thereof according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV spike protein or fragment thereof according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV spike protein or fragment thereof according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV spike protein or fragment thereof according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10 EG, TR8 and IB VAR2-06.

In another specific aspect of the IBV spike protein or fragment thereof according to the present invention the Brazil strain is selected from a list consisting of: BR-1, BR-2, 23/2013, and IBV/Brasil/351/1984.

In another specific aspect of the IBV spike protein or fragment thereof according to the present invention the spike protein or fragment thereof is from an IBV of Massachusetts (not M41) or 4/91 genotype or serotype.

In another specific aspect of the IBV spike protein or fragment thereof according to the present invention the spike protein or fragment thereof is from an IBV of Massachusetts (not M41) genotype or serotype.

In another specific aspect of the IBV spike protein or fragment thereof according to the present invention the spike protein or fragment thereof is from an IBV of 4/91 genotype or serotype.

In another specific aspect of the IBV spike protein or fragment thereof according to the present invention the IBV strain is H52, H120 or CR88.

In another specific aspect of the IBV spike protein or fragment thereof according to the present invention the IBV strain is H52 or H120.

In another specific aspect of the IBV spike protein or fragment thereof according to the present invention the IBV spike protein or fragment thereof consists of or comprises an amino acid sequence as shown in SEQ ID NO: 2, 3, 4, 5, 6, 7, 8 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, MD 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are of the same length.

A sequence comparison may be carried out over the entire lengths of the two sequences being compared or over fragments of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. In this context, "X" is any integer selected from 1 to 31 so that "SEQ ID NO: X" represents any of the SEQ ID NOs mentioned herein.

In another specific aspect of the IBV spike protein or fragment thereof according to the present invention the IBV spike protein or fragment thereof consists of or comprises an amino acid sequence as shown in SEQ ID NO: 2 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 3 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 4 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 5 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 6 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 7 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 8 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof is selected from a list of genotypes consisting of: GI-2 to 27, GII-1, GIII-1, GIV-1, GV-1, GVI-1.

Valastro et al 2016 (Infection, Genetics and Evolution 39; 349-364) describe a phylogeny-based classification system combined with a lineage nomenclature for the assignment of IBV strains. 6 genotypes (GI to GVI) are defined that together comprise 32 distinct viral lineages.

In another specific aspect of the IBV spike protein or fragment thereof according to the present invention the spike protein or fragment thereof is not from the GI-1 genotype. The GI-1 genotype relates to the Massachusetts genotype/serotype.

In another specific aspect of the avian coronavirus spike protein or fragment thereof according to the present invention said at least a part of the S2 subunit from an avian coronavirus with a restricted cell or tissue tropism is selected from the group consisting of: Infectious bronchitis virus (IBV); guinea fowl coronavirus (GfCoV) and turkey coronavirus (TCoV; turkey enteritis virus and bluecomb disease virus).

In another specific aspect of the avian coronavirus spike protein or fragment thereof according to the present invention said at least a part of the S2 subunit from an avian coronavirus with a restricted cell or tissue tropism is from IBV (infectious bronchitis virus).

In another specific aspect of the IBV spike protein or fragment thereof according to the present invention said at least a part of the S2 subunit is from an IBV selected from a list of genotypes or serotypes or strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as H52, H120; excluding M41), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88) or wherein said at least a part of the S2 subunit is not from IBV strain M41.

Thus, in another specific aspect of the IBV spike protein or fragment thereof according to the present invention said at least a part of the S2 subunit is not from IBV strain M41.

In another specific aspect of the IBV spike protein or fragment thereof according to the present invention said at least a part of the S2 subunit is from an IBV selected from a list of genotypes or serotypes or strains consisting of Massachusetts (not M41), 4/91, QX, Q1, Italy 02, Arkansas, Connecticut, Georgia, LDT3, PL84084, Variant 2 and Brazil.

In another specific aspect of the IBV spike protein or fragment thereof according to the present invention said at least a part of the S2 subunit is from an IBV selected from a list of genotypes or serotypes consisting of Massachusetts (not M41), 4/91, QX, Q1, Arkansas, Variant 2 and Brazil.

In another specific aspect of the IBV spike protein or fragment thereof according to the present invention the Massachusetts strain is selected from a list consisting of: H120, H52, Spain/98/308, IBMA5-1, SD/97/01 and Spain/96/334.

In another specific aspect of the IBV spike protein or fragment thereof according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

In another specific aspect of the IBV spike protein or fragment thereof according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV spike protein or fragment thereof according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV spike protein or fragment thereof according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV spike protein or fragment thereof according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV spike protein or fragment thereof according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10 EG, TR8 and IB VAR2-06.

In another specific aspect of the IBV spike protein or fragment thereof according to the present invention the Brazil strain is selected from a list consisting of: BR-1, BR-2, 23/2013 and IBV/Brasil/351/1984.

In another specific aspect of the IBV spike protein or fragment thereof according to the present invention said at least a part of the S2 subunit is from an IBV selected from a list of genotypes or serotypes consisting of Massachusetts (not M41) and 4/91.

In another specific aspect of the IBV spike protein or fragment thereof according to the present invention said at least a part of the S2 subunit is from an IBV Massachusetts (not M41) genotype or serotype.

In another specific aspect of the IBV spike protein or fragment thereof according to the present invention said at least a part of the S2 subunit is from an IBV strain H120, H52 or CR88.

In another specific aspect of the IBV spike protein or fragment thereof according to the present invention said at least a part of the S2 subunit is from an IBV strain H120 or H52.

In another specific aspect of the avian coronavirus spike protein or fragment thereof according to the present invention the at least a part of the S2 subunit is at least 1, 5, 10, 15, 20, 25, 50, 100, 150, 200, 250, 300, 350, 400 or 500 contiguous amino acids from a S2 subunit sequence of an avian coronavirus or IBV with a restricted cell or tissue tropism or a sequence having at least 90%, 95%, 96%, 97%, 98%, 99% sequence identity thereto.

In another specific aspect of the avian coronavirus or IBV spike protein or fragment thereof according to the present invention the at least a part of the S2 subunit is at least 1, 5, 10, 15, 20, 25, 50, 100, 150, 200, 250, 300, 350, 400 or 500 contiguous amino acids from a S2 subunit sequence of an avian coronavirus or IBV as described herein or a sequence having at least 90%, 95%, 96%, 97%, 98%, 99% sequence identity thereto.

In another specific aspect of the IBV spike protein or fragment thereof according to the present invention said at least a part of the S2 subunit from an IBV with a restricted cell or tissue tropism has at least 1, 5, 10, 15, 20, 25, 50, 100, 150, 200, 250, 300, 350, 400 or 500 contiguous amino acids of the amino acid sequence as shown in SEQ ID NO: 2, 3, 4, 5, 6, 7, 8 or a sequence having at least 90%, 95%, 96%, 97%, 98%, 99% sequence identity thereto.

In another specific aspect of the avian coronavirus or IBV spike protein or fragment thereof according to the present invention the coronavirus or IBV with restricted cell or tissue tropism is restricted to infection and/or replication in emryonated chicken eggs and/or primary chicken kidney cells.

In another specific aspect of the avian coronavirus or IBV spike protein or fragment thereof according to the present invention the coronavirus or IBV with restricted cell or tissue tropism is not infecting and/or replicating in EB66 cells.

In another specific aspect of the avian coronavirus or IBV spike protein or fragment thereof according to the present invention the coronavirus or IBV with restricted cell or tissue tropism is not infecting and/or replicating in BHK cells.

In another specific aspect of the avian coronavirus or IBV spike protein or fragment thereof according to the present invention the coronavirus or IBV with restricted cell or tissue tropism is not infecting and/or replicating in PBS-12SF and/or HEK 293T cells.

Fragment

In another specific aspect of the avian coronavirus or IBV spike protein or fragment thereof according to the present invention the fragment of the avian coronavirus or IBV spike protein has a length of at least 500, 750, 1000 or 1077 amino acids.

In another specific aspect of the avian coronavirus or IBV spike protein or fragment thereof according to the present invention the fragment of the avian coronavirus or IBV spike protein has a length of at least 1000 amino acids.

In another specific aspect of the avian coronavirus or IBV spike protein or fragment thereof according to the present invention the fragment of the avian coronavirus or IBV spike protein has a length of at least 500, 750, 1000 or 1075 amino acids from the N-Terminus.

The term "N-terminus" is well known to the person skilled in the art. The N-terminus is also termed amino-terminus, NH2-terminus, N-terminal end or amine-terminus.

When the protein is translated from messenger RNA, it is created from N-terminus to C-terminus. Thus, the N-terminus is the start of an amino acid chain (protein or polypeptide) comprising said amine group (—NH2).

In another specific aspect of the avian coronavirus or IBV spike protein or fragment thereof according to the present invention the fragment of the avian coronavirus or IBV spike protein is the ectodomain of the spike protein.

The term "ectodomain" is well known to a person skilled in the art. The spike protein comprises different functional parts, the signal sequence, the ectodomain, the transmembrane domain and the endodomain (from N-terminus to C-terminus). Thus, after cleavage of the signal sequence, the N-terminus of the spike protein starts with the ectodoamin. The IBV spike ectodoamins has a length of about 1075 amino acids and differs by a a few amino acids in length dependent on the IBV strain.

In another specific aspect of the avian coronavirus or IBV spike protein according to the present invention the aromatic amino acid at amino acid position 865 or the mutation at amino acid position 865 to an aromatic amino acid is genetically stable. Advantageously, the experimental data show that the aromatic amino acid at amino acid position 865 or the mutation at amino acid position 865 to an aromatic amino acid is genetically stable and remains stable over time (over passage).

The term "genetically stable" means that the aromatic amino acid at amino acid position 865 or the mutation at amino acid position 865 to an aromatic amino acid remains over time (over passage). Preferably, said aromatic amino acid at amino acid position 865 or the mutation at amino acid position 865 to an aromatic amino acid is still present after at least 3 passages, more preferably after at least 6 passages, even more preferably after at least 9 passages, even more preferably after at least 12 passages, most preferred after 15 passages in cell culture or tissue culture of an IBV having said avian coronavirus or IBV spike protein according to the present invention.

Nucleotide Sequences and Plasmids

Further, the present invention provides a nucleotide sequence encoding the spike protein or fragment thereof as described herein.

Further, the present invention provides a plasmid comprising a nucleotide sequence as described herein.

The term "nucleic acid" or "nucleic acid sequence" or "nucleotide sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificially modified ones such as biotinylated polynucleotides. Further, the terms "nucleic acid" and "polynucleotide" are interchangeable and refer to any nucleic acid. The terms "nucleic acid" and "polynucleotide" also specifically include nucleic acids composed of nucleotides with the nucleobases other than the five biologically occurring bases (adenine, guanine, thymine, cytosine and uracil).

The term "plasmid" refers to cytoplasmic DNA that replicates independently of the bacterial chromosome within a bacterial host cell. In a specific aspect of the present invention the term "plasmid" and/or "transfer plasmid" and/or "donor plasmid" refers to an element of recombinant DNA technology useful for construction of e.g. recombinant viruses or an expression cassette for insertion into a viral vector. In another specific aspect the term "plasmid" may be used to specify a plasmid useful for DNA vaccination purposes.

Cell

Further, the present invention provides a cell comprising a plasmid as described herein. The cell can be an eukaryotic or prokaryotic cell.

Viral Particle, Avian Coronavirus and IBV

Further, the present invention provides a viral particle comprising a spike protein or fragment thereof as described herein.

Further, the present invention provides an avian coronavirus comprising the spike protein or fragment thereof as described herein.

Further, the present invention provides an IBV (infectious bronchitis virus) comprising the spike protein as described herein.

In another specific aspect of the avian coronavirus or IBV according to the present invention the avian coronavirus or IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated IBV strain is one that is suitable for incorporation into an immunogenic composition comprising a modified live IBV.

In another specific aspect of the avian coronavirus or IBV according to the present invention the avian coronavirus or IBV is inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as poly-saccharides, peptides, proteins, or the like, or a combination thereof.

In another specific aspect of the avian coronavirus or IBV according to the present invention the avian coronavirus or IBV is genetically engineered.

The term "genetically engineered" refers to an avian coronavirus or IBV which has been mutated by using "reverse genetics" approaches. Preferably, the avian coro-navirus or IBV according to the present invention has been genetically engineered. The reverse genetics technique involves the preparation of synthetic recombinant viral RNAs and/or cDNA's. However, "reverse genetics" tech-niques are well known to the person skilled in the art.

In another specific aspect of the avian coronavirus or IBV according to the present invention the avian coronavirus or IBV is a recombinant.

The term "recombinant" as used herein relates to a RNA genome (or RNA sequence, cDNA sequence or protein) having any modifications that do not naturally occur to the corresponding RNA genome (or RNA sequence, cDNA sequence or protein). For instance, a RNA genome (or RNA sequence, cDNA sequence or protein) is considered "recom-binant" if it contains an insertion, deletion, inversion, relo-cation or a point mutation introduced artificially, e.g., by human intervention. Therefore, the RNA genomic sequence (or RNA sequence, cDNA sequence or protein) is not associated with all or a portion of the sequences (or RNA sequence, cDNA sequence or protein) with which it is associated in nature. The term "recombinant" as used with respect to a virus, means a virus produced by artificial manipulation of the viral genome. The term "recombinant virus" encompasses genetically modified viruses.

In another specific aspect of the avian coronavirus or IBV according to the present invention the avian coronavirus or IBV is chimeric.

The term "chimeric" refers to an avian coronavirus or IBV comprising one or more nucleotide sequences from another coronavirus or IBV. Preferably, the term refers to an IBV virus comprising one or more nucleotide sequences from another IBV strain.

In another specific aspect of the IBV according to the present invention the IBV is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Massachusetts (M41, H52, H120, Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88). Thus, it has to be understood that the IBV may of M41 genotype or serotype, however, the spike protein or fragment thereof is not from IBV strain M41.

In another specific aspect of the IBV according to the present invention the IBV is selected from a list of genotypes or serotypes or strains consisting of Massachusetts, 4/91, QX, Q1, Italy 02, Arkansas, Connecticut, Georgia, LDT3, PL84084, Variant 2 and Brazil.

In another specific aspect of the IBV according to the present invention the IBV is selected from a list of genotypes or serotypes consisting of Massachusetts, 4/91, QX, Q1, Arkansas, Variant 2 and Brazil.

In another specific aspect of the IBV according to the present invention the Massachusetts strain is selected from a list consisting of: H120, H52, Spain/98/308, IBMA5-1, SD/97/01, Beaudette, Spain/96/334 and M41-M21883.

In another specific aspect of the IBV according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

In another specific aspect of the IBV according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV according to the present invention the Variant 2 strain is selected from a list consisting of: IS/1494/06, IBV/Ck/EG/CU/4/2014, gamma-CoV/Ck/Poland/G052/2016, Eg/CLEVB-2/IBV/012, D1344/2/4/10 EG, TR8 and IB VAR2-06.

In another specific aspect of the IBV according to the present invention the Brazil strain is selected from a list consisting of: BR-1, BR-2, 23/2013 and IBV/Brasil/351/1984.

In another specific aspect of the IBV according to the present invention the spike protein or fragment thereof is from an IBV of Massachusetts or 4/91 genotype or serotype.

In another specific aspect of the IBV according to the present invention the spike protein or fragment thereof is from an Massachusetts IBV genotype or serotype.

In another specific aspect of the IBV according to the present invention the spike protein or fragment thereof is from an IBV of 4/91 genotype or serotype.

In another specific aspect of the IBV according to the present invention the IBV strain is H120, H52 or CR88.

In another specific aspect of the IBV according to the present invention the IBV strain is H120 or H52.

In another specific aspect of the IBV according to the present invention the IBV has a IBV spike protein or fragment thereof consisting of or comprising an amino acid sequence as shown in SEQ ID NO: 2, 3, 4, 5, 6, 7, 8 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV according to the present invention the IBV has an extended cell or tissue tropism.

In another specific aspect of the IBV according to the present invention the IBV is infecting and/or replicating in at least one cell line or cell as described herein. Preferably, the IBV is infecting and/or replicating in at least one cell line as described herein.

Further, the present invention provides a cell comprising:
the viral particle as described herein, or
the avian coronavirus or IBV as described herein.

In another specific aspect of the cell according to the present invention the cell is a cell line or cell selected from the list consisting of: primary chicken embryo cells, a chicken embryo fibroblast cell line, a duck embryonic stem cell line, a human embryonic kidney cell line, a baby hamster kidney cell line, an african green monkey kidney cell line, a rabbit kidney cell line, a canine kidney cell line, a chicken liver cell line, a bovine kidney cell line, a porcine kidney cell line and an insect cell line.

In another specific aspect of the cell according to the present invention the cell is a cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(Spodoptera frugiperda).

In another specific aspect of the cell according to the present invention the cell is a cell line selected from the list consisting of: DF-1, EB66, PBS-12, PBS-12SF, BHK, HEK 293T, Vero, MA104 and RK13.

In another specific aspect of the cell according to the present invention the primary chicken embryo cell is a fibroblast or a cell derived from liver or lung tissue.

Further, the present invention provides an immunogenic composition comprising:
the spike protein as described herein, or
the viral particle as described herein, or
the avian coronavirus or IBV as described herein.

Thus, the present invention also provides an immunogenic composition comprising an avian coronavirus or IBV comprising an avian coronavirus or IBV spike protein or fragment thereof, wherein at least a part of the S2 subunit is from an avian coronavirus or IBV with a restricted cell or tissue tropism, and wherein the amino acid at position 865 is an aromatic amino acid. Further, the present invention also provides an immunogenic composition comprising an avian coronavirus or IBV comprising a recombinant avian coronavirus or IBV spike protein or fragment thereof comprising a mutation at amino acid position 865. Further, the amino acid sequence of SEQ ID NO:1 is used for determining the position numbering in the spike protein. Preferably, the amino acid sequence of the spike protein is aligned to the amino acid sequence of SEQ ID NO:1

Further, the present invention provides a vaccine comprising:
the spike protein as described herein, or
the viral particle as described herein, or
the coronavirus or IBV as described herein.

Further, the present invention provides a modified live vaccine with an extended cell or tissue tropism comprising:
the spike protein as described herein, or
the viral particle as described herein, or
the coronavirus or IBV as described herein.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

The term "modified live" and "attenuated" are used interchangeable herein.

In another specific aspect of the immunogenic composition or vaccine according to the present invention the immunogenic composition or vaccine comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In another specific aspect of the immunogenic composition or vaccine according to the present invention the pharmaceutically acceptable carrier is phosphate buffered saline.

Preferably, the immunogenic composition further comprises sucrose gelatin stabilizer.

Preferably, the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta GA), SAF-M (Chiron, Emeryville CA), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition or vaccine according to the present invention the immunogenic composition or vaccine is effective in the treatment and/or prophylaxis of clinical signs caused by IBV in a subject of need. The terms "treatment and/or prophylaxis", "clinical signs" and "of need" have been defined elsewhere.

In another specific aspect of the immunogenic composition or vaccine according to the present invention said immunogenic composition or vaccine is formulated for a single-dose administration.

The volume for a single-dose has been defined elsewhere herein.

It has furthermore been shown that one dose of the immunogenic composition of the present invention is effective after the administration of such single dose of such immunogenic composition or vaccine.

In another specific aspect of the immunogenic composition or vaccine according to the present invention the immunogenic composition or vaccine is administered subcutaneously, intramuscularly, oral, in ovo, via spray, via drinking water or by eye drop.

In another specific aspect of the immunogenic composition or vaccine according to the present invention the immunogenic composition or vaccine comprises 1 to 10 $\log_{10}$ $EID_{50}$ per dose of the IBV.

In another specific aspect of the immunogenic composition or vaccine according to the present invention the immunogenic composition or vaccine comprises 2 to 5 $\log_{10}$ $EID_{50}$ per dose of the IBV.

In another specific aspect of the immunogenic composition or vaccine according to the present invention the immunogenic composition or vaccine comprises 2 to 4 $\log_{10}$ $EID_{50}$ per dose of the IBV.

Method for Manufacture, Culturing and Modification

Further, the present invention provides a method for altering the cell or tissue tropism of an avian coronavirus comprising the use of the avian coronavirus spike protein or fragment thereof as described herein.

Further, the present invention provides a method for extending the cell or tissue tropism of an avian coronavirus comprising the use of the avian coronavirus spike protein or fragment thereof as described herein.

Further, the present invention provides a method for the production or manufacture of an avian coronavirus with an extended cell or tissue tropism comprising the use of the avian coronavirus spike protein or fragment thereof as described herein.

Further, the present invention provides a method for culturing an avian coronavirus in a cell or tissue culture comprising the use of the avian coronavirus spike protein or fragment thereof as described herein.

Further, the present invention provides a method for modifying an avian coronavirus comprising modifying the amino acid position 865 in the spike protein of said avian coronavirus.

Further, the present invention provides a method for mutating the amino acid position 865 in an avian coronavirus spike protein comprising:
- a) providing an avian coronavirus spike nucleotide or protein sequence,
- b) identifying position 865 in the spike protein by alignment with a reference sequence,
- c) mutating the position 865 of the spike protein of step b) into an aromatic amino acid,
- d) obtaining the mutated spike protein of step c).

Furthermore, the present invention provides a method for mutating the amino acid position 865 in an avian coronavirus spike protein of an avian coronavirus comprising:
- a) providing an avian coronavirus,
- b) identifying position 865 in the spike protein by alignment with a reference sequence,
- c) mutating the position 865 of the spike protein of step b) into an aromatic amino acid,
- d) obtaining the mutated avian coronavirus of step c).

The term "obtaining" comprises the harvest, isolation, purification and/or formulation (e.g. finishing, inactivation and/or blending) of said spike protein or fragment thereof. The term "harvest" refers to collecting or recovering said avian coronavirus or IBV with the modified spike protein from the transfected or infected cell or cell line. Any conventional method known in the art can be used, e.g. any separation method. Well known methods in the art comprise centrifugation or filtration, such as using a semi-permeable membrane having a certain pore size. The term "isolation" comprises an isolation step of said avian coronavirus or IBV with the modified spike protein. Methods for the isolation from the transfected or infected cell or cell line are known to a person skilled in the art. Those methods comprise physical and/or chemical methods, including but are not limited to freeze thaw cycles, treatment with ultrasound and the alike. Methods for the "purification" of said said avian coronavirus or IBV with the modified spike protein from the isolate are known to a person skilled in the art, for example by those methods described in Protein purification methods—a practical approach (E. L. V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The vector can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein may also include further finishing steps as part of the final formulation process, like the addition of buffer, inactivation, neutralization steps and the alike.

In another specific aspect of the method according to the present invention the spike protein or fragment thereof has at amino acid position 865 an aromatic amino acid.

In another specific aspect of the method according to the present invention the aromatic amino acid at position 865 is introduced by a mutation.

In another specific aspect of the method according to the present invention the mutation is an amino acid substitution, deletion or insertion.

In another specific aspect of the method according to the present invention the amino acid at amino acid position 865 is mutated to an aromatic amino acid; or a polar amino acid at amino acid position 865 is mutated to an aromatic amino acid; or a glutamine at amino acid position 865 is mutated into a histidine.

In another specific aspect of the method according to the present invention the avian coronavirus is an IBV as described herein.

Thus, the present invention provides a method for altering the cell or tissue tropism of an IBV comprising the use of the avian coronavirus spike protein or fragment thereof as described herein.

Thus, the present invention provides a method for extending the cell or tissue tropism of an IBV comprising the use of the IBV spike protein or fragment thereof as described herein.

Thus, the present invention provides a method for the production or manufacture of an IBV with an extended cell or tissue tropism comprising the use of the IBV spike protein or fragment thereof as described herein.

Thus, the present invention provides a method for culturing an IBV in a cell or tissue culture comprising the use of the IBV spike protein or fragment thereof as described herein.

Thus, the present invention provides a method for modifying an IBV comprising modifying the amino acid position 865 in the spike protein of said IBV.

Thus, the present invention provides a method for mutating the amino acid position 865 in an IBV spike protein comprising:
- a) providing an IBV spike nucleotide or protein sequence,
- b) identifying position 865 in the spike protein by alignment with a reference sequence,
- c) mutating the position 865 of the spike protein of step b) into an aromatic amino acid,
- d) obtaining the mutated spike protein of step c).

Thus, the present invention provides a method for mutating the amino acid position 865 in an IBV spike protein of an IBV comprising:
- a) providing an IBV,
- b) identifying position 865 in the spike protein by alignment with a reference sequence,
- c) mutating the position 865 of the spike protein of step b) into an aromatic amino acid,
- d) obtaining the mutated IBV of step c).

In another specific aspect of the method according to the present invention the coronavirus spike protein is an IBV (infectious bronchitis virus) spike protein as described herein.

In another specific aspect of the method according to the present invention the aromatic amino acid at amino acid at position 865 or said mutation at amino acid position 865 leads to an extended cell or tissue tropism.

In another specific aspect of the method according to the present invention the avian coronavirus or IBV is infecting and/or replicating in at least one cell line or cell as described herein.

In another specific aspect of the method according to the present invention the numbering of amino acid position 865 is done as described herein.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for administration.

The present invention provides a kit comprising the viral particle, avian coronavirus, IBV, the immunogenic composition or vaccine as described herein.

In one specific aspect of the kit according to the present invention the kit further comprises an instruction letter for the treatment and/or prophylaxis of diseases of avians or an instruction letter for the treatment and/or prophylaxis of diseases of poultry or an instruction letter for the treatment and/or prophylaxis of IB.

In one specific aspect of the kit according to the present invention the kit further comprises a dispenser capable of administering a vaccine to said animal.

Method of Treatment

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular avian coronavirus or IBV infection in a flock or in the reduction in the severity of clinical signs caused by or associated with the particular avian coronavirus or IBV infection.

Further, the immunization of a subject in need with the immunogenic compositions as provided herewith, results in preventing infection of a subject by avian coronavirus or IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with an avian coronavirus or IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular avian coronavirus or IBV.

Further, the present invention provides a method of treating or preventing clinical signs caused by IBV in a subject of need, the method comprises administering to the subject a therapeutically effective amount of an immunogenic composition or vaccine as described herein.

As shown in the Examples, the immunogenic composition or vaccine as provided herein has been proven to be efficacious in treating or preventing clinical signs caused by IBV in a subject. Therefore, the experimental data show that the modification of the amino acid at amino acid position 865 into an aromatic amino acid does not have any impact on the efficacy of the vaccine.

The term "treating or preventing" refers to the lessening of the incidence of the particular IBV infection in a flock or the reduction in the severity of clinical signs caused by or associated with the particular IBV infection. Thus, the term "treating or preventing" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. The clinical signs of infection depend on the pathogen selected. Examples for such clinical signs include but are not limited to respiratory distress, nephritis, salphingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

Further, the present invention provides a method of reducing the ciliostasis in a subject of need, in comparison to a subject of a non-immunized control group of the same species, the method comprises administering to the subject a therapeutically effective amount of an immunogenic composition or vaccine as described herein.

As shown in the Examples, the immunogenic composition or vaccine as provided herein has been proven to be efficacious in reducing ciliostasis.

The term "ciliostasis" refers to a reduced movement of the cilia in the trachea. Thus, ciliostasis may be determined by examining the inner lining of the tracheal rings for the movement of the cilia. It is in the general knowledge of a person skilled in the art how to determine the movement of the cilia in the trachea.

Preferably, the movement of the cilia is not reduced from day 10 after challenge or infection, more preferably from day 5 after challenge or infection, more preferably from day 4 after challenge or infection, more preferably from day 3 after challenge or infection and most preferably from day 1 after challenge or infection.

or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the ciliostasis.

Further, the present invention provides the immunogenic composition or vaccine as described herein for use in a method for immunizing a subject, the method comprises administering to the subject a therapeutically effective amount of said immunogenic composition or vaccine.

Further, the present invention provides the immunogenic composition or vaccine as described herein for use in a method of treating or preventing clinical signs caused by IBV in a subject of need, the method comprises administering to the subject a therapeutically effective amount of said immunogenic composition or vaccine.

Further, the present invention provides the immunogenic composition or vaccine as described herein for use in a method of reducing the ciliostasis in a subject of need, in comparison to a subject of a non-immunized control group of the same species, the method comprises administering to the subject a therapeutically effective amount of said immunogenic composition or vaccine.

In one specific aspect of the method or use according to the present invention said subject is avian.

The term "avian" is well known to the person skilled in the art. The term "avian" encompasses all birds including poultry.

In one specific aspect of the method or use according to the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred as breeders.

In one specific aspect of the method or use according to the present invention said subject is selected from the list consisting of chicken, turkey, quail, or pheasant.

In one specific aspect of the method or use according to the present invention said subject is chicken.

In one specific aspect of the method or use according to the present invention the immunogenic composition or vaccine is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 μl per dose at any age. Preferably, the single-dose for eye drop vaccines has a total volume between about 5 μl and 70 μl and more preferably between about 20 μl and 50 μl with a single 20 μl, 25 μl, 30 μl, 35 μl, 40 μl, 45 μl or 50 μl dose being preferred. Most preferred, the single-dose for eye drop vaccines has a total volume between between about 30 μl and 50 μl with a single 30 μl, 35 μl, 40 μl, 45 μl or 50 μl dose being preferred.

Spray vaccines may contain the dose in a volume of 25 to 1000 μl for day-old poultry. Preferably, the single-dose for spray vaccines has a total volume between about 50 μl and 5000 μl, more preferably between about 75 μl and 2000 μl, more preferably between about 100 μl and 1000 μl, even more preferably between about 200 μl and 900 μl, even more preferably between about 300 μl and 800 μl and even more preferably between about 400 μl and 700 μl with a single 400 μl, 425 μl, 450 μl, 475 μl, 500 μl, 525 μl, 550 μl, 575 μl, 600 μl, 625 μl, 650 μl, 675 μl or 700 μl dose being preferred. Most preferred the single-dose has a total volume of 400 μl, 450 μl 500 μl, 550 μl, 600 μl, 650 μl or 700 μl.

The vaccine for in ovo vaccination may contain the dose in a volume of 50 to 100 μl, preferably 50 μl. Preferably, the single-dose for in ovo vaccines has a total volume between about 10 μl and 250 μl, more preferably between about 15 μl and 200 μl, even more preferably between about 20 μl and 150 μl, even more preferably between about 30 μl and 100 μl, even more preferably between about 30 μl and 75 μl and with a single 30 μl, 35 μl, 40 μl, 45 μl, 50 μl, 55 μl, 60 μl, 65 μl, 70 μl or 75 μl dose being preferred. Most preferred the single-dose has a total volume of 40 μl, 45 μl, 50 μl, 55 μl or 60 μl.

The vaccine for intramuscular or subcutaneous vaccination or one dose of a drinking water vaccine may contain the dose in a volume of 30 μl to 1000 μl. Preferably, the single-dose has a total volume between about 30 μl and 1000 μl, more preferably between about 50 μl and 500 μl, more preferably between about 75 μl and 250 μl and even more preferably between about 100 μl and 200 μl with a single 100 μl, 110 μl, 120 μl, 125 μl, 130 μl, 135 μl, 140 μl, 145 μl, 150 μl, 160 μl, 170 μl, 175 μl, 180 μl, 190 μl, 155 μl, or 200 μl dose being the most preferred.

In one specific aspect of the method or use according to the present invention the immunogenic composition or vaccine is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above. In addition to the first and second doses regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

Preferably, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary, the initial (first) vaccination is performed at 1-10 days of age and the second vaccination (booster) is performed with a live or inactivated vaccine at 6-12 or 16-18 weeks of age. More preferably, the initial (first) vaccination is performed at one day-of-age and the second vaccination (booster) is performed with a live or inactivated vaccine at 6-12 or 16-18 weeks of age.

In case in ovo vaccination is used, preferably the first administration is performed when embryos are between 15 to 19 days old, preferably at day 17, 18 or 19, most preferably at day 18 of age. A second administration can be performed within the first three weeks of age, preferably within the first 10 days of age.

In one specific aspect of the method or use according to the present invention said immunogenic composition or vaccine is administered subcutaneously, intramuscularly, oral, in ovo, via spray, via drinking water or by eye drop.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, most preferred the immunogenic composition is administered subcutaneously, intramuscularly, oral, in ovo, via spray, via drinking water or by eye drop.

Live IBV vaccines are preferably administered individually by eye drop, intranasal, intramuscular or subcutaneous. More preferably, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

In Ovo Administration

As outlined above, the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e.g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

Preferably, the vaccine is injected into embryonated eggs during late stages of the embryonation, generally during the final quarter of the incubation period, preferably 3-4 days prior to hatch. Preferably, the administration is performed when embryos are between 15 to 19 days old, preferably at day 17, 18 or 19, most preferably at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined. However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apatho-genic for embryos.

In one specific aspect of the method or use according to the present invention said immunogenic composition or vaccine is administered via eye drop.

Typically, the live vaccine for post-hatch administration comprises the attenuated IBV with a viral titer of $10^1$ to $10^8$ $EID_{50}$ (50% Egg Infective Dose) per dose, preferably with a viral titer of $10^2$ to $10^5$ $EID_{50}$ per dose and, more preferably, with a viral titer of $10^2$ to $10^4$ $EID_{50}$ per unit dose and, even more preferably, with a viral titer of $10^2$ to $10^3$ $EID_{50}$ per dose.

The live vaccine for in ovo administration typically comprises an amount of the attenuated IBV of $10^2$ to $10^7$ $EID_{50}$/embryo, preferably $10^2$ to $10^3$ $EID_{50}$/embryo in a volume of 50 to 100 μl, preferably 50 μl.

Preferably, the immunogenic composition of the present invention comprises the IBV of the present invention in amounts of about 1 to about 10 lop) EID (egg infective dose)$_{50}$/ml per dose, preferably about 2 to about 8 $log_{10}$ $EID_{50}$ per dose, preferably in an amount of about 2 to about 7 $log_{10}$ $EID_{50}$ per dose, more preferably in an amount of about 2 to about 6 lop) $EID_{50}$ per dose, even more preferably in an amount of about 2 to about 5 lop) $EID_{50}$ per dose, even more preferably in an amount of about 2 to about 4 $log_{10}$ $EID_{50}$ per dose, most preferably in an amount of about 2 to about 3 $log_{10}$ $EID_{50}$ per dose. More preferably, the immu-nogenic composition of the present invention comprises the IBV of the present invention in amounts of about 1, 1.5, 2, 2.5, 3, 3.5, 4, 4.5, 5, 5.5, 6, 6.5, 7, 7.5 or lop) $EID_{50}$ per dose.

In one specific aspect of the method or use according to the present invention the immunogenic composition or vac-cine comprises 1 to 10 lop) $EID_{50}$ per dose of the IBV.

In one specific aspect of the method or use according to the present invention the immunogenic composition or vac-cine comprises 2 to 5 $log_{10}$ $EID_{50}$ per dose of the IBV.

In one specific aspect of the method or use according to the present invention the immunogenic composition or vac-cine comprises 2 to 4 $log_{10}$ $EID_{50}$ per dose of the IBV.

In one specific aspect of the method or use according to the present invention the immunogenic composition or vac-cine is administered to subjects within the first week of age, within the first three days of age, within the first two days of age, or within the first day of age.

Preferably, the subject to be immunized is 1, 2, 3, 4, 5, 6, 7, 8, 9, 10, 11, 12, 13, 14, 15, 16, 17, 18, 19, 20 or 21 days of age. More preferably, said subject to be immunized is 1, 2, 3, 4, 5, 6, 7, 8, 9, 10, 11, 12, 13 or 14 days of age. Most preferably, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, preferably, the subjects are immunized within the first 24 h of age.

In one specific aspect of the method or use according to the present invention the immunogenic composition or vac-cine is administered to subjects within the first day of age. As shown in the Examples the immunogenic composition as provided herein has been proven to be safe and efficacious when administered to 1-day old poultry.

In one specific aspect of the method or use according to the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" or "virus titer" is a measure of the severity of an active viral infection, and can be determined by methods known to the person skilled in the art. The term "viral titre" is a measure of infectious units per volume of a virus preparation. Viral titre is an endpoint in a biological procedure and is defined as the dilution at which a certain proportion of tests carried out in parallel show an effect (Reed and Muench, 1938). The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of pro-phylactic and therapeutic interventions. Exemplary, the virus load or virus titer can be calculated by estimating the live amount of virus in an involved body fluid such as a number of RNA copies per milliliter of blood plasma.

The term "ciliostasis" is well known to the person skilled in that art. The surface of the trachea is covered with specialised epithelial cells, which are lined with numerous, motile, hair-like structures called cilia. The term "ciliosta-sis" encompasses the reduction or loss of cilia and/or loss or partial loss of ciliary activity. Ciliostasis can be determined without further ado by the person skilled in the art.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term "egg drop" encompasses a decreased egg production.

In one specific aspect of the method or use according to the present invention the treatment or prevention results in a prevention or reduction of ciliostasis as compared to subjects of a non-treated control group of the same species.

In one specific aspect of the method or use according to the present invention the treatment or prevention results in a prevention or reduction of kidney lesions as compared to subjects of a non-treated control group of the same species.

In one specific aspect of the method or use according to the present invention the treatment or prevention results in a prevention or reduction of egg drop as compared to subjects of a non-treated control group of the same species.

The present invention further provides the viral particle, avian coronavirus, IBV, immunogenic composition or vaccine as described herein for therapeutic use.

The present invention further provides the viral particle, avian coronavirus or IBV as described herein for use as an immunogen or vaccine.

The present invention further provides the viral particle, avian coronavirus, IBV, immunogenic composition or vaccine as described herein for use as a medicament.

The present invention further provides the use of the viral particle, avian coronavirus, IBV, immunogenic composition or vaccine as described herein for the manufacture of a medicament.

The present invention further provides the use of the viral particle, avian coronavirus, IBV, immunogenic composition or vaccine as described herein for the treatment and/or prophylaxis of IBV infections in a subject.

CLAUSES

The following clauses are also described herein:

1. An avian coronavirus spike protein or fragment thereof comprising an aromatic amino acid at position 865, wherein the spike protein or fragment thereof is not from IBV strain M41.
2. An avian coronavirus spike protein or fragment thereof, wherein at least a part of the S2 subunit is from an avian coronavirus with a restricted cell or tissue tropism, and wherein the amino acid at position 865 is an aromatic amino acid.
3. A recombinant avian coronavirus spike protein or fragment thereof comprising a mutation at amino acid position 865.
4. An IBV spike protein or fragment thereof comprising an aromatic amino acid at position 865, wherein the spike protein or fragment thereof is not from IBV strain M41.
5. An IBV spike protein or fragment thereof, wherein at least a part of the S2 subunit is from an IBV with a restricted cell or tissue tropism, and wherein the amino acid at position 865 is an aromatic amino acid.
6. A recombinant IBV spike protein or fragment thereof comprising a mutation at amino acid position 865.

Mutation 865

7. The avian coronavirus or IBV spike protein or fragment thereof of clause 1, 2, 4 or 5, wherein the aromatic amino acid at amino acid position 865 is introduced by a mutation.
8. The avian coronavirus or IBV spike protein or fragment thereof of clause 3, 6 or 7, wherein the mutation is an amino acid substitution, deletion or insertion.
9. The avian coronavirus or IBV spike protein or fragment thereof of any one of clauses 3 and 6 to 8, wherein the amino acid at amino acid position 865 is mutated to an aromatic amino acid; or a polar amino acid at amino acid position 865 is mutated to an aromatic amino acid; or a glutamine at amino acid position 865 is mutated into a histidine.

10. The avian coronavirus or IBV spike protein or fragment thereof of any one of clauses 1, 2, 4, 5 and 7, wherein the aromatic amino acid at amino acid position 865 is a histidine.

Extended Cell or Tissue Tropism

11. The avian coronavirus or IBV spike protein or fragment thereof of any one of clauses 1 to 10, wherein the aromatic amino acid at amino acid position 865 or said mutation at amino acid position 865 leads to an extended cell or tissue tropism of the avian coronavirus or IBV.
12. The avian coronavirus or IBV spike protein or fragment thereof of any one of clauses 1 to 11, wherein the avian coronavirus or IBV is infecting and/or replicating in at least one cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.
13. The avian coronavirus or IBV spike protein or fragment thereof of any one of clauses 1 to 12, wherein the avian coronavirus or IBV is infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).
14. The avian coronavirus or IBV spike protein or fragment thereof of any one of clauses 1 to 13, wherein the avian coronavirus or IBV is infecting and/or replicating in at least one cell line selected from the list consisting of: DF-1, EB66, PBS-12, PBS-12SF, BHK, HEK 293T, Vero, MA104 and RK13.

Numbering of Amino Acid Position 865

15. The avian coronavirus or IBV spike protein or fragment thereof of any one of clauses 1 to 14, wherein the numbering of amino acid position 865 refers to the amino acid position 865 in the spike protein of an IBV H52, an IBV H120 or an M41.
16. The avian coronavirus or IBV spike protein or fragment thereof of any one of clauses 1 to 14, wherein the numbering of amino acid position 865 refers to the amino acid position 865 in the spike protein as exemplarily given in SEQ ID NO:1.
17. The avian coronavirus or IBV spike protein or fragment thereof of any one of clauses 1 to 14, wherein the amino acid sequence of SEQ ID NO:1 is used for determining the position numbering in the spike protein.
18. The avian coronavirus or IBV spike protein or fragment thereof of any one of clauses 1 to 14, wherein for determining the amino position 865 in a spike protein the amino acid sequence is aligned to the amino acid sequence of SEQ ID NO:1.

19. The avian coronavirus or IBV spike protein or fragment thereof of any one of clauses 1 to 18, wherein the amino acid position 865 is within the S2 subunit of the spike protein.

20. The avian coronavirus or IBV spike protein or fragment thereof of any one of clauses 1 to 19, wherein the spike protein or fragment thereof has one or more of the following amino acids selected from the group consisting of:

862 is an alanine, and/or 864 is an alanine, and/or 866 is a valine, and/or 867 is an aspartate, and/or 868 is an arginine.

Spike

21. The avian coronavirus spike protein or fragment thereof of any one of clauses 1 to 3 and 7 to 20, wherein the avian coronavirus spike protein or fragment thereof is selected from the group consisting of: infectious bronchitis virus (IBV); guinea fowl coronavirus (Gf-CoV) and turkey coronavirus (TCoV; turkey enteritis virus and bluecomb disease virus).

22. The avian coronavirus spike protein or fragment thereof of any one of clauses 1 to 3 and 7 to 21, wherein the avian coronavirus is IBV (infectious bronchitis virus).

23. The IBV spike protein or fragment thereof of any one of clauses 4 to 22, wherein the spike protein or fragment thereof is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as H52, H120, excluding M41), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

24. The IBV spike protein or fragment thereof of any one of clauses 4 to 22, wherein the spike protein or fragment thereof is not from a Beaudette genotype or serotype.

25. IBV spike protein or fragment thereof of any one of clauses 4 to 24, wherein the spike protein or fragment thereof is not from IBV strain M41.

26. The IBV spike protein or fragment thereof of any one of clauses 4 to 25, wherein the spike protein or fragment thereof is from an IBV selected from a list of genotypes or serotypes or strains consisting of: Massachusetts (not M41), 4/91, QX, Q1, Italy 02, Arkansas, Connecticut, Georgia, LDT3, PL84084, Variant 2 and Brazil.

27. The IBV spike protein or fragment thereof of any one of clauses 4 to 26, wherein the spike protein or fragment thereof is from an IBV selected from a list of genotypes or serotypes consisting of Massachusetts (not M41), 4/91, QX, Q1, Arkansas, Variant 2 and Brazil.

28. The IBV spike protein or fragment thereof of any one of clauses 4 to 27, wherein the spike protein or fragment thereof is from an IBV selected from a list of genotypes or serotypes consisting of Massachusetts (not M41) and 4/91.

29. The IBV spike protein or fragment thereof of clause 27, wherein the Massachusetts strain is selected from a list consisting of: H120, H52, Spain/98/308, IBMA5-1, SD/97/01, Beaudette and Spain/96/334.

30. The IBV spike protein or fragment thereof of clause 27, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

31. The IBV spike protein or fragment thereof of clause 27, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

32. The IBV spike protein or fragment thereof of clause 27, wherein the Q1 strain is selected from a list consisting of: CK/CH/LDL/98I, CK/CH/LSD/08-10, J2, Q1, AR08ER22, AR08BA21 and Chile-295-10.

33. The IBV spike protein or fragment thereof of clause 27, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

34. The IBV spike protein or fragment thereof of clause 27, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10 EG, TR8 and IB VAR2-06.

35. The IBV spike protein or fragment thereof of clause 27, wherein the Brazil strain is selected from a list consisting of: BR-1, BR-2, 23/2013, and IBV/Brasil/351/1984.

36. The IBV spike protein or fragment thereof of any one of clauses 4 to 27, wherein the spike protein or fragment thereof is from an IBV of Massachusetts (not M41) or 4/91 genotype or serotype.

37. The IBV spike protein or fragment thereof of any one of clauses 4 to 27, wherein the IBV strain is H52, H120 or CR88.

38. The IBV spike protein or fragment thereof of any one of clauses 4 to 37, wherein the IBV spike protein or fragment thereof consists of or comprises an amino acid sequence as shown in SEQ ID NO: 2, 3, 4, 5, 6, 7, 8 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

39. The IBV spike protein or fragment thereof of any one of clauses 4 to 38, wherein the IBV spike protein or fragment thereof is selected from a list of genotypes consisting of: GI-2 to 27, GII-1, GIII-1, GIV-1, GV-1, GVI-1.

40. The IBV spike protein or fragment thereof of any one of clauses 4 to 39, wherein the spike protein or fragment thereof is not from the GI-1 genotype.

41. The avian coronavirus spike protein or fragment thereof of any one of clauses 2 and 7 to 40, wherein said at least a part of the S2 subunit from an avian coronavirus with a restricted cell or tissue tropism is selected from the group consisting of: Infectious bronchitis virus (IBV); guinea fowl coronavirus (GfCoV) and turkey coronavirus (TCoV; turkey enteritis virus and bluecomb disease virus).

42. The avian coronavirus spike protein or fragment thereof of any one of clauses 2 and 7 to 40, wherein said at least a part of the S2 subunit from an avian coronavirus with a restricted cell or tissue tropism is from IBV (infectious bronchitis virus).

43. The IBV spike protein or fragment thereof of any one of clauses 5 and 7 to 42, wherein said at least a part of the S2 subunit is from an IBV selected from a list of genotypes or serotypes or strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as H52, H120; excluding M41), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88) or wherein said at least a part of the S2 subunit is not from IBV strain M41.

44. The IBV spike protein or fragment thereof of any one of clauses 5 and 7 to 43, wherein said at least a part of the S2 subunit is from an IBV selected from a list of genotypes or serotypes or strains consisting of Massachusetts (not M41), 4/91, QX, Q1, Italy 02, Arkansas, Connecticut, Georgia, LDT3, PL84084, Variant 2 and Brazil.

45. The IBV spike protein or fragment thereof of any one of clauses 5 and 7 to 43, wherein said at least a part of the S2 subunit is from an IBV selected from a list of genotypes or serotypes consisting of Massachusetts (not M41), 4/91, QX, Q1, Arkansas, Variant 2 and Brazil.

46. The IBV spike protein or fragment thereof of clause 45, wherein the Massachusetts strain is selected from a list consisting of: H120, H52, Spain/98/308, IBMA5-1, SD/97/01 and Spain/96/334

47. The IBV spike protein or fragment thereof of clause 45, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

48. The IBV spike protein or fragment thereof of clause 45, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

49. The IBV spike protein or fragment thereof of clause 45, wherein the Q1 strain is selected from a list consisting of: CK/CH/LDL/98I, CK/CH/LSD/08-10, J2, Q1, AR08ER22, AR08BA21 and Chile-295-10.

50. The IBV spike protein or fragment thereof of clause 45, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

51. The IBV spike protein or fragment thereof of clause 45, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10 EG, TR8 and IB VAR2-06.

52. The IBV spike protein or fragment thereof of clause 45, wherein the Brazil strain is selected from a list consisting of: BR-1, BR-2, 23/2013 and IBV/Brasil/351/1984.

53. The IBV spike protein or fragment thereof of any one of clauses 5 and 7 to 45, wherein said at least a part of the S2 subunit is from an IBV selected from a list of genotypes or serotypes consisting of Massachusetts (not M41) and 4/91.

54. The IBV spike protein or fragment thereof of any one of clauses 5 and 7 to 45, wherein said at least a part of the S2 subunit is from an IBV strain H120, H52 or CR88.

55. The avian coronavirus spike protein or fragment thereof of any one of clauses 2 and 5 and 7 to 54, wherein the at least a part of the S2 subunit is at least 1, 5, 10, 15, 20, 25, 50, 100, 150, 200, 250, 300, 350, 400 or 500 contiguous amino acids from a S2 subunit sequence of an avian coronavirus or IBV with a restricted cell or tissue tropism or a sequence having at least 90%, 95%, 96%, 97%, 98%, 99% sequence identity thereto.

56. The avian coronavirus or IBV spike protein or fragment thereof of any one of clauses 2 and 5 and 7 to 54, wherein the at least a part of the S2 subunit is at least 1, 5, 10, 15, 20, 25, 50, 100, 150, 200, 250, 300, 350, 400 or 500 contiguous amino acids from a S2 subunit sequence of an avian coronavirus or IBV of any one of clauses 36 to 50 or a sequence having at least 90%, 95%, 96%, 97%, 98%, 99% sequence identity thereto.

57. The IBV spike protein or fragment thereof of any one of clauses 5 and 7 to 54, wherein said at least a part of the S2 subunit from an IBV with a restricted cell or tissue tropism has at least 1, 5, 10, 15, 20, 25, 50, 100, 150, 200, 250, 300, 350, 400 or 500 contiguous amino acids of the amino acid sequence as shown in SEQ ID NO: 2, 3, 4, 5, 6, 7, 8 or a sequence having at least 90%, 95%, 96%, 97%, 98%, 99% sequence identity thereto.

58. The avian coronavirus or IBV spike protein or fragment thereof of any one of clauses 2 and 5 and 7 to 57, wherein the avian coronavirus or IBV with restricted cell or tissue tropism is restricted to infection and/or replication in emryonated chicken eggs and/or primary chicken kidney cells.

59. The avian coronavirus or IBV spike protein or fragment thereof of any one of clauses 2 and 5 and 7 to 57, wherein the avian coronavirus or IBV with restricted cell or tissue tropism is not infecting and/or replicating in EB66 and/or BHK cells.

60. The avian coronavirus or IBV spike protein or fragment thereof of any one of clauses 2 and 5 and 7 to 57, wherein the avian coronavirus or IBV with restricted cell or tissue tropism is not infecting and/or replicating in PBS-12 and/or HEK 293T cells.

Fragment

61. The avian coronavirus or IBV spike protein or fragment thereof of any one of clauses 1 to 60, wherein the fragment of the avian coronavirus or IBV spike protein has a length of at least 500, 750, 1000 or 1077 amino acids.

62. The avian coronavirus or IBV spike protein or fragment thereof of any one of clauses 1 to 61, wherein the fragment of the avian coronavirus or IBV spike protein has a length of at least 1000 amino acids.

63. The avian coronavirus or IBV spike protein of any one of clauses 1 to 62, wherein the the aromatic amino acid at amino acid position 865 or the mutation at amino acid position 865 to an aromatic amino acid is genetically stable.

64. A nucleotide sequence encoding the spike protein or fragment thereof of any one of clauses 1 to 63.

65. A plasmid comprising a nucleotide sequence of clause 64.

66. A cell comprising a plasmid of clause 65.

67. A viral particle comprising a spike protein or fragment thereof of any one of clauses 1 to 63.

68. An avian coronavirus comprising the spike protein or fragment thereof of any one of clauses 1 to 63.

69. An IBV (infectious bronchitis virus) comprising the spike protein of any one of clauses 4 to 63.

70. The avian coronavirus or IBV of clauses 68 or 69, wherein the avian coronavirus or IBV is attenuated.

71. The avian coronavirus or IBV of any one of clauses 68 to 70, wherein the avian coronavirus or IBV is genetically engineered.

72. The avian coronavirus or IBV of any one of clauses 68 to 71, wherein the avian coronavirus or IBV is recombinant.

73. The avian coronavirus or IBV of any one of clauses 68 to 72, wherein the avian coronavirus or IBV is chimeric.

74. The IBV of any one of clauses 69 to 73, wherein the IBV is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Massachusetts (M41, H52, H120, Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

75. The IBV of any one of clauses 69 to 74, wherein the IBV is selected from a list of genotypes or serotypes or strains consisting of Massachusetts, 4/91, QX, Q1, Italy 02, Arkansas, Connecticut, Georgia, LDT3, PL84084, Variant 2 and Brazil.

76. The IBV of any one of clauses 69 to 75, wherein the IBV is selected from a list of genotypes or serotypes consisting of Massachusetts, 4/91, QX, Q1, Arkansas, Variant 2 and Brazil.

77. The IBV of clause 76, wherein the Massachusetts strain is selected from a list consisting of: H120, H52, Spain/98/308, IBMA5-1, SD/97/01, Beaudette, Spain/96/334 and M41-M21883.

78. The IBV of clause 76, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

79. The IBV of clause 76, wherein the QX strain is selected from a list consisting of: FR-L1450T-05, FR-L1450L-05, NL-L1449T-04, NL-L1449K-04, IBV/

Ck/SP/170/09, IBV/Ck/SP/79/08, IBV/Ck/SP/248/09, HBN, IBVQX, LX4, BJQ, CK/CH/LGD/03 and GB341/96.

80. The IBV of clause 76, wherein the Q1 strain is selected from a list consisting of: CK/CH/LDL/98I, CK/CH/LSD/08-10, J2, Q1, AR08ER22, AR08BA21 and Chile-295-10.

81. The IBV of clause 76, wherein the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

82. The IBV of clause 76, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

83. The IBV of clause 76, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10 EG, TR8 and IB VAR2-06.

84. The IBV of clause 76, wherein the Brazil strain is selected from a list consisting of: BR-1, BR-2, 23/2013 and IBV/Brasil/351/1984.

85. The IBV of any one of clauses 69 to 76, wherein the Spike protein or fragment thereof is from an IBV of Massachusetts or 4/91 genotype or serotype.

86. The IBV of any one of clauses 69 to 76, wherein the IBV strain is H120, H52 or CR88.

87. The IBV of any one of clauses 69 to 86, wherein the IBV has a IBV Spike Protein or fragment thereof consisting of or comprising an amino acid sequence as shown in SEQ ID NO: 2, 3, 4, 5, 6, 7, 8 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

88. The IBV of any one of clauses 69 to 87, wherein the IBV has an extended cell or tissue tropism.

89. The IBV of any one of clauses 69 to 88, wherein the IBV is infecting and/or replicating in at least one cell line or cell of any one of clauses 12 to 14.

90. A cell comprising:
   the viral particle of clause 67, or
   the avian coronavirus or IBV of any one of clauses 68 to 89.

91. The cell of clause 90, wherein the cell is a cell line or cell selected from the list consisting of: primary chicken embryo cells, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

92. The cell of clauses 90 or 91, wherein the cell is a cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

93. The cell of any one of clauses 90 to 92, wherein the cell is a cell line selected from the list consisting of: DF-1, EB66, PBS-12, PBS-12SF, BHK, HEK 293T, Vero, MA104 and RK13.

94. The cell of clause 91, wherein the primary chicken embryo cell is a fibroblast or a cell derived from liver or lung tissue.

95. An immunogenic composition comprising:
the spike protein of any one of clauses 1 to 63, or
the viral particle of clause 67, or
the avian coronavirus or IBV of any one of clauses 68 to 89.

96. A vaccine comprising:
the spike protein of any one of clauses 1 to 63, or
the viral particle of clause 67, or
the coronavirus or IBV of any one of clauses 68 to 89.

97. A modified live vaccine with an extended cell or tissue tropism comprising:
the spike protein of any one of clauses 1 to 63, or
the viral particle of clause 67, or
the coronavirus or IBV of any one of clauses 68 to 89.

98. The immunogenic composition or vaccine of any one of clauses 95 to 97, wherein the immunogenic composition or vaccine comprises a pharmaceutically acceptable carrier.

99. The immunogenic composition or vaccine of clause 98, wherein the pharmaceutically acceptable carrier is phosphate buffered saline.

100. The immunogenic composition or vaccine of any one of clauses 95 to 99, wherein the immunogenic composition or vaccine is effective in the treatment and/or prophylaxis of clinical signs caused by IBV in a subject of need.

101. The immunogenic composition or vaccine of any one of clauses 95 to 100, wherein the immunogenic composition or vaccine comprises 1 to 10 $\log_{10}$ $EID_{50}$ of the IBV.

102. The immunogenic composition or vaccine of any one of clauses 95 to 101, wherein the immunogenic composition or vaccine comprises 2 to 5 $\log_{10}$ $EID_{50}$ of the IBV.

103. The immunogenic composition or vaccine of any one of clauses 95 to 102, wherein the immunogenic composition or vaccine comprises 2 to 4 $\log_{10}$ $EID_{50}$ of the IBV.

104. A method for altering the cell or tissue tropism of an avian coronavirus comprising the use of the avian coronavirus spike protein or fragment thereof of any one of clauses 1 to 63.

105. A method for extending the cell or tissue tropism of an avian coronavirus comprising the use of the avian coronavirus spike protein or fragment thereof of any one of clauses 1 to 63.

106. A method for the production or manufacture of an avian coronavirus with an extended cell or tissue tropism comprising the use of the avian coronavirus spike protein or fragment thereof of any one of clauses 1 to 63.

107. A method for culturing an avian coronavirus in a cell or tissue culture comprising the use of the avian coronavirus spike protein or fragment thereof of any one of clauses 1 to 63.

108. A method for modifying an avian coronavirus comprising modifying the amino acid position 865 in the spike protein of said avian coronavirus.

109. A method for mutating the amino acid position 865 in an avian coronavirus spike protein comprising:

a) providing an avian coronavirus spike nucleotide or protein sequence,
b) identifying position 865 in the spike protein by alignment with a reference sequence,
c) mutating the position 865 of the spike protein of step b) into an aromatic amino acid,
d) obtaining the mutated spike protein of step c).

110. The method of any one of clauses 104 to 108, wherein the spike protein or fragment thereof has at amino acid position 865 an aromatic amino acid.

111. The method of any one of clause 108 to 110, wherein the aromatic amino acid at position 865 is introduced by a mutation.

112. The method of clause 111, wherein the mutation is an amino acid substitution, deletion or insertion.

113. The method of any one of clause 108 to 112, wherein the amino acid at amino acid position 865 is mutated to an aromatic amino acid; or a polar amino acid at amino acid position 865 is mutated to an aromatic amino acid; or a Glutamine at amino acid position 865 is mutated into a Histidine.

114. The method of any one of clauses 104 to 113, wherein the avian coronavirus is an IBV of any one of clauses 63 to 83.

115. The method of any one of clauses 104 to 114, wherein the coronavirus spike protein is an IBV (infectious bronchitis virus) spike protein of any one of clauses 3 to 57.

116. The method of any one of clauses 104 to 115, wherein the aromatic amino acid at amino acid at position 865 or said mutation at amino acid position 865 leads to an extended cell or tissue tropism.

117. The method of any one of clauses 104 to 116, wherein the avian coronavirus or IBV is infecting and/or replicating in at least one cell line or cell of any one of clauses 12 to 14.

118. The method of to any one of clause 108 to 117, wherein the numbering of amino acid position 865 is done according to any one of clauses 15 to 20.

Kit Clauses

119. A kit comprising the viral particle, avian coronavirus, IBV, the immunogenic composition or vaccine of any one of clauses 67 to 89 and 95 to 103.

120. The kit of clause 119, wherein the kit further comprises an instruction letter for the treatment and/or prophylaxis of diseases of avians or an instruction letter for the treatment and/or prophylaxis of diseases of poultry or an instruction letter for the treatment and/or prophylaxis of IB.

121. The kit of clauses 119 or 120, wherein the kit further comprises a dispenser capable of administering a vaccine to said animal.

Method of Treatment Clauses

122. A method for immunizing a subject comprising administering to such subject an immunogenic composition or vaccine of any one of clauses 95 to 103.

123. A method of treating or preventing clinical signs caused by IBV in a subject of need, the method comprises administering to the subject a therapeutically effective amount of an immunogenic composition or vaccine of any one of clauses 95 to 103.

124. A method of reducing the ciliostasis in a subject of need, in comparison to a subject of a non-immunized control group of the same species, the method comprises administering to the subject a therapeutically effective amount of an immunogenic composition or vaccine of any one of clauses 95 to 103.

125. The immunogenic composition or vaccine of any one of clauses 95 to 103 for use in a method for immunizing a subject, the method comprises administering to the subject a therapeutically effective amount of said immunogenic composition or vaccine.

126. The immunogenic composition or vaccine of any one of clauses 95 to 103 for use in a method of treating or preventing clinical signs caused by IBV in a subject of need, the method comprises administering to the subject a therapeutically effective amount of said immunogenic composition or vaccine.

127. The immunogenic composition or vaccine of any one of clauses 95 to 103 for use in a method of reducing the ciliostasis in a subject of need, in comparison to a subject of a non-immunized control group of the same species, the method comprises administering to the subject a therapeutically effective amount of said immunogenic composition or vaccine.

128. The method or use of any one of clauses 122 to 127, wherein said subject is avian.

129. The method or use of any one of clauses 122 to 128, wherein said subject is poultry.

130. The method or use of any one of clauses 122 to 129, wherein said subject is selected from the list consisting of chicken, turkey, quail, or pheasant.

131. The method or use of any one of clauses 122 to 130, wherein said subject is chicken.

132. The method or use of any one of clauses 122 to 131, wherein the immunogenic composition or vaccine is administered once.

133. The method or use of any one of clauses 122 to 131, wherein the immunogenic composition or vaccine is administered at two or more doses.

134. The method or use of any one of clauses 122 to 133, wherein said immunogenic composition or vaccine is administered subcutaneously, intramuscularly, oral, in ovo, via spray, via drinking water or by eye drop.

135. The method or use of any one of clauses 122 to 134, wherein said immunogenic composition or vaccine is administered via eye drop.

136. The method or use of any one of clauses 122 to 135, wherein the immunogenic composition or vaccine comprises 1 to 10 $\log_{10}$ EID$_{50}$ per dose of the IBV.

137. The method or use of any one of clauses 122 to 136, wherein the immunogenic composition or vaccine comprises 2 to 5 $\log_{10}$ EID$_{50}$ per dose of the IBV.

138. The method or use of any one of clauses 122 to 137, wherein the immunogenic composition or vaccine comprises 2 to 4 $\log_{10}$ EID$_{50}$ per dose of the IBV.

139. The method or use of any one of clauses 122 to 138, wherein the immunogenic composition or vaccine is administered to subjects within the first week of age, within the first three days of age, within the first two days of age, or within the first day of age.

140. The method or use of any one of clauses 122 to 139, wherein the immunogenic composition or vaccine is administered to subjects within the first day of age.

141. The method or use of any one of clauses 122 to 140, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

142. The method or use of any one of clauses 122 to 141, wherein the treatment or prevention results in a prevention or reduction of ciliostasis as compared to subjects of a non-treated control group of the same species.

143. The method or use of any one of clauses 122 to 142, wherein the treatment or prevention results in a prevention or reduction of kidney lesions as compared to subjects of a non-treated control group of the same species.

144. The method or use of any one of clauses 122 to 143, wherein the treatment or prevention results in a prevention or reduction of egg drop as compared to subjects of a non-treated control group of the same species.

145. The viral particle, avian coronavirus, IBV, immunogenic composition or vaccine of any one of clauses 67 to 89 and 95 to 103 for therapeutic use.

146. The viral particle, avian coronavirus, IBV of any one of clauses 67 to 89 for use as an immunogen or vaccine.

147. The viral particle, avian coronavirus, IBV, immunogenic composition or vaccine of any one of clauses 67 to 89 and 95 to 103 for use as a medicament.

148. Use of the viral particle, avian coronavirus, IBV, immunogenic composition or vaccine of any one of clauses 67 to 89 and 95 to 103 for the manufacture of a medicament.

149. Use of the viral particle, avian coronavirus, IBV, immunogenic composition or vaccine of any one of clauses 67 to 89 and 95 to 103 for the treatment and/or prophylaxis of IBV infections in a subject.

SEQUENCES OVERVIEW

Figure 1:
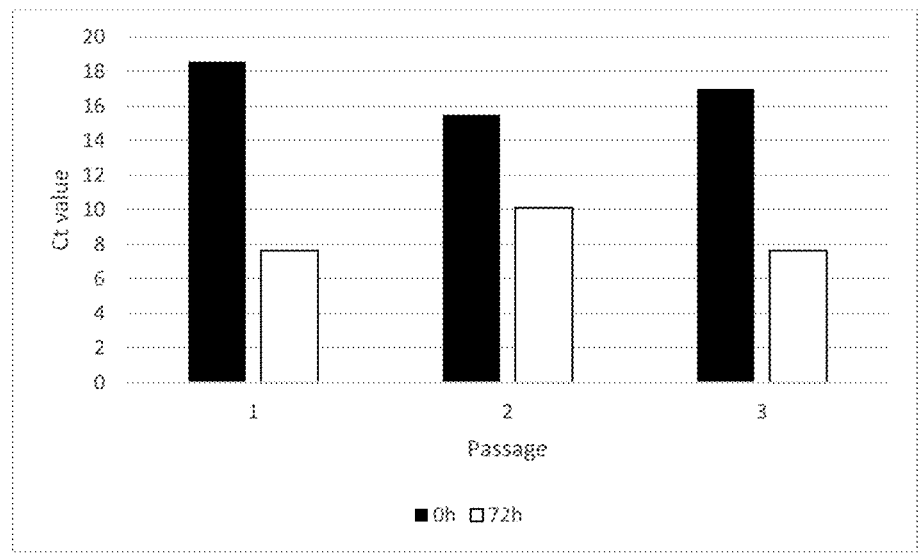
FIG. 1. Three blind passages of H52 rIBV S Q865H in EB66® cells. Assessment of replication via IBV-specific RT-qPCR at time points 0 and 72 hours post infection for all three passages.

SEQ ID NO:1 IBV H52 spike protein
SEQ ID NO:2 IBV H52 spike protein with Q865H mutation
SEQ ID NO:3 IBV CR88 spike with Q867H mutation
SEQ ID NO:4 IBV QX spike protein with Q868H mutation
SEQ ID NO:5 IBV Q1 spike protein with Q869H mutation
SEQ ID NO:6 IBV Var 2 spike protein with Q868H mutation
SEQ ID NO:7 IBV BR-I spike protein with Q872H mutation
SEQ ID NO:8 IBV Ark spike protein with Q871H mutation
SED ID NO:9 pUC57-s H52 rIBV S Q865H donor plasmid
SEQ ID NO:10 pUC57-s H52 rIBV S donor plasmid
SEQ ID NO:11 IBV CR88 spike protein
SEQ ID NO:12 pUC57-s CR88 mIBV donor plasmid
SEQ ID NO:13 pGEM-T CR88 S
SEQ ID NO:14 pUC57-s CR88 rIBV S Q867H donor plasmid SEQ ID NO:15 pGEM-T CR88 S Q867H SEQ ID NO:16-31 primers

EXAMPLES

The following examples are set forth below to illustrate specific embodiments of the present invention. These examples are merely illustrative and are understood not to limit the scope or the underlying principles of the present invention.

Example 1

Generation of a Recombinant IBV H52 in which the Amino Acid 865 of the Spike Protein is Mutated to a Histidine For the generation of recombinant IBV the method of targeted RNA recombination as described by van Beurden et al. (Virol J. 2017; 14(1):109) is applied.

Donor Plasmid Construction

The H52 spike protein sequence (SEQ ID NO:1) is amplified via PCR using primers 1044 and 1045 (table 1) and cloned into pGEM®-T vector system (Promega) yielding the plasmid pGEM-T IBV H52 spike. The QuikChange-Multi Site-Directed Mutagenesis Kit (Agilent Technologies) with primer PO2079 (table 1) is used according to kit protocol to introduce a mutation from glutamine to histidine at the position 865 in H52 spike S2 subunit (SEQ ID NO:2). Positive plasmids are identified via NcoI and NsiI restriction digest prepared from clonal bacterial cultures after transformation. To identify plasmids with the targeted mutation, Sanger sequencing of plasmids with the expected restriction pattern is performed using primers PO617 and PO634 (table 1).

TABLE 1

Primers for cloning, site directed mutagenesis and characterization of the pGEM-T IBV H52 spike plasmid.

| SEQ ID NO: | Name | Sequence |
|---|---|---|
| 16 | PO1044 | ttaattaagtgtggtaa gttgcttgtaagag atgttggtaacacc tc |
| 17 | PO1045 | ctcgagcgacttattcaat aaattcatcattaaa cagacttcttagg |
| 18 | PO2079 | ccatacaagcaaatgct cacgtggatcgtc ttataactg |
| 19 | PO619 | tgctgcttcctttaataag |
| 20 | PO634 | aacactataccattaggtgc |

To generate the H52 donor plasmid pUC57-s H52 rIBV S Q865H (SEQ ID NO:9) the NEBuilder HiFi DNA Assembly Cloning Kit (NEB) is used according to the kit protocol. For Gibson assembly, the H52 S Q865H sequence is amplified from the pGEM-T IBV H52 S Q865H plasmid via PCR. Further, two PCRs are performed to generate the flanking sequences of the spike in the context of the IBV H52 viral genome including a EcoRV and BlpI restriction site, respectively (table 2). For this, the pUC57-s IBV-5-1b-S-SIR-3T donor plasmid described by van Beurden et al., hereafter referred to as pUC57-s H52 rIBV donor plasmid (SEQ ID NO:10) is used as template. The correct size and purity of the PCR are products is determined via agarose gel, subsequently the PCR products are purified with the QIA quick PCR purification kit (QIAGEN). In parallel, the pUC57-s H52 rIBV donor plasmid is digested with EcoRV and BlpI to obtain the donor plasmid backbone sequence of roughly 7000 base pairs for Gibson assembly. Positive plasmids are identified by restriction digest with EcoRV and XbaI. Positive plasmids are sequences with primers PO619 and PO634 (table 1) to confirm the presence of the Q865H mutation in the spike S2 subunit.

TABLE 2

Setup for generation of PCR products to obtain the pUC57-s H52 rIBV S Q865H donor plasmid with Gibson HiFi assembly.

| PCR | product | Template | SEQ ID NO: | Primer name | Primer sequence |
|---|---|---|---|---|---|
| 1 | 5' spike flank | pUC57-s H52 rIBV | 21 | PO1783 | cagagcacaagtttg atcttgtgatatctg atatgtatacagaca atgattc |
| | | | 22 | PO1762 | gtgttaccaacatct cttaccagtaactta cc |
| 2 | spike | pGEM-T IBV H52 S Q865H | 23 | PO1765 | ttactggtaagagat gttggtaacacctct tttac |
| | | | 24 | PO1766 | ggactttggatcatt aaacagacttttag gtctg |
| 3 | 3' spike flank | pUC57-s H52 rIBV | 25 | PO1763 | aaagtctgtttaatg atccaaagtcccact ag |
| | | | 26 | PO1788 | cttaactcctggaat tactaaccacgtgta ccaaaataaacaaca agc |

Targeted RNA Recombination and Rescue of Recombinant IBV

The H52 murinized (m)IBV helper virus and recombinant IBV are generated as described by van Beurden et al. (Virol J. 2017; 14(1):109). Briefly, for the generation of H52 rIBV S Q865H, LR7 cells are infected with H52 mIBV and electroporated with an in vitro transcript generated from the pUC57-s H52 S Q865H donor plasmid (SEQ ID NO:9) and subsequently injected into 8-day-old embryonated SPF chicken eggs (VALO BioMedia). After up to eight days of incubation, the allantoic fluids of all eggs are analyzed separately for rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers PO765 and PO1324 (table 3) binding in H52 IBV lab and H52 IBV S spike are used to distinguish recombinant IBV from mIBV. The positive allantoic fluid of one egg inoculated with the infected and electroporated LR7 cells is used for an end-point dilution in 8-day-old embryonated SPF eggs. Nucleic acids isolation and sample analysis is conducted as described above. The same procedure is applied for a second end-point dilution procedure. Afterwards, one positive-tested allantoic fluid is used for propagation in 10-day-old embryonated SPF chicken eggs. The allantoic fluid is diluted 1:1000 in 1×PBS and 100 µl are injected per egg, which are subsequently incubated at 37.5° C. and 60% humidity. Allantoic fluid is harvested 48 hours post inoculation, pooled, cleared from debris by centrifugation and stored at −80° C.

TABLE 3

| Primers for confirmation of H52 rIBV S Q865H rescue after targeted RNA recombination. | | |
|---|---|---|
| SEQ ID NO: | name | sequence |
| 27 | PO765 | tgacttggtttgaagatggc |
| 28 | PO1324 | ccccatgtaaatgccaacca |

Conclusion Example 1: A Recombinant H52 IBV with a Mutation from Glutamine to Histidine at Position 865 of the Spike is Rescued In Vitro and in Ovo Characterization of Recombinant IBV
Determination of Embryo Infectious Dose 50% ($EID_{50}$)

An aliquot of the virus stock is thawed and 10-fold diluted in 1×PBS to determine the 50% embryo infectious dose ($EID_{50}$) by inoculation of 100 µl into the allantoic cavity of five 8-day old embryonated chicken eggs per dilution. Eggs are incubated at 36.5° C., 60% humidity until 7 days post inoculation. Eggs with dead embryos after 24 hours are excluded from the experiment. All other eggs with dead embryos at 7 days post inoculation are considered positive. All eggs with living embryos are canceled from the bottom at 7 days post inoculation to identify dwarfs, which are considered positive. The $EID_{50}$/ml is calculated with the formula of Reed and Muench (Am J Epidemiol, 1938; 27(3):493-497).
Tissue Culture Infectious Dose 50% ($TCID_{50}$)

Eb66® cell viability is analyzed with BioRad TC20 and trypan blue with the gate set to 6-13 µm. Per 96 well 2×10⁶ living Eb66® cells/ml in EX-CELL® EBx™ GRO-I Serum-Free Media+2.5 mM L-Glutamine are seeded 1 day prior to inoculation and incubated at 37° C. and 7.5% CO2. A 10-fold serial dilution of the virus in Eb66® cell medium is performed and 100 µl per dilution (at least 4 replicates per dilution) are added to Eb66® cells after removing the culture medium. If allantoic fluid is used for infection it is passed though a 0.45 µm pore sized filter prior to dilution. Infected cells are incubated for 72 hours followed by immunofluorescence staining to identify positive wells. Medium is aspirated from all wells, which are subsequently washed with 1×PBS before the addition of 100 µl ethanol per well for cell fixation for 10 min at RT and subsequent air drying of the cells. The cells are incubated with 100 µl of primary chicken anti-IBV Mass serum (Boehringer Ingelheim), diluted 1:250 in 1×PBS, for 45 min at room temperature. After removal of the primary antibody each well is washed three times with 1×PBS. 100 µl of secondary Alexa Fluor 488 goat anti-chicken IgG antibody (ThermoFisher Scientific, 1:500 dilution in 1×PBS) are added and incubated for 45 min at room temperature in the dark. After removal of the secondary antibody, each well is washed three times with 1×PBS, leaving the final wash on the cells. Positive wells are identified by fluorescence microscopy and recorded to calculate the $TCID_{50}$/ml with the formula of Reed and Muench (Am J Epidemiol, 1938; 27(3):493-497).
Passaging of rIBV in Eb66® Cells To analyze if H52 rIBV S Q865H is able to replicate in cells, three consecutive blind passages are performed in EB66®. The cells are seeded at a density of 4×10⁵ cells/ml in EX-CELL® EBx™ GRO-I Serum-Free Media+2.5 mM L-Glutamine into T25 flasks with a total volume of 5 ml and are infected with a 1/100 dilution of H52 rIBV S Q865H. The cultures are incubated for 72 hours at 37° C. and 7.5% CO2 and shaking at 100 rpm. The culture is harvested and stored at −80° C. For passages 1, 2, and 3 virus replication is assessed via RT-qPCR for the For this, 250 µl of the cell suspension are removed directly after inoculation (time point 0 h) and after harvest (time point 72 h) for nucleic acid isolation. Nucleic acids are isolated with the MagMAX™ Core Nucleic Acid Purification Kit (ThermoFisher) and the KingFisher™ Duo Prime Purification System (ThermoFisher). The RT-qPCR to detect the relative amount of IBV RNA is performed with a protocol adapted from Callison et al. (J Virol Methods. 2006; 138 (1-2):60-5) as described above. Indeed the Q865H mutation in the spike of H52 IBV is sufficient to enable cell culture replication of the egg-restricted H52. The H52 rIBV S Q865H replicated efficiently in all three passages, as represented by the decrease in the ct value between time point of infection (0h) and harvest (72) as depicted in FIG. 1. Thus, it is apparent that the modification to an Histidine at position 865 is genetically stable. Further, the IBV retains its extended cell culture/tissue tropism after 3 passages.

Figure 2:
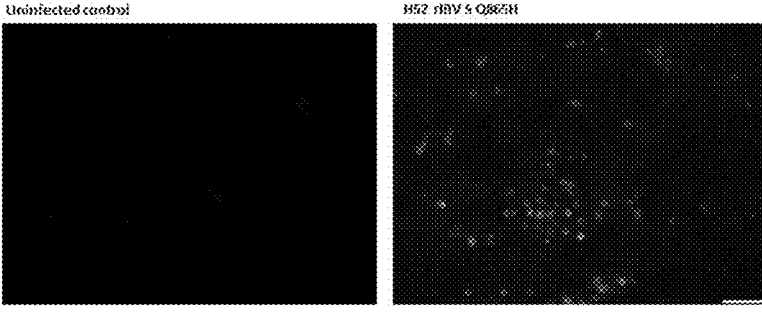
FIG. 2. Immunoflurescence staining of EB66® cells infected by H52 rIBV S Q865H in comparison to an uninfected negative control.
Figure 3:
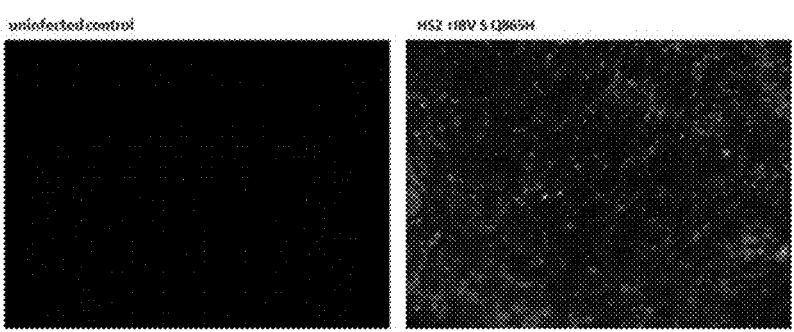
FIG. 3. Immunofluorescence staining of BHK cell infection by passage 3 of H52 rIBV S Q865H in comparison to an uninfected negative control.

In addition, the infectious titers for the allantoic fluid stock ($10^{7.32}$ $EID_{50}$/ml) and Eb66® passage P3 ($10^{5.25}$ $TCID_{50}$/ml, $10^{8.13}$ $EID_{50}$/ml) are determined via immunofluorescence staining (FIG. 2). They confirm efficient replication of H52 rIBV S Q865H during the Eb66® passaging process and sustained infectivity in SPF eggs. The Q865H mutation therefore enables replication in cell lines without disturbing the ability to replicate in ovo.
Infection of BHK Cells with H52 rIBV S Q865H The ability to infect BHK cells is analyzed for the allantoic fluid stocks of H52 rIBV S Q865H and H52 rIBV or an uninfected negative control. BHK cells are seeded in MEM (SAFC)+5% FCS (SAFC)+25 µg/ml L-Gentamicin (Gibco) medium into 12-well plates to reach 80 to 90% confluence on the next day. The cells are incubated at 37° C. and 5% CO2. Before infection the allantoic fluid virus stocks are set to 10⁶ to 10⁷ $EID_{50}$/ml and passed through a 0.45 µm pore sized filter. Afterwards, they are diluted 1/10 in medium and BHK cells are infected with 100 µl/well after aspiration of medium. After 72 hours the supernatant is taken off and the immunofluorescence assay as described for the $TCID_{50}$ assay above is performed and the stained cells are analyzed by fluorescence microscopy (FIG. 3).

Figure 4:
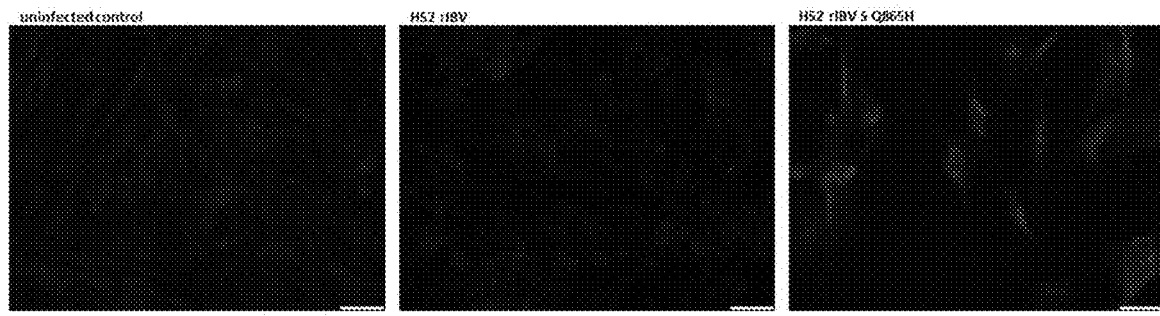
FIG. 4. Immunofluorescence staining of BHK cell infection by passage 3 of H52 rIBV S Q865H in comparison to an uninfected negative control and infection with H52rIBV wild type.

In a second experiment, the infection procedure described above is repeated. 72 hours post infection the supernatant is taken off and the cells are washed with 1×PBS and 50 µl TrypLE Select (ThermoFisher Scientific) are added to detach cells. Cells are resuspended in supernatant and transferred to a T25 flask with 80-90% confluent BHK cells and 5 ml fresh medium (P2), which is incubated for 72 hours. Again, the supernatant and cells are collected and transferred to a T75 flask with 80-90% confluent BHK cells and 10 ml fresh medium, which is incubated for 72 hours (P3). The supernatant is harvested. The cells are detached by trypsin treatment and seeded into 12 well plates at a ratio of 1 to 3 in fresh medium and incubated until the next day. Medium is aspirated, and the immunofluorescence assay as described above is performed (FIG. 4). In both experiments, infected BHK cells are detected for H52 rIBV S Q865H, while cells infected with H52 rIBV wild type and the uninfected negative control remain negative as expected.

Conclusion Example 1: The data show that the mutation to Histidine at the position 865 of the spike sequence (reference sequence for the numbering is SEQ ID NO:1) in an IBV leads to an extended cell culture and tissue tropism. An H52 recombinant IBV having the Q865H mutation in the spike protein can be efficiently cultured in different cell lines such as EB66 and BHK cells. It is assumed that said IBV can be cultured in other cell lines as well. Further, said mutation has no impact on in ovo replication of the virus.

Example 2

Generation of Recombinant IBV CR88 in which the Amino Acid 867 of the Spike Protein is Mutated to a Histidine In order to determine if the change to a histidine at position 865 in the IBV spike can also be applied to other genotypes or serotypes, the spike amino acid sequence (SEQ ID NO:11) of the CR88 IBV strain is aligned to the H52 Spike amino acid sequence (SEQ ID NO:1) to determine the position equivalent to amino acid position 865 of H52 spike for IBV CR88 spike, which is determined as the glutamine at position 867 of the CR88 spike.

Construction of an IBV CR88 Murinized Donor Plasmid

To generate the CR88 murinized (m)IBV donor plasmid the donor sequence is synthesized by a commercial supplier: 497 nucleotides of the 5' UTR of the CR88 genome are fused to the 3' part of the lab region (752 bases) and the first 72 nucleotides coding for the CR88 IBV spike, followed by 3753 nucleotides of the MHV spike ectodomain, continuing with the terminal 210 nucleotides of the CR88 IBV spike and the following sequence until the 3' end of the genome. In addition, a SacI restriction site and the sequence of the T7 promoter are added to the 5' end of the donor region, as well as a 100× polyA sequence, followed by a Nod restriction site for linearization at the 3' end, respectively. A silent A to C mutation at position 5634 of the assembled sequence is introduced to generate an XhoI restriction site. The synthesized sequence is inserted into pUC57-simple to yield the pUC57-s CR88 mIBV donor plasmid (SEQ ID NO:12).

Rescue of CR88 mIBV

CR88 mIBV is rescued in analogy to H52 mIBV (van Beurden et al. Virol J. 2017; 14(1):109) with some alterations: The virus allantoic fluid stock is concentrated via ultracentrifugation before isolation of the viral RNA for electroporation. 18 ml of viral allantoic fluid are centrifuged at 50,000×g for 2 hours through a 2 ml 20% Sucrose cushion in TNE (Tris, NaCl, EDTA) buffer. The supernatant is discarded and the pellet resuspended in 150 µl TNE buffer followed by RNA isolation with QIAamp viral RNA mini kit (Qiagen). Further, chicken embryo fibroblasts (CEFs) instead of BHK cells are used for electroporation (2 pulses 250 V/300 µF, 10 sec break) and 1.25% DMSO is added to the electroporation mixture.

Donor Plasmid Construction

The CR88 spike nucleic acid sequence with flanking sequences is synthesized by a commercial supplier and cloned into pGEM-T (SEQ ID NO:13). It is used as a template for site directed mutagenesis to change the glutamine at amino acid position 867 of the IBV CR88 spike (SEQ ID NO:11) into a histidine (SEQ ID NO:3). For this, the QuikChangeMulti Site-Directed Mutagenesis Kit (Agilent Technologies) according to the manufacturer's protocol and the primer PO1884 (table 4) designed by the corresponding online tool are used. Positive plasmids are identified by restriction digest and analyzed for the presence of the desired mutation by Sanger sequencing with primer PO619 and PO634 (table 4). For the generation of the pUC57-s CR88 rIBV S Q867H donor plasmid (SEQ ID NO:14), the pGEM-T CR88 S Q867H plasmid containing the mutated CR88 spike sequence (SEQ ID NO:15) is digested with PacI, XhoI and PvuI. The band corresponding to the spike is cut from the gel and purified with the QIAquick gel extraction kit (Qiagen). Further, the CR88 mIBV donor plasmid (SEQ ID NO:12) is digested with PacI, XhoI and KpnI to obtain the donor plasmid backbone. The band with the highest molecular weight is cut from the gel and purified via QIAquick Gel Extraction Kit (Qiagen). The purified spike insert and CR88 donor plasmid backbone are ligated using T4 DNA ligase (ThermoFisher Scientific) at 16° C. over night. The ligation mixture is transformed into NEB 5-α competent E. coli (NEB) by heat shock. After GeneJET Plasmid Miniprep Kit (ThermoFisher Scientific), positive plasmids are identified by restriction digest and characterized for the targeted mutation by Sanger sequencing with primers PO619 and PO634 (table 4).

Targeted RNA Recombination and Rescue of Recombinant IBV

For rescue of CR88 rIBV S Q867H, LR7 cells are infected with CR88 mIBV and electroporated with in vitro transcript generated from the NotI linearized pUC57-s CR88 S Q867H donor plasmid, and subsequently injected into 8-day-old embryonated SPF chicken eggs (VALO BioMedia). After up to eight days of incubation, the allantoic fluids of all eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers PO1728 and PO1729 (Table 4) binding in CR88 IBV lab and CR88 IBV S spike are used to distinguish recombinant IBV from mIBV. The positive allantoic fluid of the egg inoculated with the highest dilution of LR7 cells is used for an end-point dilution in 8-day-old embryonated SPF eggs. Nucleic acid isolation is conducted as described above. Samples are analyzed via RT-qPCR conducted according to the protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the StepOnePlus or the ABI7900 HT Fast Real-Time PCR Systems (ThermoFisher Scientific). Afterwards, one positive-tested allantoic fluid of a high dilution is used for propagation in 8-day-old embryonated SPF chicken eggs. The allantoic fluid is diluted 1:100 in 1×PBS and 100 µl is injected per egg which are subsequently incubated at 37.5° C. and 60% humidity. Allantoic fluid is harvested at 48 hours post inoculation, cleared from debris by centrifugation and stored at −80° C.

TABLE 4

SDM primer to obtain the CR88 S Q867H
mutation and sequencing primers for
confirmation of the targeted mutation
and confirmation of CR88 rIBV rescue.

| SEQ ID NO: | Name | Sequence |
|---|---|---|
| 29 | PO1884 | ctattcaggcagatgctcat gttgatcgtcttattacag |
| 19 | PO619 | tgctgcttcctttaataag |

53

TABLE 4-continued

SDM primer to obtain the CR88 S Q867H
mutation and sequencing primers for
confirmation of the targeted mutation
and confirmation of CR88 rIBV rescue.

| SEQ ID NO: | Name | Sequence |
|---|---|---|
| 20 | PO634 | aacactataccattaggtgc |
| 30 | PO1728 | tcagcgtggacatgtggtta |
| 31 | PO1729 | ccccatataggtgccaacct |

54

In Vitro and in Ovo Characterization of Recombinant IBV

The determination of EID50, TCID50 as well as the passaging procedure in Eb66 or BHK cells are performed as described in example 1 and similar results are obtained with CR88 rIBV S Q865H.

Conclusion example 2: The data show that the mutation to Histidine at the position 867 of the CR88 spike sequence (reference sequence for the numbering is SEQ ID NO:1) in an IBV leads to an extended cell culture and tissue tropism. An CR88 recombinant IBV having the Q867H mutation in the spike protein can be efficiently cultured in different cell lines such as EB66 and BHK cells. It is assumed that said IBV can be cultured in other cell lines as well. Further, said mutation has no impact on in ovo replication of the virus.

The invention claimed is:

1. An avian coronavirus spike protein comprising an aromatic amino acid at position 865, wherein the spike protein provides extended cell or tissue tropism without requiring a change to the Beaudette specific motif, wherein the spike protein is not from infectious bronchitis virus (IBV) strain M41, and wherein the amino acid sequence of SEQ ID NO:1 is used for determining the position numbering in the spike protein.

2. An avian coronavirus spike protein, wherein at least a part of the S2 subunit is from an avian coronavirus with a restricted cell or tissue tropism, wherein the amino acid at position 865 is an aromatic amino acid, wherein the spike protein provides extended cell or tissue tropism without requiring a change to the Beaudette specific motif, and wherein the amino acid sequence of SEQ ID NO:1 is used for determining the position numbering in the spike protein.

3. The avian coronavirus spike protein of claim 1, wherein the avian coronavirus is IBV (infectious bronchitis virus).

4. The avian coronavirus spike protein of claim 1, wherein the aromatic amino acid at amino acid position 865 is introduced by a mutation.

5. The avian coronavirus spike protein of claim 4, wherein amino acid at amino acid position 865 is a polar amino acid or a glutamine before the mutation.

6. The avian coronavirus spike protein of claim 1, wherein the aromatic amino acid at amino acid position 865 is a histidine.

7. The avian coronavirus spike protein of claim 1, wherein the spike protein is within an avian coronavirus, and wherein the avian coronavirus is capable of infecting and/or replicating in at least one cell line selected from the list consisting of: DF-1 (Douglas Foster), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+ (*Spodoptera frugiperda*).

8. The avian coronavirus spike protein of claim 1, wherein the amino acid position 865 is within the S2 subunit of the spike protein.

9. The IBV spike protein of claim 3, wherein the spike protein is selected from a list of genotypes selected from the list of: GI-2 to 27, GII-1, GIII-1, GIV-1, GV-1, GVI-1.

10. The IBV spike protein of claim 3, wherein the spike protein is from an IBV with a genotype or serotype or a strain selected from the group consisting of: Arkansas, Brazil, California, Connecticut, Delaware, Dutch, Florida, Georgia, Gray, Holte, Iowa, Italy-02, JMK, LDT3, Maine, H52, H120, Pennsylvania, PL84084, Qu, QX, Q1, SE 17, Variant 2 and 4/91.

11. The IBV spike protein of claim 3, wherein the IBV spike protein consists of or comprises an amino acid sequence as shown in SEQ ID NO: 2, 3, 4, 5, 6, 7, 8 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto, and wherein the IBV spike protein contains the aromatic amino acid at position 865.

12. The avian coronavirus spike protein of claim 2, wherein the avian coronavirus or IBV with restricted cell or tissue tropism is restricted to infection and/or replication in embryonated chicken eggs and/or in primary chicken kidney cells.

13. A nucleotide sequence encoding the spike protein of claim 1.

14. A plasmid comprising the nucleotide sequence of claim 13.

15. A viral particle comprising the spike protein of claim 1.

16. An avian coronavirus comprising the spike protein of claim 1 or an IBV (infectious bronchitis virus) comprising the spike protein of claim 3.

17. The avian coronavirus or IBV of claim 16, wherein the avian coronavirus or IBV is attenuated.

18. An isolated cell comprising:
the plasmid of claim 14, or
the viral particle of claim 15, or
the avian coronavirus or IBV of claim 16.

19. An immunogenic composition comprising:
the spike protein of claim 1, or
the viral particle of claim 15, or
the avian coronavirus or IBV of claim 16.

20. A method for immunizing a subject comprising administering to the subject the immunogenic composition of claim 19.

21. A method of treating or preventing clinical signs caused by IBV in a subject of need, comprising administering to the subject a therapeutically effective amount of the immunogenic composition of claim 19.

22. A method of reducing the ciliostasis in a subject of need, in comparison to a subject of a non-immunized control group of the same species, the method comprises administering to the subject a therapeutically effective amount of the immunogenic composition of claim 19.

* * * * *

SEQUENCE LISTING

<160> NUMBER OF SEQ ID NOS: 31

<210> SEQ ID NO 1
<211> LENGTH: 1162
<212> TYPE: PRT
<213> ORGANISM: Avian infectious bronchitis virus

<400> SEQUENCE: 1

```
Met Leu Val Thr Pro Leu Leu Leu Val Thr Leu Leu Cys Ala Leu Cys
1               5                   10                  15

Ser Ala Ala Leu Tyr Asp Ser Ser Ser Tyr Val Tyr Tyr Tyr Gln Ser
                20                  25                  30

Ala Phe Arg Pro Pro Asp Gly Trp His Leu His Gly Gly Ala Tyr Ala
            35                  40                  45

Val Val Asn Ile Ser Ser Glu Ser Asn Asn Ala Gly Ser Ser Ser Gly
        50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala Tyr Cys Asn Phe Ser Asp Thr Thr Val Phe Val Thr
            100                 105                 110

His Cys Tyr Lys His Gly Gly Cys Pro Ile Thr Gly Met Leu Gln Gln
        115                 120                 125

His Ser Ile Arg Val Ser Ala Met Lys Asn Gly Gln Leu Phe Tyr Asn
    130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Glu Val Arg Ala Leu Ala
        195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
            245                 250                 255

Val Tyr Arg Glu Asn Ser Val Asn Thr Thr Phe Thr Leu His Asn Phe
            260                 265                 270
```

-continued

```
Thr Phe His Asn Glu Thr Gly Ala Asn Pro Asn Pro Ser Gly Val Gln
        275             280             285

Asn Ile Gln Thr Tyr Gln Thr Gln Thr Ala Gln Ser Gly Tyr Tyr Asn
    290             295             300

Phe Asn Phe Ser Phe Leu Ser Ser Phe Val Tyr Lys Glu Ser Asn Phe
305             310             315             320

Met Tyr Gly Ser Tyr His Pro Ser Cys Asn Phe Arg Leu Glu Thr Ile
            325             330             335

Asn Asn Gly Leu Trp Phe Asn Ser Leu Ser Val Ser Ile Ala Tyr Gly
            340             345             350

Pro Leu Gln Gly Gly Cys Lys Gln Ser Val Phe Ser Gly Arg Ala Thr
            355             360             365

Cys Cys Tyr Ala Tyr Ser Tyr Gly Gly Pro Leu Leu Cys Lys Gly Val
    370             375             380

Tyr Ser Gly Glu Leu Asp His Asn Phe Glu Cys Gly Leu Leu Val Tyr
385             390             395             400

Val Thr Lys Ser Gly Gly Ser Arg Ile Gln Thr Ala Thr Glu Pro Pro
            405             410             415

Val Ile Thr Gln His Asn Tyr Asn Asn Ile Thr Leu Asn Thr Cys Val
            420             425             430

Asp Tyr Asn Ile Tyr Gly Arg Thr Gly Gln Gly Phe Ile Thr Asn Val
            435             440             445

Thr Asp Ser Ala Val Ser Tyr Asn Tyr Leu Ala Asp Ala Gly Leu Ala
    450             455             460

Ile Leu Asp Thr Ser Gly Ser Ile Asp Ile Phe Val Val Gln Ser Glu
465             470             475             480

Tyr Gly Leu Asn Tyr Tyr Lys Val Asn Pro Cys Glu Asp Val Asn Gln
            485             490             495

Gln Phe Val Val Ser Gly Gly Lys Leu Val Gly Ile Leu Thr Ser Arg
            500             505             510

Asn Glu Thr Gly Ser Gln Leu Leu Glu Asn Gln Phe Tyr Ile Lys Ile
            515             520             525

Thr Asn Gly Thr Arg Arg Phe Arg Arg Ser Ile Thr Glu Ser Val Glu
    530             535             540

Asn Cys Pro Tyr Val Ser Tyr Gly Lys Phe Cys Ile Lys Pro Asp Gly
545             550             555             560

Ser Ile Ala Thr Ile Val Pro Lys Gln Leu Glu Gln Phe Val Ala Pro
            565             570             575

Leu Leu Asn Val Thr Glu Asn Val Leu Ile Pro Asn Ser Phe Asn Leu
            580             585             590

Thr Val Thr Asp Glu Tyr Ile Gln Thr Arg Met Asp Lys Val Gln Ile
            595             600             605

Asn Cys Leu Gln Tyr Ile Cys Gly Asn Ser Leu Glu Cys Arg Asn Leu
    610             615             620

Phe Gln Gln Tyr Gly Pro Val Cys Asp Asn Ile Leu Ser Val Val Asn
625             630             635             640

Ser Val Gly Gln Lys Glu Asp Met Glu Leu Leu Asn Phe Tyr Ser Ser
            645             650             655

Thr Lys Pro Ala Gly Phe Asn Thr Pro Val Leu Ser Asn Val Ser Thr
            660             665             670

Gly Glu Phe Asn Ile Thr Leu Phe Leu Thr Thr Pro Ser Ser Pro Arg
            675             680             685
```

-continued

```
Arg Arg Ser Phe Ile Glu Asp Leu Leu Phe Thr Ser Val Glu Ser Val
    690             695             700

Gly Leu Pro Thr Asp Asp Ala Tyr Lys Asn Cys Thr Ala Gly Pro Leu
705             710             715             720

Gly Phe Leu Lys Asp Leu Ala Cys Ala Arg Glu Tyr Asn Gly Leu Leu
            725             730             735

Val Leu Pro Pro Ile Ile Thr Ala Glu Met Gln Thr Leu Tyr Thr Ser
            740             745             750

Ser Leu Val Ala Ser Met Ala Phe Gly Gly Ile Thr Ala Ala Gly Ala
            755             760             765

Ile Pro Phe Ala Thr Gln Leu Gln Ala Arg Ile Asn His Leu Gly Ile
    770             775             780

Thr Gln Ser Leu Leu Leu Lys Asn Gln Glu Lys Ile Ala Ala Ser Phe
785             790             795             800

Asn Lys Ala Ile Gly His Met Gln Glu Gly Phe Arg Ser Thr Ser Leu
            805             810             815

Ala Leu Gln Gln Ile Gln Asp Val Val Asn Lys Gln Ser Ala Ile Leu
            820             825             830

Thr Glu Thr Met Ala Ser Leu Asn Lys Asn Phe Gly Ala Ile Ser Ser
            835             840             845

Val Ile Gln Glu Ile Tyr Gln Gln Leu Asp Ala Ile Gln Ala Asn Ala
    850             855             860

Gln Val Asp Arg Leu Ile Thr Gly Arg Leu Ser Ser Leu Ser Val Leu
865             870             875             880

Ala Ser Ala Lys Gln Ala Glu Tyr Ile Arg Val Ser Gln Gln Arg Glu
            885             890             895

Leu Ala Thr Gln Lys Ile Asn Glu Cys Val Lys Ser Gln Ser Ile Arg
            900             905             910

Tyr Ser Phe Cys Gly Asn Gly Arg His Val Leu Thr Ile Pro Gln Asn
            915             920             925

Ala Pro Asn Gly Ile Val Phe Ile His Phe Ser Tyr Thr Pro Asp Ser
    930             935             940

Phe Val Asn Val Thr Ala Ile Val Gly Phe Cys Val Lys Pro Ala Asn
945             950             955             960

Ala Ser Gln Tyr Ala Ile Val Pro Ala Asn Gly Arg Gly Ile Phe Ile
            965             970             975

Gln Val Asn Gly Ser Tyr Tyr Ile Thr Ala Arg Asp Met Tyr Met Pro
            980             985             990

Arg Ala Ile Thr Ala Gly Asp Ile Val Thr Leu Thr Ser Cys Gln Ala
            995             1000            1005

Asn Tyr Val Ser Val Asn Lys Thr Val Ile Thr Thr Phe Val Asp
    1010            1015            1020

Asn Asp Asp Phe Asp Phe Asn Asp Glu Leu Ser Lys Trp Trp Asn
    1025            1030            1035

Asp Thr Lys His Glu Leu Pro Asp Phe Asp Lys Phe Asn Tyr Thr
    1040            1045            1050

Val Pro Ile Leu Asp Ile Asp Ser Glu Ile Asp Arg Ile Gln Gly
    1055            1060            1065

Val Ile Gln Gly Leu Asn Asp Ser Leu Ile Asp Leu Glu Lys Leu
    1070            1075            1080

Ser Ile Leu Lys Thr Tyr Ile Lys Trp Pro Trp Tyr Val Trp Leu
    1085            1090            1095

Ala Ile Ala Phe Ala Thr Ile Ile Phe Ile Leu Ile Leu Gly Trp
```

-continued

```
        1100            1105            1110

Val Phe  Phe Met Thr Gly Cys  Cys Gly Cys Cys Cys  Gly Cys Phe
    1115            1120            1125

Gly Ile  Met Pro Leu Met Ser  Lys Cys Gly Lys Lys  Ser Ser Tyr
    1130            1135            1140

Tyr Thr  Thr Phe Asp Asn Asp  Val Val Thr Glu Gln  Tyr Arg Pro
    1145            1150            1155

Lys Lys  Ser Val
    1160
```

<210> SEQ ID NO 2
<211> LENGTH: 1162
<212> TYPE: PRT
<213> ORGANISM: Avian infectious bronchitis virus

<400> SEQUENCE: 2

```
Met Leu Val Thr Pro Leu Leu Leu Val Thr Leu Leu Cys Ala Leu Cys
1               5                   10                  15

Ser Ala Ala Leu Tyr Asp Ser Ser Ser Tyr Val Tyr Tyr Gln Ser
                20                  25                  30

Ala Phe Arg Pro Pro Asp Gly Trp His Leu His Gly Gly Ala Tyr Ala
            35                  40                  45

Val Val Asn Ile Ser Ser Glu Ser Asn Asn Ala Gly Ser Ser Ser Gly
        50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala Tyr Cys Asn Phe Ser Asp Thr Thr Val Phe Val Thr
            100                 105                 110

His Cys Tyr Lys His Gly Gly Cys Pro Ile Thr Gly Met Leu Gln Gln
            115                 120                 125

His Ser Ile Arg Val Ser Ala Met Lys Asn Gly Gln Leu Phe Tyr Asn
        130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Glu Val Arg Ala Leu Ala
            195                 200                 205

Tyr Phe Val Asn Gly Thr Ala Gln Asp Val Ile Leu Cys Asp Gly Ser
        210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270

Thr Phe His Asn Glu Thr Gly Ala Asn Pro Asn Pro Ser Gly Val Gln
        275                 280                 285

Asn Ile Gln Thr Tyr Gln Thr Gln Thr Ala Gln Ser Gly Tyr Tyr Asn
        290                 295                 300
```

-continued

```
Phe Asn Phe Ser Phe Leu Ser Ser Phe Val Tyr Lys Glu Ser Asn Phe
305             310             315             320

Met Tyr Gly Ser Tyr His Pro Ser Cys Asn Phe Arg Leu Glu Thr Ile
            325             330             335

Asn Asn Gly Leu Trp Phe Asn Ser Leu Ser Val Ser Ile Ala Tyr Gly
            340             345             350

Pro Leu Gln Gly Gly Cys Lys Gln Ser Val Phe Ser Gly Arg Ala Thr
            355             360             365

Cys Cys Tyr Ala Tyr Ser Tyr Gly Gly Pro Leu Leu Cys Lys Gly Val
    370             375             380

Tyr Ser Gly Glu Leu Asp His Asn Phe Glu Cys Gly Leu Leu Val Tyr
385             390             395             400

Val Thr Lys Ser Gly Gly Ser Arg Ile Gln Thr Ala Thr Glu Pro Pro
            405             410             415

Val Ile Thr Gln His Asn Tyr Asn Asn Ile Thr Leu Asn Thr Cys Val
            420             425             430

Asp Tyr Asn Ile Tyr Gly Arg Thr Gly Gln Gly Phe Ile Thr Asn Val
            435             440             445

Thr Asp Ser Ala Val Ser Tyr Asn Tyr Leu Ala Asp Ala Gly Leu Ala
    450             455             460

Ile Leu Asp Thr Ser Gly Ser Ile Asp Ile Phe Val Val Gln Ser Glu
465             470             475             480

Tyr Gly Leu Asn Tyr Tyr Lys Val Asn Pro Cys Glu Asp Val Asn Gln
            485             490             495

Gln Phe Val Val Ser Gly Gly Lys Leu Val Gly Ile Leu Thr Ser Arg
            500             505             510

Asn Glu Thr Gly Ser Gln Leu Leu Glu Asn Gln Phe Tyr Ile Lys Ile
            515             520             525

Thr Asn Gly Thr Arg Arg Phe Arg Arg Ser Ile Thr Glu Ser Val Glu
    530             535             540

Asn Cys Pro Tyr Val Ser Tyr Gly Lys Phe Cys Ile Lys Pro Asp Gly
545             550             555             560

Ser Ile Ala Thr Ile Val Pro Lys Gln Leu Glu Gln Phe Val Ala Pro
            565             570             575

Leu Leu Asn Val Thr Glu Asn Val Leu Ile Pro Asn Ser Phe Asn Leu
            580             585             590

Thr Val Thr Asp Glu Tyr Ile Gln Thr Arg Met Asp Lys Val Gln Ile
            595             600             605

Asn Cys Leu Gln Tyr Ile Cys Gly Asn Ser Leu Glu Cys Arg Asn Leu
    610             615             620

Phe Gln Gln Tyr Gly Pro Val Cys Asp Asn Ile Leu Ser Val Val Asn
625             630             635             640

Ser Val Gly Gln Lys Glu Asp Met Glu Leu Leu Asn Phe Tyr Ser Ser
            645             650             655

Thr Lys Pro Ala Gly Phe Asn Thr Pro Val Leu Ser Asn Val Ser Thr
            660             665             670

Gly Glu Phe Asn Ile Thr Leu Phe Leu Thr Thr Pro Ser Ser Pro Arg
            675             680             685

Arg Arg Ser Phe Ile Glu Asp Leu Leu Phe Thr Ser Val Glu Ser Val
    690             695             700

Gly Leu Pro Thr Asp Asp Ala Tyr Lys Asn Cys Thr Ala Gly Pro Leu
705             710             715             720

Gly Phe Leu Lys Asp Leu Ala Cys Ala Arg Glu Tyr Asn Gly Leu Leu
```

-continued

```
                725                     730                     735

Val Leu Pro Pro Ile Ile Thr Ala Glu Met Gln Thr Leu Tyr Thr Ser
            740                     745                     750

Ser Leu Val Ala Ser Met Ala Phe Gly Gly Ile Thr Ala Ala Gly Ala
            755                     760                     765

Ile Pro Phe Ala Thr Gln Leu Gln Ala Arg Ile Asn His Leu Gly Ile
    770                     775                     780

Thr Gln Ser Leu Leu Leu Lys Asn Gln Glu Lys Ile Ala Ala Ser Phe
785                     790                     795                     800

Asn Lys Ala Ile Gly His Met Gln Glu Gly Phe Arg Ser Thr Ser Leu
                805                     810                     815

Ala Leu Gln Gln Ile Gln Asp Val Val Asn Lys Gln Ser Ala Ile Leu
            820                     825                     830

Thr Glu Thr Met Ala Ser Leu Asn Lys Asn Phe Gly Ala Ile Ser Ser
            835                     840                     845

Val Ile Gln Glu Ile Tyr Gln Gln Leu Asp Ala Ile Gln Ala Asn Ala
    850                     855                     860

His Val Asp Arg Leu Ile Thr Gly Arg Leu Ser Ser Leu Ser Val Leu
865                     870                     875                     880

Ala Ser Ala Lys Gln Ala Glu Tyr Ile Arg Val Ser Gln Gln Arg Glu
                885                     890                     895

Leu Ala Thr Gln Lys Ile Asn Glu Cys Val Lys Ser Gln Ser Ile Arg
            900                     905                     910

Tyr Ser Phe Cys Gly Asn Gly Arg His Val Leu Thr Ile Pro Gln Asn
            915                     920                     925

Ala Pro Asn Gly Ile Val Phe Ile His Phe Ser Tyr Thr Pro Asp Ser
    930                     935                     940

Phe Val Asn Val Thr Ala Ile Val Gly Phe Cys Val Lys Pro Ala Asn
945                     950                     955                     960

Ala Ser Gln Tyr Ala Ile Val Pro Ala Asn Gly Arg Gly Ile Phe Ile
                965                     970                     975

Gln Val Asn Gly Ser Tyr Tyr Ile Thr Ala Arg Asp Met Tyr Met Pro
            980                     985                     990

Arg Ala Ile Thr Ala Gly Asp Ile  Val Thr Leu Thr Ser  Cys Gln Ala
            995                     1000                    1005

Asn Tyr  Val Ser Val Asn Lys  Thr Val Ile Thr Thr  Phe Val Asp
    1010                    1015                    1020

Asn Asp  Asp Phe Asp Phe Asn  Asp Glu Leu Ser Lys  Trp Trp Asn
    1025                    1030                    1035

Asp Thr  Lys His Glu Leu Pro  Asp Phe Asp Lys Phe  Asn Tyr Thr
    1040                    1045                    1050

Val Pro  Ile Leu Asp Ile Asp  Ser Glu Ile Asp Arg  Ile Gln Gly
    1055                    1060                    1065

Val Ile  Gln Gly Leu Asn Asp  Ser Leu Ile Asp Leu  Glu Lys Leu
    1070                    1075                    1080

Ser Ile  Leu Lys Thr Tyr Ile  Lys Trp Pro Trp Tyr  Val Trp Leu
    1085                    1090                    1095

Ala Ile  Ala Phe Ala Thr Ile  Ile Phe Ile Leu Ile  Leu Gly Trp
    1100                    1105                    1110

Val Phe  Phe Met Thr Gly Cys  Cys Gly Cys Cys Cys  Gly Cys Phe
    1115                    1120                    1125

Gly Ile  Met Pro Leu Met Ser  Lys Cys Gly Lys Lys  Ser Ser Tyr
    1130                    1135                    1140
```

-continued

```
Tyr Thr  Thr Phe Asp Asn Asp  Val Val Thr Glu Gln  Tyr Arg Pro
    1145             1150             1155

Lys Lys  Ser Val
    1160

<210> SEQ ID NO 3
<211> LENGTH: 1155
<212> TYPE: PRT
<213> ORGANISM: Avian infectious bronchitis virus

<400> SEQUENCE: 3

Met Leu Asp Lys Pro Leu Leu Leu Val Thr Leu Trp Tyr Ala Leu Cys
1               5                   10                  15

Ser Ala Leu Leu Tyr Asp Asn Asn Thr Tyr Val Tyr Tyr Tyr Gln Ser
            20                  25                  30

Ala Phe Arg Pro Gly Pro Gly Trp His Leu Tyr Gly Gly Ala Tyr Ala
        35                  40                  45

Val Asp Arg Val Phe Asn Glu Thr Asn Asn Ala Gly Ser Ala Ser Asp
    50                  55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
                100                 105                 110

His Cys Phe Lys Asn Gln Leu Gly Ser Cys Pro Leu Thr Gly Met Ile
        115                 120                 125

Pro Gln Asn His Ile Arg Ile Ser Ala Met Arg Asp Gly Val Leu Phe
    130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
                180                 185                 190

Lys Ser Gly Gly Pro Val Thr Tyr Lys Val Met Lys Glu Val Lys Ala
        195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Leu Lys Leu Thr
                260                 265                 270

Asn Phe Ser Phe Thr Asn Val Ser Asn Ala Ser Pro Asn Ser Gly Gly
        275                 280                 285

Val Asp Thr Phe Gln Leu Tyr Gln Thr Ser Thr Ala Gln Asp Gly Tyr
    290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr
```

```
                340                  345                  350

Tyr Gly Pro Ile Gln Gly Gly Cys Lys Gln Ser Val Phe Ser Asn Arg
        355                  360                  365

Ala Thr Cys Cys Tyr Ala Tyr Ser Tyr Gln Gly Pro Ser Arg Cys Lys
        370                  375                  380

Gly Val Tyr Arg Gly Glu Leu Thr Gln Tyr Phe Glu Cys Gly Leu Leu
385                  390                  395                  400

Val Tyr Val Thr Lys Ser Asp Gly Ser Arg Ile Gln Thr Arg Ser Glu
                405                  410                  415

Pro Leu Val Leu Thr Gln Tyr Asn Tyr Asn Asn Ile Thr Leu Asn Lys
                420                  425                  430

Cys Val Glu Tyr Asn Ile Tyr Gly Arg Val Gly Gln Gly Phe Ile Thr
                435                  440                  445

Asn Val Thr Glu Ala Thr Ala Asn Tyr Ser Tyr Leu Ala Asp Gly Gly
                450                  455                  460

Leu Ala Ile Leu Asp Thr Ser Gly Ala Ile Asp Ile Phe Val Val Gln
465                  470                  475                  480

Gly Ala Tyr Gly Leu Asn Tyr Tyr Lys Val Asn Pro Cys Glu Asp Val
                485                  490                  495

Asn Gln Gln Phe Val Val Ser Gly Gly Asn Leu Val Gly Ile Leu Thr
                500                  505                  510

Ser His Asn Glu Thr Gly Ser Glu Ser Ile Glu Asn Gln Phe Tyr Ile
                515                  520                  525

Lys Leu Thr Asn Gly Thr Arg Arg Ser Arg Arg Ser Val Thr Gly Asn
        530                  535                  540

Val Thr Asn Cys Pro Tyr Val Ser Tyr Gly Lys Phe Cys Ile Lys Pro
545                  550                  555                  560

Asp Gly Ser Leu Ser Ile Ile Val Pro Gln Glu Leu Glu Gln Phe Val
                565                  570                  575

Ala Pro Leu Phe Asn Val Thr Glu His Val Leu Ile Pro Asp Ser Phe
                580                  585                  590

Asn Leu Thr Val Thr Asp Glu Tyr Ile Gln Thr Arg Met Asp Lys Val
                595                  600                  605

Gln Ile Ile Cys Leu Gln Tyr Val Cys Gly Asn Ser Ile Glu Cys Arg
        610                  615                  620

Lys Leu Phe Gln Gln Tyr Gly Pro Val Cys Asp Asn Ile Leu Ser Val
625                  630                  635                  640

Val Asn Gly Val Gly Gln Arg Glu Asp Met Glu Leu Leu Ser Phe Tyr
                645                  650                  655

Ser Ser Thr Lys Pro Ser Gly Tyr Asn Thr Pro Ile Phe Asn Asn Val
                660                  665                  670

Ser Thr Gly Asp Phe Asn Ile Ser Leu Leu Leu Thr Pro Pro Asn Ser
                675                  680                  685

Pro Thr Gly Arg Ser Phe Ile Glu Asp Leu Leu Phe Thr Ser Val Glu
        690                  695                  700

Ser Val Gly Leu Pro Thr Asp Glu Glu Tyr Lys Lys Cys Thr Ala Gly
705                  710                  715                  720

Pro Leu Gly Phe Val Lys Asp Leu Val Cys Ala Arg Glu Tyr Asn Gly
                725                  730                  735

Leu Leu Val Leu Pro Pro Ile Ile Thr Ala Glu Met Gln Thr Met Tyr
                740                  745                  750

Thr Ser Ser Leu Val Ala Ser Met Ala Leu Gly Gly Ile Thr Ala Ala
        755                  760                  765
```

Gly Ala Ile Pro Phe Ala Thr Gln Leu Gln Ala Arg Ile Asn His Leu
    770                 775                 780

Gly Ile Thr Asn Ser Leu Leu Leu Lys Asn Gln Glu Lys Ile Ala Ala
785                 790                 795                 800

Ser Phe Asn Lys Ala Ile Gly His Met Gln Glu Gly Phe Lys Ser Thr
                805                 810                 815

Ser Leu Ala Leu Gln Gln Ile Gln Asp Val Val Asn Lys Gln Ser Ser
                820                 825                 830

Ile Leu Thr Glu Thr Met Gln Ser Leu Asn Lys Asn Phe Gly Ala Ile
            835                 840                 845

Ser Ser Val Ile Gln Asp Ile Tyr Gln Gln Leu Asp Ala Ile Gln Ala
    850                 855                 860

Asp Ala His Val Asp Arg Leu Ile Thr Gly Arg Leu Ser Ser Leu Ser
865                 870                 875                 880

Val Leu Ala Ser Ala Lys Gln Ala Glu Tyr His Arg Val Ser Gln Gln
                885                 890                 895

Arg Glu Leu Ala Thr Gln Lys Ile Asn Glu Cys Val Lys Ser Gln Ser
                900                 905                 910

Asn Arg Tyr Ser Phe Cys Gly Asn Gly Arg His Val Leu Thr Ile Pro
        915                 920                 925

Gln Asn Ala Pro Asn Gly Ile Val Phe Ile His Phe Thr Tyr Thr Pro
    930                 935                 940

Glu Ser Phe Val Asn Val Thr Ala Ile Val Gly Phe Cys Val Asn Pro
945                 950                 955                 960

Ala Asn Ala Ser His Tyr Ala Ile Val Pro Val Asn Gly Arg Gly Val
                965                 970                 975

Phe Ile Glu Val Asn Gly Ser Tyr Tyr Ile Thr Ala Arg Asp Met Tyr
            980                 985                 990

Met Pro Arg Asp Ile Thr Ala Gly  Asp Ile Val Thr Leu  Thr Ser Cys
        995                 1000                1005

Gln Ala  Asn Tyr Val Asn Val  Asn Lys Thr Val Ile  Asn Thr Phe
    1010                1015                1020

Val Glu  Asp Asp Asp Phe Asp  Phe Tyr Asp Glu Leu  Ser Lys Trp
    1025                1030                1035

Trp Asn  Asp Thr Lys His Glu  Leu Pro Asp Phe Asp  Glu Phe Asn
    1040                1045                1050

Tyr Thr  Val Pro Val Leu Asn  Ile Ser Asn Glu Ile  Asp Arg Ile
    1055                1060                1065

Gln Gln  Val Ile Gln Gly Leu  Asn Asp Ser Leu Ile  Asp Leu Glu
    1070                1075                1080

Thr Leu  Ser Ile Leu Lys Thr  Tyr Ile Lys Trp Pro  Trp Tyr Val
    1085                1090                1095

Trp Leu  Ala Ile Ala Phe Leu  Thr Ile Ile Phe Ile  Leu Val Leu
    1100                1105                1110

Cys Trp  Ile Phe Phe Met Thr  Gly Cys Cys Gly Cys  Cys Cys Gly
    1115                1120                1125

Cys Phe  Gly Ile Ile Pro Leu  Met Ser Lys Cys Gly  Lys Lys Ser
    1130                1135                1140

Ser Tyr  Tyr Thr Thr Phe Asp  Asn Asp Val Val Thr
    1145                1150                1155

<210> SEQ ID NO 4
<211> LENGTH: 1156

```
<212> TYPE: PRT
<213> ORGANISM: Avian infectious bronchitis virus

<400> SEQUENCE: 4

Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
            35                  40                  45

Ala Val Val Ser Ser Thr Asn Tyr Thr Asn Asn Ala Gly Ser Ala His
        50                  55                  60

Gly Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
            115                 120                 125

Ile Pro Arg Asp His Ile Arg Ile Ser Ala Met Lys Asn Gly Ser Leu
            130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
                180                 185                 190

Phe Lys Ala Gly Gly Pro Val Asn Tyr Ser Ile Met Lys Glu Phe Lys
            195                 200                 205

Val Leu Ala Tyr Phe Val Asn Gly Thr Ala Gln Asp Val Val Leu Cys
            210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Leu Ala Leu
            260                 265                 270

Thr Asn Phe Thr Phe Ser Asn Val Ser Asn Ala Gln Pro Asn Ser Gly
            275                 280                 285

Gly Val Asn Thr Phe His Leu Tyr Gln Thr Gln Thr Ala Gln Ser Gly
        290                 295                 300

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
            340                 345                 350

Thr Tyr Gly Pro Leu Gln Gly Gly Cys Lys Gln Ser Val Phe Ser Gly
            355                 360                 365

Lys Ala Thr Cys Cys Tyr Ala Tyr Ser Tyr Arg Gly Pro Met Ala Cys
            370                 375                 380

Lys Gly Val Tyr Ser Gly Glu Leu Ser Thr Asn Phe Glu Cys Gly Leu
385                 390                 395                 400
```

-continued

```
Leu Val Tyr Val Thr Lys Ser Asp Gly Ser Arg Ile Gln Thr Arg Thr
                405             410             415

Glu Pro Leu Val Leu Thr Gln Tyr Asn Tyr Asn Asn Ile Thr Leu Asp
                420             425             430

Lys Cys Val Ala Tyr Asn Ile Tyr Gly Arg Val Gly Gln Gly Phe Ile
                435             440             445

Thr Asn Val Thr Asp Ser Ala Ala Asn Phe Ser Tyr Leu Ala Asp Gly
        450             455             460

Gly Leu Ala Ile Leu Asp Thr Ser Gly Ala Ile Asp Val Phe Val Val
465             470             475             480

Gln Gly Ile Tyr Gly Leu Asn Tyr Tyr Lys Val Asn Pro Cys Glu Asp
                485             490             495

Val Asn Gln Gln Phe Val Val Ser Gly Gly Asn Ile Val Gly Ile Leu
            500             505             510

Thr Ser Arg Asn Glu Thr Gly Ser Glu Gln Val Glu Asn Gln Phe Tyr
        515             520             525

Val Lys Leu Thr Asn Ser Ser His Arg Arg Lys Arg Ser Ile Gly Gln
    530             535             540

Asn Val Thr Ser Cys Pro Tyr Val Ser Tyr Gly Arg Phe Cys Ile Glu
545             550             555             560

Pro Asp Gly Ser Leu Lys Met Ile Val Pro Glu Glu Leu Lys Gln Phe
                565             570             575

Val Ala Pro Leu Leu Asn Ile Thr Glu Ser Val Leu Ile Pro Asn Ser
            580             585             590

Phe Asn Leu Thr Val Thr Asp Glu Tyr Ile Gln Thr Arg Met Asp Lys
        595             600             605

Val Gln Ile Asn Cys Leu Gln Tyr Val Cys Gly Asn Ser Leu Glu Cys
    610             615             620

Arg Lys Leu Phe Gln Gln Tyr Gly Pro Val Cys Asp Asn Ile Leu Ser
625             630             635             640

Val Val Asn Ser Val Ser Gln Lys Glu Asp Met Glu Leu Leu Ser Phe
            645             650             655

Tyr Ser Ser Thr Lys Pro Lys Gly Tyr Asp Thr Pro Val Leu Ser Asn
            660             665             670

Val Ser Thr Gly Glu Phe Asn Ile Ser Leu Leu Leu Lys Pro Pro Ser
        675             680             685

Ser Pro Ser Gly Arg Ser Phe Ile Glu Glu Leu Leu Phe Thr Ser Val
        690             695             700

Glu Thr Val Gly Leu Pro Thr Asp Ala Glu Tyr Lys Lys Cys Thr Ala
705             710             715             720

Gly Pro Leu Gly Thr Leu Lys Asp Leu Ile Cys Ala Arg Glu Tyr Asn
            725             730             735

Gly Leu Leu Val Leu Pro Pro Ile Ile Thr Ala Asp Met Gln Thr Met
            740             745             750

Tyr Thr Ala Ser Leu Val Gly Ala Met Ala Phe Gly Gly Ile Thr Ser
        755             760             765

Ala Ala Ala Ile Pro Phe Ala Thr Gln Ile Gln Ala Arg Ile Asn His
        770             775             780

Leu Gly Ile Thr Gln Ser Leu Leu Met Lys Asn Gln Glu Lys Ile Ala
785             790             795             800

Ala Ser Phe Asn Lys Ala Ile Gly His Met Gln Glu Gly Phe Arg Ser
                805             810             815
```

-continued

```
Thr Ser Leu Ala Leu Gln Gln Ile Gln Asp Val Val Asn Lys Gln Ser
            820                 825                 830

Ala Ile Leu Thr Glu Thr Met Asn Ser Leu Asn Lys Asn Phe Gly Ala
            835                 840                 845

Ile Thr Ser Val Ile Gln Asp Ile Tyr Ala Gln Leu Asp Ala Ile Gln
            850                 855                 860

Ala Asp Ala His Val Asp Arg Leu Ile Thr Gly Arg Leu Ser Ser Leu
865                 870                 875                 880

Ser Val Leu Ala Ser Ala Lys Gln Ser Glu Tyr Ile Arg Val Ser Gln
                885                 890                 895

Gln Arg Glu Leu Ala Thr Gln Lys Ile Asn Glu Cys Val Lys Ser Gln
            900                 905                 910

Ser Asn Arg Tyr Gly Phe Cys Gly Ser Gly Arg His Val Leu Ser Ile
            915                 920                 925

Pro Gln Asn Ala Pro Asn Gly Ile Val Phe Ile His Phe Thr Tyr Thr
    930                 935                 940

Pro Glu Ser Phe Val Asn Val Thr Ala Ile Val Gly Phe Cys Val Asn
945                 950                 955                 960

Pro Ala Asn Ala Ser Gln Tyr Ala Ile Val Pro Ala Asn Gly Arg Gly
                965                 970                 975

Ile Phe Ile Gln Val Asn Gly Thr Tyr Tyr Ile Thr Ala Arg Asp Met
            980                 985                 990

Tyr Met Pro Arg Asp Ile Thr Ala  Gly Asp Ile Val Thr  Leu Thr Ser
            995                 1000                1005

Cys Gln  Ala Asn Tyr Val Asn  Val Asn Lys Thr Val  Ile Thr Thr
    1010                1015                1020

Phe Val  Glu Asp Asp Asp Phe  Asp Phe Asp Asp Glu  Leu Ser Lys
    1025                1030                1035

Trp Trp  Asn Asp Thr Lys His  Gln Leu Pro Asp Phe  Asp Asp Phe
    1040                1045                1050

Asn Tyr  Thr Val Pro Ile Leu  Asn Ile Ser Gly Glu  Ile Asp Tyr
    1055                1060                1065

Ile Gln  Gly Val Ile Gln Gly  Leu Asn Asp Ser Leu  Ile Asp Leu
    1070                1075                1080

Glu Glu  Leu Ser Ile Ile Lys  Thr Tyr Ile Lys Trp  Pro Trp Tyr
    1085                1090                1095

Val Trp  Leu Ala Ile Phe Phe  Ala Ile Ile Ile Phe  Ile Leu Ile
    1100                1105                1110

Leu Gly  Trp Val Phe Phe Met  Thr Gly Cys Cys Gly  Cys Cys Cys
    1115                1120                1125

Gly Cys  Phe Gly Ile Ile Pro  Leu Met Ser Lys Cys  Gly Lys Lys
    1130                1135                1140

Ser Ser  Tyr Tyr Thr Thr Phe  Asp Asn Asp Val Val  Thr
    1145                1150                1155
```

```
<210> SEQ ID NO 5
<211> LENGTH: 1156
<212> TYPE: PRT
<213> ORGANISM: Avian infectious bronchitis virus

<400> SEQUENCE: 5

Met Leu Gly Lys Ser Leu Phe Val Val Thr Leu Leu Phe Ala Leu Cys
1               5                   10                  15

Ser Ala Ala Leu Phe Asp Asn Asn Glu Thr Val Tyr Tyr Tyr Gln Ser
            20                  25                  30
```

```
Ala Phe Arg Pro Ala Asp Gly Trp His Leu His Gly Gly Ala Tyr Ala
        35              40              45

Val Val Asn Val Ser Leu Gln Thr Ser Asn Ala Gly Thr Val Ser Glu
        50              55              60

Cys Ile Ala Gly Ala Ile Ser Trp Ser Lys Glu Phe Ser Ala Ser Ala
65              70              75              80

Val Ala Met Thr Ala Pro Gln Leu Gly Met Thr Trp Ser Thr Arg Gln
            85              90              95

Phe Cys Thr Ala His Cys Asn Phe Ser Asp Phe Thr Val Phe Val Thr
            100             105             110

His Cys Phe Lys His Gly Thr Gly Leu Cys Pro Leu Thr Gly Phe Ile
        115             120             125

Pro Ser Gly Phe Ile Arg Val Ser Ala Met Arg Lys Gly Ser Asn Ser
        130             135             140

Leu Phe Tyr Asn Leu Thr Val Ser Val Thr Lys Tyr Pro Arg Phe Lys
145             150             155             160

Ser Leu Gln Cys Val Asn Asn Tyr Thr Ser Val Tyr Leu Asn Gly Asp
            165             170             175

Leu Val Phe Thr Ser Asn Glu Thr Lys Pro Val Ser Ala Ala Gly Val
            180             185             190

Ser Phe Lys Ala Gly Gly Pro Ile Thr Tyr Lys Ile Met Asn Glu Val
            195             200             205

Lys Val Leu Ala Tyr Phe Val Asn Gly Thr Ala Gln Thr Val Ile Pro
        210             215             220

Cys Asp Gly Ser Pro Arg Gly Leu Leu Ala Cys Gln Tyr Asn Thr Gly
225             230             235             240

Asn Phe Ser Asp Gly Phe Tyr Pro Tyr Thr Asn Ser Ser Leu Val Lys
            245             250             255

Glu Arg Phe Ile Val Tyr Arg Glu Ser Ser Val Asn Thr Ile Leu Val
            260             265             270

Leu Thr Asn Phe Thr Phe Ser Asn Val Ser Asn Ala Leu Pro Asn Thr
        275             280             285

Gly Asn Val His Ser Ile Val Leu His Gln Thr Gln Thr Ala Gln Ser
        290             295             300

Gly Tyr Tyr Asn Leu Asn Phe Ser Phe Leu Ser Gly Phe Arg Tyr Val
305             310             315             320

Glu Ser Asp Phe Met Tyr Gly Ser Tyr His Pro Lys Cys Ser Phe Arg
            325             330             335

Pro Glu Thr Ile Asn Asn Gly Leu Trp Phe Asn Ser Leu Ser Val Ser
            340             345             350

Leu Gly Tyr Gly Pro Leu Gln Gly Gly Cys Lys Gln Ser Val Phe Asn
        355             360             365

Asn Lys Ala Thr Cys Cys Tyr Ala Tyr Ser Tyr Asn Gly Pro Thr Leu
        370             375             380

Cys Lys Gly Val Tyr Ser Gly Glu Leu Gln Lys Thr Phe Glu Cys Gly
385             390             395             400

Leu Leu Val Phe Val Thr Lys Ser Asp Gly Ser Arg Ile Gln Thr Arg
            405             410             415

Asn Glu Pro Leu Val Leu Thr Gln His Asn Tyr Asn Asn Ile Thr Leu
        420             425             430

Asn Lys Cys Val Glu Tyr Asn Ile Tyr Gly Arg Val Gly Gln Gly Leu
        435             440             445
```

-continued

```
Ile Thr Asn Ile Thr Asp Ser Ala Ala Asn His Gly Tyr Leu Ala Asp
    450                 455                 460

Gly Gly Leu Ala Val Leu Asp Thr Ser Gly Ala Ile Asp Val Phe Val
465                 470                 475                 480

Val Gln Gly Val Tyr Gly Leu Asn Tyr Tyr Lys Val Asn Pro Cys Glu
                485                 490                 495

Asp Val Asn Gln Gln Phe Val Val Ser Gly Gly Gln Leu Val Gly Ile
                500                 505                 510

Leu Thr Ser Arg Asn Glu Thr Gly Ser Gln Pro Ile Glu Asn Arg Phe
                515                 520                 525

Tyr Val Lys Phe Ser Asn Ser Arg Arg Arg Thr Gly Arg Ser Thr Ile
    530                 535                 540

Ala Asn Val Thr Asn Cys Pro Tyr Val Ser Tyr Gly Lys Phe Cys Ile
545                 550                 555                 560

Lys Pro Asp Gly Ser Val Leu Glu Ile Val Pro Gln Glu Ile Glu His
                565                 570                 575

Phe Val Ala Pro Leu Leu Asn Val Thr Glu His Val Leu Ile Pro Asn
                580                 585                 590

Ser Phe Asn Leu Thr Val Thr Asp Glu Tyr Ile Gln Thr Arg Met Asp
    595                 600                 605

Lys Ile Gln Ile Asn Cys Leu Gln Tyr Val Cys Gly Asn Ser Ile Glu
    610                 615                 620

Cys Arg Lys Leu Phe Gln Gln Tyr Gly Pro Val Cys Asp Asn Ile Leu
625                 630                 635                 640

Ser Val Val Asn Thr Val Gly Gln Arg Glu Asp Met Glu Leu Leu Ser
                645                 650                 655

Phe Tyr Ser Ser Thr Lys Pro Lys Asp Tyr Asn Val Pro Ile Phe Ser
                660                 665                 670

Asn Val Ser Thr Gly Asp Phe Asn Ile Ser Leu Leu Leu Thr Pro Pro
                675                 680                 685

Asn Ser Pro Thr Gly Arg Ser Phe Ile Glu Asp Ile Leu Phe Thr Ser
    690                 695                 700

Val Glu Ser Val Gly Leu Pro Thr Asp Glu Glu Tyr Lys Lys Cys Thr
705                 710                 715                 720

Ala Gly Pro Leu Gly Phe Val Lys Asp Leu Val Cys Ala Arg Glu Tyr
                725                 730                 735

Asn Gly Leu Leu Val Leu Pro Pro Ile Ile Thr Ala Asp Met Gln Thr
                740                 745                 750

Met Tyr Thr Ser Thr Leu Val Ala Ser Met Ala Leu Gly Gly Ile Thr
    755                 760                 765

Ala Ala Gly Ala Ile Pro Phe Ala Thr Gln Leu Gln Ala Arg Ile Asn
    770                 775                 780

His Leu Gly Ile Thr Gln Ser Leu Leu Leu Lys Asn Gln Glu Lys Ile
785                 790                 795                 800

Ala Ala Ser Phe Asn Lys Ala Ile Gly His Met Gln Glu Gly Phe Arg
                805                 810                 815

Ser Thr Ser Leu Ala Leu Gln Gln Ile Gln Asp Val Val Asn Lys Gln
                820                 825                 830

Ser Ser Ile Leu Thr Glu Thr Met Ala Ser Leu Asn Lys Asn Phe Gly
                835                 840                 845

Ala Ile Ser Ser Val Leu Gln Asp Ile Tyr Gln Gln Leu Asp Ala Ile
    850                 855                 860

Gln Ala Asp Ala His Val Asp Arg Ile Ile Thr Gly Arg Leu Ser Ser
```

-continued

```
865              870              875              880
Leu Ser Val Leu Ala Ser Ala Lys Gln Ser Glu Tyr Tyr Arg Val Ser
                 885              890              895

Gln Gln Arg Glu Leu Ala Thr Gln Lys Ile Asn Glu Cys Val Lys Ser
             900              905              910

Gln Ser Thr Arg Tyr Ser Phe Cys Gly Asn Gly Arg His Val Leu Thr
             915              920              925

Ile Pro Gln Asn Ala Pro Asn Gly Ile Val Phe Ile His Phe Thr Tyr
         930              935              940

Thr Pro Glu Ser Phe Val Asn Val Thr Ala Ile Val Gly Phe Cys Val
945              950              955              960

Asn Pro Pro Asn Ala Ser Gln Tyr Ala Leu Val Pro Ala Asn Gly Arg
             965              970              975

Gly Ile Phe Ile Gln Val Asn Gly Ser Tyr Tyr Ile Thr Ala Arg Asp
             980              985              990

Met Tyr Met Pro Arg Asp Ile Thr  Ala Gly Asp Ile Val  Thr Leu Thr
         995              1000              1005

Ser Cys  Gln Ala Asn Tyr Val  Ser Val Asn Arg Thr  Val Ile Thr
    1010              1015              1020

Thr Phe  Val Asp Asn Asp Asp  Phe Asp Phe Asp Asp  Glu Leu Ser
    1025              1030              1035

Lys Trp  Trp Asn Asp Thr Lys  His Glu Leu Pro Asp  Phe Asp Glu
    1040              1045              1050

Phe Asn  Tyr Thr Ile Pro Val  Leu Asn Ile Ser Asn  Glu Ile Asp
    1055              1060              1065

Ile Ile  Gln Glu Val Ile Arg  Gly Leu Asn Asp Ser  Leu Ile Asp
    1070              1075              1080

Leu Glu  Ala Leu Ser Ile Leu  Lys Thr Tyr Ile Lys  Trp Pro Trp
    1085              1090              1095

Tyr Val  Trp Leu Ala Ile Ala  Phe Leu Thr Ile Ile  Phe Ile Leu
    1100              1105              1110

Val Leu  Cys Trp Ile Phe Phe  Met Thr Gly Cys Cys  Gly Cys Cys
    1115              1120              1125

Cys Gly  Cys Phe Gly Ile Met  Pro Leu Met Ser Lys  Cys Gly Lys
    1130              1135              1140

Lys Ser  Ser Tyr Tyr Thr Thr  Phe Asp Asn Asp Val  Val
    1145              1150              1155

<210> SEQ ID NO 6
<211> LENGTH: 1156
<212> TYPE: PRT
<213> ORGANISM: Avian infectious bronchitis virus

<400> SEQUENCE: 6

Met Leu Val Lys Ser Leu Phe Ile Val Thr Leu Leu Phe Ala Leu Cys
1               5               10               15

Ser Ala Ala Leu Phe Asp Asn Asn Gln Ala Val Tyr Tyr Tyr Gln Ser
                20               25               30

Ala Phe Arg Pro Ser Ser Gly Trp His Lys His Gly Gly Ala Tyr Ala
            35               40               45

Val Ala Asn Val Ser Leu Glu Tyr Ala Asn Ala Gly Ser Ser Thr His
        50               55               60

Cys Thr Ala Gly Ala Ile Tyr Trp Ser Lys Asn Phe Thr Ala Ser Ser
65               70               75               80
```

-continued

```
Val Ala Met Thr Ala Pro Gly Thr Gly Met Ser Trp Ser Thr Ala Gln
             85                  90                  95

Phe Cys Thr Ala His Cys Asn Phe Ser Asp Phe Thr Val Phe Val Thr
             100                 105                 110

His Cys Tyr Lys Ser Gly Asp Val Cys Pro Leu Thr Gly Leu Ile Pro
             115                 120                 125

Ser Gly Tyr Ile Arg Ile Ser Ala Met Thr Lys Gly Thr Thr Ser Leu
     130                 135                 140

Phe Tyr Asn Leu Thr Val Pro Val Thr Lys Tyr Pro Lys Phe Lys Ser
145                 150                 155                 160

Leu Gln Cys Val Asp Asn Phe Thr Ser Val Tyr Leu Asn Gly Asp Leu
             165                 170                 175

Val Phe Thr Ser Asn Glu Thr Lys Asp Val Ser Ala Ala Gly Val His
             180                 185                 190

Phe Lys Ala Gly Gly Pro Ile Thr Tyr Lys Val Met Glu Lys Val Asp
             195                 200                 205

Val Leu Ala Tyr Phe Val Asn Gly Thr Ala Gln Asp Val Ile Leu Cys
     210                 215                 220

Asp Asn Ser Pro Arg Gly Leu Leu Ala Cys Gln Tyr Asn Thr Gly Asn
225                 230                 235                 240

Phe Ser Asp Gly Phe Tyr Pro Phe Thr Asn Ile Ser Leu Val Lys Glu
             245                 250                 255

Lys Phe Ile Val Tyr Arg Glu Thr Ser Val Asn Thr Thr Leu Val Leu
             260                 265                 270

Thr Asn Phe Thr Phe Thr Asn Val Ser Asn Ala Leu Pro Asn Thr Gly
             275                 280                 285

Gly Val Asn Thr Ile Asn Ile Tyr Gln Thr Gln Thr Ala Gln Ser Gly
     290                 295                 300

Cys Tyr Asn Phe Asn Phe Ser Phe Leu Ser Ser Phe Val Tyr Lys Gln
305                 310                 315                 320

Ser Asp Phe Met Tyr Gly Ser Tyr His Pro Lys Cys Asp Phe Arg Pro
             325                 330                 335

Glu Thr Ile Asn Asn Gly Leu Trp Phe Asn Ser Leu Ser Val Ser Leu
             340                 345                 350

Ala Tyr Gly Pro Leu Gln Gly Gly Cys Lys Gln Ser Val Phe Ser Asn
             355                 360                 365

Arg Ala Thr Cys Cys Tyr Ala Tyr Ser Tyr Asn Gly Pro Arg Leu Cys
     370                 375                 380

Lys Gly Val Tyr Ile Gly Glu Leu Gln Gln Tyr Phe Glu Cys Gly Leu
385                 390                 395                 400

Leu Val Tyr Val Thr Lys Ser Asp Gly Ser Arg Ile Gln Thr Arg Asn
             405                 410                 415

Glu Pro Leu Val Leu Thr His His Asn Tyr Asn Asn Ile Thr Leu Asp
             420                 425                 430

Arg Cys Val Glu Tyr Asn Ile Tyr Gly Arg Ser Gly Gln Gly Phe Ile
             435                 440                 445

Thr Asn Val Thr Ala Ala Ala Asn Tyr Asn Tyr Leu Ala Asp Gly
     450                 455                 460

Gly Leu Ala Ile Leu Asp Thr Ser Gly Ala Ile Asp Ile Phe Val Val
465                 470                 475                 480

Gln Gly Glu Tyr Gly Pro Asn Tyr Tyr Lys Val Asn Pro Cys Glu Asp
             485                 490                 495

Val Asn Gln Gln Phe Val Val Ser Gly Gly Gly Ile Val Gly Val Leu
```

-continued

```
                500                   505                   510

Thr Ser His Asn Glu Thr Gly Ser Gln Gln Leu Glu Asn Leu Phe Tyr
        515                   520                   525

Val Lys Leu Thr Asn Ser Thr Arg Arg Thr Arg Arg Ser Thr Ile Ala
        530                   535                   540

Asn Val Thr Thr Cys Pro Tyr Val Ser Tyr Gly Arg Phe Cys Ile Lys
545                   550                   555                   560

Pro Asp Gly Leu Val Ser Glu Ile Val Pro Gln Glu Leu Asp Tyr Phe
                565                   570                   575

Val Ala Pro Leu Leu Asn Val Thr Glu His Val Leu Ile Pro Asn Ser
                580                   585                   590

Phe Asn Leu Thr Val Thr Asp Glu Tyr Ile Gln Thr Arg Met Glu Lys
        595                   600                   605

Val Gln Ile Asn Cys Leu Gln Tyr Val Cys Gly Asn Ser Ile Glu Cys
        610                   615                   620

Arg Asn Leu Phe Gln Gln Tyr Gly Pro Val Cys Asp Asn Ile Leu Ser
625                   630                   635                   640

Ile Val Asn Ser Val Gly Gln Arg Glu Asp Met Glu Ser Leu Thr Phe
                645                   650                   655

Tyr Ser Ser Thr Lys Pro Lys Gly Tyr Asn Thr Pro Ile Phe Ser Asn
        660                   665                   670

Ile Ser Thr Gly Asp Phe Asn Ile Ser Leu Met Leu Thr Pro Pro Ser
        675                   680                   685

Ser Pro Ser Gly Arg Ser Phe Ile Glu Asp Leu Leu Phe Thr Ser Val
        690                   695                   700

Glu Thr Val Gly Leu Pro Thr Asp Ala Glu Tyr Lys Lys Cys Thr Ala
705                   710                   715                   720

Gly Pro Leu Gly Thr Leu Lys Asp Leu Ile Cys Ala Arg Glu Tyr Asn
                725                   730                   735

Gly Leu Leu Val Leu Pro Pro Ile Ile Thr Ala Asp Met Gln Thr Met
                740                   745                   750

Tyr Thr Ala Ser Leu Val Gly Ala Met Ala Phe Gly Gly Ile Thr Ser
        755                   760                   765

Ala Ala Ala Ile Pro Phe Ala Thr Gln Ile Gln Ala Arg Ile Asn His
        770                   775                   780

Leu Gly Ile Thr Gln Ser Leu Leu Met Lys Asn Gln Glu Lys Ile Ala
785                   790                   795                   800

Ala Ser Phe Asn Lys Ala Ile Gly His Met Gln Glu Gly Phe Arg Ser
                805                   810                   815

Thr Ser Leu Ala Leu Gln Gln Ile Gln Asp Val Val Asn Lys Gln Ser
                820                   825                   830

Ala Ile Leu Thr Glu Thr Met Asn Ser Leu Asn Lys Asn Phe Gly Ala
        835                   840                   845

Ile Thr Ser Val Ile Gln Asp Ile Tyr Ala Gln Leu Asp Ala Ile Gln
        850                   855                   860

Ala Asp Ala His Val Asp Arg Leu Ile Thr Gly Arg Leu Ser Ser Leu
865                   870                   875                   880

Ser Val Leu Ala Ser Ala Lys Gln Ser Glu Tyr Ile Arg Val Ser Gln
                885                   890                   895

Gln Arg Glu Leu Ala Thr Gln Lys Ile Asn Glu Cys Val Lys Ser Gln
                900                   905                   910

Ser Asn Arg Tyr Gly Phe Cys Gly Ser Gly Arg His Val Leu Ser Ile
        915                   920                   925
```

-continued

```
Pro Gln Asn Ala Pro Asn Gly Ile Val Phe Ile His Phe Thr Tyr Thr
    930             935             940

Pro Glu Ser Phe Val Asn Val Thr Ala Ile Val Gly Phe Cys Val Ser
945             950             955             960

Pro Ala Asn Ala Ser Gln Tyr Ala Ile Val Pro Ala Asn Gly Arg Gly
            965             970             975

Ile Phe Ile Gln Val Asn Gly Thr Tyr Tyr Ile Thr Ala Arg Asp Met
            980             985             990

Tyr Met Pro Arg Asp Ile Thr Ala  Gly Asp Ile Val Thr  Leu Thr Ser
        995             1000            1005

Cys Gln  Ala Asn Tyr Val Asn  Val Asn Lys Thr Val  Ile Thr Thr
    1010            1015            1020

Phe Val  Glu Asp Asp Asp Phe  Asp Phe Asp Asp Glu  Leu Ser Lys
    1025            1030            1035

Trp Trp  Asn Glu Thr Lys His  Glu Ile Pro Asp Phe  Asp Glu Phe
    1040            1045            1050

Asn Tyr  Thr Val Pro Ile Leu  Asn Ile Ser Ser Glu  Ile Asp Arg
    1055            1060            1065

Ile Gln  Gly Val Ile Gln Gly  Leu Asn Asp Ser Leu  Ile Asn Leu
    1070            1075            1080

Glu Glu  Leu Ser Ile Ile Lys  Thr Tyr Ile Lys Trp  Pro Trp Tyr
    1085            1090            1095

Val Trp  Leu Ala Ile Gly Phe  Ala Ile Ile Ile Phe  Ile Leu Ile
    1100            1105            1110

Leu Gly  Trp Val Phe Phe Met  Thr Gly Cys Cys Gly  Cys Cys Cys
    1115            1120            1125

Gly Cys  Phe Gly Ile Ile Pro  Leu Met Ser Lys Cys  Gly Lys Lys
    1130            1135            1140

Ser Ser  Tyr Tyr Thr Thr Phe  Asp Asn Asp Val Val  Thr
    1145            1150            1155
```

```
<210> SEQ ID NO 7
<211> LENGTH: 1169
<212> TYPE: PRT
<213> ORGANISM: Avian infectious bronchitis virus

<400> SEQUENCE: 7
```

```
Met Leu Val Gln Pro Leu Leu Leu Val Thr Leu Leu Cys Ala Leu Cys
1               5               10              15

Ser Ala Ser Leu Tyr Asn Asn Asp Ser Tyr Val Tyr Tyr Gln Ser
            20              25              30

Ala Phe Arg Pro Phe Asn Gly Trp His Leu His Gly Gly Ala Tyr Ala
        35              40              45

Val Val Asn Val Ser Gln Glu Thr Ala Asn Ala Gly Ser Ser Pro Ser
    50              55              60

Cys Thr Ala Gly Ala Ile Tyr Trp Ser Lys Asn Phe Thr Ala Ser Ser
65              70              75              80

Val Ala Met Thr Ala Pro Leu Gln Gly Met Gln Trp Ser Thr Ile Gln
            85              90              95

Phe Cys Thr Ala His Cys Asn Phe Thr Asn Ile Val Val Phe Val Thr
            100             105             110

His Cys Tyr Lys Ser Gly Ser Thr Val Cys Pro Leu Thr Gly Leu Ile
        115             120             125

Pro Gln Asn His Ile Arg Ile Ser Ala Met Lys Gln Gly Asn Asn Gly
```

-continued

```
        130             135             140

Pro Ser Gly Leu Phe Tyr Asn Leu Thr Val Pro Val Thr Lys Tyr Ser
145             150             155             160

Lys Phe Lys Ser Leu Gln Cys Val Asn Asn Gln Thr Ser Val Tyr Leu
                165             170             175

Asn Gly Asp Leu Val Phe Thr Ser Asn Glu Thr Lys Asp Val Ser Gly
                180             185             190

Ala Gly Val Tyr Phe Lys Ala Gly Gly Pro Ile Thr Tyr Lys Val Met
                195             200             205

Arg Glu Val Lys Ala Leu Ala Tyr Phe Val Asn Gly Thr Ala His Asp
        210             215             220

Val Ile Leu Cys Asp Gly Ser Pro Arg Gly Leu Leu Ala Cys Gln Tyr
225             230             235             240

Asn Thr Gly Lys Phe Ser Asp Gly Phe Tyr Pro Phe Thr Asn Asp Thr
                245             250             255

Leu Val Lys Glu Lys Phe Ile Val Tyr Arg Glu Asn Ser Val Asn Thr
                260             265             270

Thr Leu Thr Leu Thr Asn Phe Thr Phe Tyr Asn Glu Ser Asn Ala Leu
                275             280             285

Pro Asn Asn Gly Gly Val Asp Thr Ile Gln Leu Tyr Gln Thr His Thr
        290             295             300

Ala Gln Ser Gly Tyr Tyr Asn Phe Asn Phe Ser Phe Leu Ser Ser Phe
305             310             315             320

Gln Tyr Val Glu Ser Asn Phe Met Tyr Gly Ser Tyr His Pro Lys Cys
                325             330             335

Gly Phe Arg Pro Glu Ser Ile Asn Asn Gly Leu Trp Phe Asn Ser Leu
                340             345             350

Ser Val Ser Leu Ala Tyr Gly Pro Leu Gln Gly Gly Cys Lys Gln Ser
                355             360             365

Val Phe His Gly Arg Ala Thr Cys Cys Tyr Ala Tyr Ser Tyr Asn Gly
        370             375             380

Pro Thr Leu Cys Lys Gly Val Tyr Ser Gly Glu Leu Thr Arg Ser Tyr
385             390             395             400

Gln Cys Gly Leu Leu Val Phe Val Thr Lys Ser Asp Gly Ser Arg Ile
                405             410             415

Gln Thr Ser Thr Lys Pro Ile Val Leu Thr Gln His Asn Tyr Asn Asn
                420             425             430

Ile Thr Leu Asp Arg Cys Val Glu Tyr Asn Ile Tyr Gly Arg Val Gly
                435             440             445

Gln Gly Phe Ile Thr Asn Val Thr Glu Ser Ala Ala Ala Phe Asn Tyr
        450             455             460

Leu Glu Asp Gly Gly Leu Ala Ile Leu Asp Thr Ser Gly Ala Ile Asp
465             470             475             480

Ile Phe Val Val Gln Gly Glu Tyr Gly Phe Asn Tyr Tyr Lys Val Asn
                485             490             495

Pro Cys Glu Asp Val Asn Gln Gln Phe Val Val Ser Gly Gly Asn Leu
                500             505             510

Val Gly Ile Leu Thr Ser Ile Asn Gln Thr Gly Ser Gln Ser Ile Glu
                515             520             525

Asn Gln Phe Tyr Val Lys Leu Thr Asn Gly Ser Arg Arg Ser Arg Arg
        530             535             540

Ser Val Ser Glu Asn Val Thr Ser Cys Pro Tyr Val Ser Tyr Gly Lys
545             550             555             560
```

-continued

```
Phe Cys Ile Lys Pro Asp Gly Ser Leu Ser Thr Ile Val Pro Lys Glu
              565             570             575

Leu Glu Gln Phe Val Ala Pro Leu Leu Asn Val Thr Glu His Val Leu
              580             585             590

Ile Pro Asp Ser Phe Asn Leu Thr Val Thr Asp Glu Tyr Ile Gln Thr
              595             600             605

Arg Met Asp Lys Val Gln Ile Asn Cys Leu Gln Tyr Val Cys Gly Asn
              610             615             620

Ser Phe Glu Cys Arg Lys Leu Phe Gln Gln Tyr Gly Pro Val Cys Asp
625             630             635             640

Asn Ile Leu Ser Val Val Asn Ser Val Gly Gln Lys Glu Asp Met Glu
              645             650             655

Leu Leu Ser Phe Tyr Ser Ser Thr Lys Pro Ser Gly Ile Ser Gln Pro
              660             665             670

Leu Phe Asn Asn Phe Ser Thr Gly Asp Phe Asn Ile Ser Leu Leu Leu
              675             680             685

Thr Ser Pro Ser Ser Pro Ser Gly Arg Ser Phe Ile Glu Asp Leu Leu
690             695             700

Phe Thr Ser Val Glu Ser Val Gly Leu Pro Thr Asp Glu Ala Tyr Lys
705             710             715             720

Lys Cys Thr Ser Gly Pro Leu Gly Phe Val Lys Asp Leu Val Cys Ala
              725             730             735

Arg Glu Tyr Asn Gly Leu Leu Val Leu Pro Pro Ile Ile Thr Ala Glu
              740             745             750

Met Gln Thr Met Tyr Thr Ser Ser Leu Val Ala Ser Met Ala Leu Gly
              755             760             765

Gly Ile Thr Ala Ala Gly Ala Ile Pro Phe Ala Thr Gln Leu Gln Ala
              770             775             780

Arg Ile Asn His Leu Gly Ile Thr Gln Ser Leu Leu Met Lys Asn Gln
785             790             795             800

Glu Lys Ile Ala Ala Ser Phe Asn Arg Ala Ile Gly His Met Gln Glu
              805             810             815

Gly Phe Lys Ser Thr Ser Leu Ala Leu Gln Gln Ile Gln Asp Val Val
              820             825             830

Asn Lys Gln Ser Ala Ile Leu Thr Glu Thr Met Ala Ser Leu Asn Lys
              835             840             845

Asn Phe Gly Ala Ile Ser Ser Val Leu Gln Asp Ile Tyr Gln Gln Leu
850             855             860

Asp Val Ile Gln Ala Asp Ala His Val Asp Arg Ile Ile Thr Gly Arg
865             870             875             880

Leu Ser Ser Leu Ser Val Leu Ala Ser Ala Lys Gln Ser Glu Tyr Ile
              885             890             895

Ala Val Ser Gln Gln Arg Ala Leu Ala Thr Gln Lys Ile Asn Glu Cys
              900             905             910

Val Lys Ser Gln Ser Thr Arg Tyr Ser Phe Cys Gly Asn Gly Arg His
              915             920             925

Val Leu Thr Ile Pro Gln Asn Ala Pro Asn Gly Ile Val Phe Ile His
              930             935             940

Phe Thr Tyr Thr Pro Glu Ser Phe Val Asn Val Thr Ala Ile Val Gly
945             950             955             960

Phe Cys Val Lys Pro Pro Asn Ala Ser His Tyr Ala Ile Val Pro Val
              965             970             975
```

-continued

```
Asn Gly Arg Gly Ile Phe Ile Gln Val Asn Gly Thr Tyr Tyr Ile Thr
        980                 985                 990

Ser Arg Asp Met Tyr Met Pro Arg Asn Ile Thr Ala Gly Asp Ile Val
        995                 1000                1005

Thr Leu Thr Ser Cys Gln Ala Asn Tyr Val Ser Val Asn Lys Thr
        1010                1015                1020

Val Ile Ser Thr Phe Val Glu Asp Asp Asp Phe Asp Phe Asp Asp
        1025                1030                1035

Glu Leu Ser Lys Trp Trp Asn Asp Thr Lys His Glu Leu Pro Asp
        1040                1045                1050

Phe Asp Glu Phe Asn Tyr Thr Ile Pro Val Leu Asn Ile Ser Asn
        1055                1060                1065

Glu Ile Asp Arg Ile Gln Gly Val Ile Gln Gly Leu Asn Asp Ser
        1070                1075                1080

Leu Ile Asp Leu Glu Thr Leu Ser Ile Leu Lys Thr Tyr Ile Lys
        1085                1090                1095

Trp Pro Trp Tyr Val Trp Leu Ala Ile Phe Phe Ala Ile Val Ile
        1100                1105                1110

Phe Ile Leu Ile Ile Gly Trp Val Phe Phe Met Thr Gly Cys Cys
        1115                1120                1125

Gly Cys Cys Cys Gly Cys Phe Gly Ile Ile Pro Leu Met Asn Lys
        1130                1135                1140

Cys Gly Lys Lys Ser Ser Tyr Tyr Thr Thr Phe Asp Asn Asp Val
        1145                1150                1155

Val Thr Glu Gln Tyr Arg Pro Lys Lys Ser Val
        1160                1165
```

```
<210> SEQ ID NO 8
<211> LENGTH: 1159
<212> TYPE: PRT
<213> ORGANISM: Avian infectious bronchitis virus

<400> SEQUENCE: 8

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Phe Ser Ala Ala Ser
65                  70                  75                  80

Val Ala Met Thr Ala Pro Leu Ser Gly Met Ser Trp Ser Ala Ser Ser
                85                  90                  95

Phe Cys Thr Ala His Cys Asn Phe Thr Ser Tyr Ile Val Phe Val Thr
            100                 105                 110

His Cys Phe Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Arg Thr
        130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
            165                 170                 175
```

-continued

```
Asn Gly Asp Leu Val Phe Thr Ser Gly Tyr Thr Glu Asp Val Val Ala
            180                 185                 190

Ala Gly Val His Phe Lys Ser Gly Gly Pro Ile Thr Tyr Lys Val Met
            195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
            275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
                340                 345                 350

Val Ser Leu Thr Tyr Gly Pro Ile Gln Gly Gly Cys Lys Gln Ser Val
            355                 360                 365

Phe Asn Gly Lys Ala Thr Cys Cys Tyr Ala Tyr Ser Tyr Gly Gly Pro
    370                 375                 380

Arg Ala Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
                405                 410                 415

Thr Ala Thr Gln Pro Pro Val Leu Thr Gln Asn Phe Tyr Asn Asn Ile
            420                 425                 430

Thr Leu Gly Lys Cys Val Asp Tyr Asn Val Tyr Gly Arg Thr Gly Gln
            435                 440                 445

Gly Phe Ile Thr Asn Val Thr Asp Leu Ala Thr Ser His Asn Tyr Leu
    450                 455                 460

Ala Asp Gly Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Leu
                485                 490                 495

Cys Glu Asp Val Asn Gln Gln Phe Val Val Ser Gly Gly Lys Leu Val
            500                 505                 510

Gly Ile Leu Thr Ser Arg Asn Glu Thr Gly Ser Gln Pro Leu Glu Asn
            515                 520                 525

Gln Phe Tyr Ile Lys Ile Thr Asn Gly Thr His Arg Ser Arg Arg Ser
    530                 535                 540

Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
                565                 570                 575

Glu Gln Phe Val Ala Pro Leu Leu Asn Val Thr Glu Asn Val Leu Ile
                580                 585                 590
```

-continued

```
Pro Asn Ser Phe Asn Leu Thr Val Thr Asp Glu Tyr Ile Gln Thr His
        595                 600                 605

Met Asp Lys Ile Gln Ile Asn Cys Leu Gln Tyr Val Cys Gly Asn Ser
        610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                645                 650                 655

Leu Ser Phe Tyr Ser Ser Thr Lys Pro Ser Gly Phe Asn Thr Pro Val
                660                 665                 670

Phe Ser Asn Leu Ser Thr Gly Glu Phe Asn Ile Ser Leu Leu Leu Thr
                675                 680                 685

Thr Pro Ser Ser Pro Arg Gly Arg Ser Phe Ile Glu Asp Leu Leu Phe
        690                 695                 700

Thr Ser Val Glu Ser Val Gly Leu Pro Thr Asp Glu Ala Tyr Lys Lys
705                 710                 715                 720

Cys Thr Ala Gly Pro Leu Gly Phe Leu Lys Asp Leu Ala Cys Ala Arg
                725                 730                 735

Glu Tyr Asn Gly Leu Leu Val Leu Pro Pro Ile Ile Thr Ala Glu Met
                740                 745                 750

Gln Thr Leu Tyr Thr Ser Ser Leu Val Val Ser Met Ala Phe Gly Gly
                755                 760                 765

Ile Thr Ser Ala Gly Ala Ile Pro Phe Ala Thr Gln Leu Gln Ala Arg
        770                 775                 780

Ile Asn His Leu Gly Ile Thr Gln Ser Leu Leu Leu Lys Asn Gln Glu
785                 790                 795                 800

Lys Ile Ala Ala Ser Phe Asn Lys Ala Ile Gly His Met Gln Glu Gly
                805                 810                 815

Phe Arg Ser Thr Ser Leu Ala Leu Gln Gln Ile Gln Asp Val Val Asn
                820                 825                 830

Lys Gln Ser Ala Ile Leu Thr Glu Thr Met Ala Ser Leu Asn Lys Asn
                835                 840                 845

Phe Gly Ala Ile Ser Ser Val Ile Gln Glu Ile Tyr Gln Gln Leu Asp
        850                 855                 860

Ala Ile Gln Ala Asn Ala His Val Asp Arg Leu Ile Thr Gly Arg Leu
865                 870                 875                 880

Ser Ser Leu Ser Val Leu Ala Ser Ala Lys Gln Ala Glu Tyr Ile Arg
                885                 890                 895

Val Ser Gln Gln Arg Glu Leu Ala Thr Gln Lys Ile Asn Glu Cys Val
                900                 905                 910

Lys Ser Gln Ser Ile Arg Tyr Ser Phe Cys Gly Asn Gly Arg His Val
                915                 920                 925

Leu Thr Ile Pro Gln Asn Ala Pro Asn Gly Ile Val Phe Ile His Phe
        930                 935                 940

Ser Tyr Thr Pro Asp Ser Phe Val Asn Val Thr Ala Ile Val Gly Phe
945                 950                 955                 960

Cys Val Lys Pro Ala Asn Ala Ser Gln Tyr Ala Ile Val Pro Ala Asn
                965                 970                 975

Gly Arg Gly Ile Phe Ile Gln Val Asn Gly Ser Tyr Tyr Ile Thr Ala
                980                 985                 990

Arg Asp Met Tyr Met Pro Arg Ala  Ile Thr Ala Gly Asp  Ile Val Thr
        995                 1000                1005

Leu Thr  Ser Cys Gln Ala Asn  Tyr Val Ser Val Asn  Lys Thr Val
```

```
        1010            1015            1020
```

Ile Thr  Thr Phe Val Asp Asn  Asp Asp Phe Asp Phe  Asn Asp Glu
    1025            1030            1035

Leu Ser  Lys Trp Trp Asn Asp  Thr Lys His Glu Leu  Pro Asp Phe
    1040            1045            1050

Asp Lys  Phe Asn Tyr Thr Val  Pro Ile Leu Asp Ile  Asp Ser Glu
    1055            1060            1065

Ile Asp  Arg Ile Gln Gly Val  Ile Gln Gly Leu Asn  Asp Ser Leu
    1070            1075            1080

Ile Asp  Leu Glu Lys Leu Ser  Ile Leu Lys Thr Tyr  Ile Lys Trp
    1085            1090            1095

Pro Trp  Tyr Val Trp Leu Ala  Ile Ala Phe Ala Thr  Ile Ile Phe
    1100            1105            1110

Ile Leu  Ile Leu Gly Trp Val  Phe Phe Met Thr Gly  Cys Cys Gly
    1115            1120            1125

Cys Cys  Cys Gly Cys Phe Gly  Ile Met Pro Leu Met  Ser Lys Cys
    1130            1135            1140

Gly Lys  Lys Ser Ser Tyr Tyr  Thr Thr Phe Asp Asn  Asp Val Val
    1145            1150            1155

Thr

<210> SEQ ID NO 9
<211> LENGTH: 11398
<212> TYPE: DNA
<213> ORGANISM: Artificial Sequence
<220> FEATURE:
<223> OTHER INFORMATION: Plasmid Sequence

<400> SEQUENCE: 9
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg        120 ttggcgggtg tcggggctgg cttaactatg cggcatcaga gcagattgta ctgagagtgc        180
accatatgcg gtgtgaaata ccgcacagat gcgtaaggag aaaataccgc atcaggcgcc        240
attcgccatt caggctgcgc aactgttggg aagggcgatc ggtgcgggcc tcttcgctat        300
tacgccagct ggcgaaaggg ggatgtgctg caaggcgatt aagttgggta acgccaggt        360 tttcccagtc acgacgttgt aaaacgacgg ccagtgaatt ggagatcggt acttcgcgaa        420
tgcgtcgaga tcggccgccc gggtaatacg actcactata gggacttaag atagatatta        480
atatatatct attgcactag ccttgcgcta gatttcaaac ttaacaaaac ggacttaaat        540
acctacagct ggtccccata ggtgttccat tgcagtgcac tttagtgccc tggatggcac        600
ctggccacct gtcaggtttt tgttgttaaa atatcattgt tgctggtatc actgcttgtt        660
ttgccgtgtc tcactttata catccgttgc ttgggctacc tagtatccag cgtcctacgg        720
gcgccgtggt cggttcgagt gcgaaggacc tctggttcat ctagcggtag gcgggtgtgt        780
ggaagtagcg cttcagacgt actggttctg ttgcgtgaaa cgcggggtca cctccccca        840 catacctcta agggctttg agcctagcgt tgggctacgt tctcgcacaa ggtcggctat        900
acgacgtttg tagggggtag tgccaaacaa cccctgaggt gacaggttct ggtggtgttt        960
cgaaaacaac aatgtgtgtg ccgcataata tgcgcgttat gcattttgga gcaggtagtg       1020
ataaaggagt ggcgcctggt agtactgttc ttaaacagtg gctccccgaa ggaacactcc       1080
ttgtcgataa tgatattgta gattatgttt ctgacgcaca cgtttctgtg ctttcagatt       1140
```

-continued

```
gcaataaata taagacagag cacaagtttg atcttgtgat atctgatatg tatacagaca      1200
atgattcaaa aagaaagcat gaaggcgtga tagccaataa tggcaatgat gacgtcttca      1260 tataccttc aagttttcta cgcaataatt tggctctggg aggcagtttt gctgtaaaat       1320
taacagagac aagttggcat gagagtttat atgacattgc acaggattgt gcatggtgga      1380
caatgttttg tacagcagtg aatgcatctt cttcagaagc attcctgatt ggtgttaatt      1440
acttgggtgc aagtgcaaag gttaaagtta gtggaaaaac actgcacgca aattatatat      1500
tttggaggaa ttgtaattat ttacaaacct ctgcttatag tatatttgat gttgctaagt      1560
ttgatttgag attgaaagca acgccagttg ttaatcttaa gactgaacaa aagacagact      1620
tagtctttaa tttgataaag tgtggtaagt tactggtaag agatgttggt aacacctctt      1680
ttactagtga ctcttttgtg tgcactatgt agtgctgctt tgtatgacag tagttcttac      1740
gtgtactact accaaagtgc cttcagacca cctgatggtt ggcatttaca tggggggtgcg     1800 tatgcggttg ttaatatttc tagtgaatct aataatgcag gctcttcatc tgggtgtact     1860
gttggtatta ttcatggtgg tcgtgttgtt aatgcttctt ctatagctat gacggcaccg      1920
tcatcaggta tggcttggtc tagcagtcag ttttgtactg catactgtaa cttttcagat      1980
actacagtgt ttgttacaca ttgttataaa catggtgggt gtcctataac tggcatgctt      2040
caacagcatt ctatacgtgt ttctgctatg aaaaatggcc agctttttta taatttaaca      2100
gttagtgtag ctaagtaccc tacttttaaa tcatttcagt gtgttaataa tttaacatcc      2160
gtatatttaa atggtgatct tgtttacacc tctaatgaga ccacagatgt tacatctgca      2220
ggtgtttatt ttaaagctgg tggacctata acttataaag ttatgagaga agttagagcc      2280
ctggcttatt ttgttaatgg tactgcacaa gatgttattt tgtgtgatgg gtcacctaga      2340
ggcttgttag catgccagta taatactggc aattttttcag atggcttta tcctttttact     2400 aatagtagtt tagttaagca gaagtttatt gtctatcgtg aaaatagtgt taatactact      2460
tttacgttac acaatttcac ttttcataat gagactggcg ccaacccaaa tcctagtggt      2520
gtccagaata ttcaaactta ccaaacacaa acagctcaga gtggttatta taattttaat      2580
ttttcctttc tgagtagttt tgtttataag gagtctaatt ttatgtatgg atcttatcac      2640
ccaagttgta atttttagact agaaactatt aataatggtt tgtggtttaa ttcactttca     2700
gtttcaattg cttacggtcc tcttcaaggt ggttgcaagc aatctgtctt tagtggtaga      2760
gcaacctgtt gttatgctta ctcatatgga ggtccttttgc tgtgtaaagg tgtttattca     2820
ggtgagttag atcataattt tgaatgtgga ctgttagttt atgttactaa gagcggtggc      2880
tctcgtatac aaacagccac tgaaccgcca gttataactc aacacaatta taataatatt     2940
actttaaata cttgtgttga ttataatata tatggcagaa ctggccaagg tttttattact     3000 aatgtaaccg actcagctgt tagttataat tatctagcag acgcaggttt ggctatttta      3060
gatacatctg gttccataga catctttgtc gtacaaagtg aatatggtct taattattat      3120
aaggttaacc cttgcgaaga tgtcaaccag cagtttgtag tttctggtgg taaattagta      3180
ggtattctta cttcacgtaa tgagactggt tcccagcttc ttgagaatca gttttacatc      3240
aaaatcacta atggaacacg tcgttttaga cgttctatta ctgaaagtgt tgaaaattgc      3300
ccttatgtta gttatggtaa gttttgtata aaacctgatg gttcaattgc cacaatagta      3360
ccaaaacaat tggaacagtt tgtggcacct ttacttaatg ttactgaaaa tgtgctcata      3420
cctaacagtt ttaatttaac tgttacagat gagtacatac aaacgcgtat ggataaggtc      3480
caaattaatt gcctgcagta tatttgtggc aattctctgg agtgcagaaa tttgtttcaa      3540
```

```
caatatggtc ctgtttgcga caacatattg tctgtagtaa atagtgttgg tcaaaaagaa   3600
gatatggaac ttttgaattt ctattcttct actaagccgg ctggtttaa tacaccagtt    3660 cttagtaatg ttagcactgg tgagtttaat attactcttt ttttaacaac gcctagtagt   3720
cctagaaggc gttcttttat tgaagacctt ctatttacaa gtgttgaatc tgttggatta   3780
ccaacagatg acgcatacaa aaattgcact gcaggtcctt taggctttct taaggacctt   3840
gcatgtgctc gtgaatataa tggtttgctt gtgttgcctc ctattataac agcagaaatg   3900
caaactttgt atactagttc tctagtagct tctatggctt ttggtggtat tactgcagct   3960
ggtgctatac cttttgccac acaactgcag gctagaatta atcacttggg tattacccag   4020
tcacttcttt tgaagaatca agaaaaaatt gctgcttcct ttaataaggc catcggtcat   4080
atgcaggaag gttttagaag tacatcttta gcattacaac aaattcaaga tgttgttaat   4140
aagcagagtg ctattcttac tgagactatg gcatcactta ataaaaattt tggtgccatt   4200
tcttctgtga ttcaagaaat ctaccagcaa cttgacgcca tacaagcaaa tgctcacgtg   4260
gatcgtctta taactggtag attgtcatca cttttctgttt tagcatctgc taagcaggcg   4320
gagtatatta gagtgtcaca acagcgtgag ttagctactc agaagattaa tgagtgtgtt   4380
aagtcacagt ccattaggta ctcctttttgt ggtaatggac gacatgtttt aaccataccg   4440
caaaatgcac ctaatggtat agtgtttata cacttttctt acactccaga tagttttgtt   4500
aatgttactg caatagtggg tttttgtgta aagccagcta atgctagtca gtatgcaata   4560
gtacccgcta atggtagggg tattttttata caagttaatg gtagttacta catcactgca   4620
cgagatatgt atatgccaag agctattact gcaggagata tagttacgct tacttcttgt   4680
caagcaaatt atgtaagtgt aaataagacc gtcattacta cattcgtaga caatgatgat   4740
tttgatttta atgacgaatt gtcaaaatgg tggaatgata ctaagcatga gctaccagac   4800
tttgacaaat tcaattacac agtacctata cttgacattg atagtgaaat tgatcgtatt   4860
caaggcgtta tacagggtct taatgactct ctaatagacc ttgaaaaact ttcaatactc   4920
aaaacttata ttaagtggcc ttggtatgtg tggttagcca tagcttttgc cactattatc   4980
ttcatcttaa tattaggatg ggttttcttc atgactgggt gttgtggttg ttgttgtgga   5040
tgctttggca ttatgcctct aatgagtaag tgtggtaaga aatcttctta ttacacgact   5100
tttgataacg atgtggtaac tgaacaatac agacctaaaa agtctgttta atgatccaaa   5160
gtcccactag tttcttaata gtattaattt tgctttggtg taaacttgta ctaagttgtt   5220
ttagagagtt tattattgcc cttcaacaac taacacaagt tttactccaa attatcgata   5280
gtaatttaca gtctagactg accctttggc acagtctaga ctaatgttaa acttagaagc   5340
aattattgaa accggtgatc aagtgattca aaaaatcagt ttcaatttac agcatatttc   5400
aagtgtatta aacacagaag tatttgaccc ctttgactat tgttattaca gaggaggtaa   5460
tttttgggaa atagagtcag ctgaagattg ttcaggtgat gatgaattta ttgaataagt   5520
cgctagagga gaatggaagt tttctaacgg cactttacat atttgtagga tttttagcat   5580
tttatcttct aggtagagca cttcaagcat ttgtacaggc tgctgatgct tgttgtttat   5640
tttggtacac gtggttagta attccaggag ttaagggtac agcctttgta tacaagtata   5700
catatggtag aaaacttaac aattcggaat tagaagcagt tgttgttaac gagtttccta   5760
agaacggttg gaataataaa aatccagcaa attttcaaga tgtccaacga aacaaattgt   5820
actcttgact ttgaacagtc agttgagctt tttaaagagt ataattttatt tataactgca   5880
```

-continued

```
ttcttgttgt tcttaaccat aatacttcag tatggttatg caacgcgtag taagtttatt      5940
tatatactta aaatgatagt gttatggtgc ttttggcccc ttaacattgc agtaggtgta      6000
atttcatgta tatacccacc aaacacagga ggtcttgtcg cagcgataat acttactgtg      6060
tttgcgtgtc tttcttttgt aggttattgg atccagagta ttagactctt taagcggtgt      6120
agatcttggt ggtcatttaa cccagaatct aacgccgtag gttcaatact cctaactaat      6180
ggtcaacaat gtaattttgc tatagagagt gtgccgatgg tgctttctcc tattataaag      6240
aatggtgttc tttattgtga gggtcagtgg cttgctaaat gtgaaccaga ccacttgcct      6300
aaagacatat ttgtatgcac accagataga cgtaatatct atcgtatggt gcagaaatac      6360
actggtgacc aaagcggaaa taagaaaagg tttgctacat ttgtctatgc aaagcagtca      6420
gtagacactg gcgagctaga aagtgtagca acaggtggaa gtagccttta cacataaatg      6480
tgtgtgtgta gagagtattt aaaattattc ttcaatagtg cctctatttt aagagcgcgg      6540
aagagtattt gttttgagga tattaatata aatcctcttt gttttgtact ctctttacaa      6600
gagttattat ttaagcaaca gttttttcctt tcctttgttt ggaagaaagt tgttgttaat      6660
ggtgtagaat tccaagtaga aaatggaaaa gtccactacg aaggaaaccc catttttccaa      6720 aaaggttgtt gtaggttgtg gtcccattat aagaaggatt aaatggatta aaccacctac      6780
actacttact tgtaataagg gcgtttggac ttacaagcgc ttaacaaata cagacgatga      6840
aatggctgac tagttttgga agagcagtta tttcttgtta taaagcccta ctattaactc      6900
agttaagagt attagatagg ttaattttag atcacggacc aaagcgagtc ttaacgtgtg      6960
gtaggcgagt gcttttatct caattagatt tagtttatag gttggcatat acgcccaccc      7020
aatcgctggt atgaataata gtaaagataa tccttttcgc ggagcaatag caagaaaagc      7080
gcgaatttat ctgagagaag gattagagtg tgtttacttt cttaacaaag caggacaagc      7140
agagccttgt cccgcgtgta cctccctagt atttcagggg aaaacttgtg aggaacacac      7200
agataataat aatcttttgt catggcgagc ggtaagacaa ctgggaagac agacgcccca      7260
gcgccagtca tcaaactagg agggccaaaa ccacctaaag ttggttcttc tggaaatgct      7320
agctggtttc aagcactaaa agccaagaag ttaaattcac ctcctcctaa gtttgaaggt      7380
agcggcgttc ctgataatga aaatcttaaa ttaagccagc aacatgggta ctggagacgt      7440
caagccaggt acaagccagg taaaggcgga agaaaatcag tcccagatgc ttggtacttc      7500
tattacactg gaacaggacc agccgctgac ctgaattggg gtgatagcca agatggtata      7560
gtgtgggttt ctgcaaaggg tgctgatact aaatctagat ctaaccaggg tacaaggggat      7620 cctgataagt ttgaccaata cccgctacga ttctcagatg gaggacctga tggtaatttc      7680
cgttgggact tcattccaat aaatcgtggt aggagtggaa gatcaacagc ggcttcatca      7740
gcagcatcta gtagagcacc gtcgcgtgat ggctcgcgtg gacgtagaag cggagctgaa      7800
gatgatctta tagctcgtgc agcaaagatc attcaggatc agcagaagaa gggttctcgc      7860
attactaaag ctaaggccga tgaaatggct catcgccggt attgtaagcg tactatccca      7920
cctggttata aggttgatca agtatttggt ccccgtacta aaggtaagga gggaaatttt      7980
ggtgatgaca agatgaatga ggagggtatt aaggatgggc gcgttacagc aatgctcaac      8040
ctagtcccta gcagccatgc ttgtcttttt ggaagtagag tgacgcccaa acttcaacca      8100
gatgggctgc acttgagatt tgaatttact actgtggttt ctaggatga tccgcagttt      8160 gataattatg tgaaaatttg tgatcagtgt gtcgatggtg tagggactcg gccaaaagac      8220
gatgaaccga gaccaaagtc acgcccaaat tcaagacctg ctacaagaac aagttctcca      8280
```

```
gcgccaagac aacagcgtca aaagaaggag aagaagtcaa agaagcagga tgatgaagta   8340
gataaggcat tgacctcaga tgaggagagg aacaatgcac agctggaatt tgatgatgaa   8400
ccgaaagtga ttaactgggg ggattcagca cttggagaga atgagttgta aagctagatt   8460
tccaacttaa catcatggac gtgcgtatgc tgttttccc tactatagac ttttagcat    8520 attatttttt gctatttgta tggtttatta caggtgaaga ttgtatgtat ttgttgtaca   8580
ctcgtatgtt ctatattatg ttttctgtag ttgttattag tgttgttctt gttcttactc   8640
tactgttctc ttttctttat tttagagtat caataagaat caaggaagat aggcatgtag   8700
tttgattacc tacatgtcta tcgccaggga aatgtctaat ctgtctactt agtagcctgg   8760
aaacgaacgg tagacccta gattttaatt tagtttaatt tttagtttag tttaagttag    8820
tttagagtag gtataaagaa gccagtgccg gggccacgcg gagtacgatc gagggtacag   8880
cactaggacg cccactaggg gaagagctaa attttagttt aagttaagtt taattggcta   8940
agtatagtta aaatttatag gctagtatag agttagagca aaaaaaaaaa aaaaaaaaaa   9000
aaaaaaaaaa aaaaaaaaaa aaaaaaaaaa aaaaaaaaaa aaaaaaaaaa aaaaaaaaaa   9060
aaaaaaaaaa aaaaaaaaag tttaaactta attaagaatt cccttggctc gagttcgaaa   9120
tcggatgccg ggaccgacga gtgcagaggc gtgcaagcga gcttggcgta atcatggtca   9180
tagctgtttc ctgtgtgaaa ttgttatccg ctcacaattc cacacaacat acgagccgga   9240
agcataaagt gtaaagcctg gggtgcctaa tgagtgagct aactcacatt aattgcgttg   9300
cgctcactgc ccgctttcca gtcgggaaac ctgtcgtgcc agctgcatta atgaatcggc   9360
caacgcgcgg ggagaggcgg tttgcgtatt gggcgctctt ccgcttcctc gctcactgac   9420
tcgctgcgct cggtcgttcg gctgcggcga gcggtatcag ctcactcaaa ggcggtaata   9480
cggttatcca cagaatcagg ggataacgca ggaaagaaca tgtgagcaaa aggccagcaa   9540
aaggccagga accgtaaaaa ggccgcgttg ctggcgtttt tccataggct ccgcccccct   9600
gacgagcatc acaaaaatcg acgctcaagt cagaggtggc gaaacccgac aggactataa   9660
agataccagg cgtttccccc tggaagctcc ctcgtgcgct ctcctgttcc gaccctgccg   9720
cttaccggat acctgtccgc ctttctccct tcgggaagcg tggcgctttc tcatagctca   9780
cgctgtaggt atctcagttc ggtgtaggtc gttcgctcca agctgggctg tgtgcacgaa   9840
ccccccgttc agcccgaccg ctgcgcctta tccggtaact atcgtcttga gtccaacccg   9900
gtaagacacg acttatcgcc actggcagca gccactggta acaggattag cagagcgagg   9960
tatgtaggcg gtgctacaga gttcttgaag tggtggccta actacggcta cactagaaga  10020
acagtatttg gtatctgcgc tctgctgaag ccagttacct tcggaaaaag agttggtagc  10080
tcttgatccg gcaaacaaac caccgctggt agcggtggtt ttttttgtttg caagcagcag  10140 attacgcgca gaaaaaaagg atctcaagaa gatcctttga tcttttctac ggggtctgac  10200
gctcagtgga acgaaaactc acgttaaggg attttggtca tgagattatc aaaaaggatc  10260
ttcacctaga tccttttaaa ttaaaaatga agttttaaat caatctaaag tatatatgag  10320
taaacttggt ctgacagtta ccaatgctta atcagtgagg cacctatctc agcgatctgt  10380
ctatttcgtt catccatagt tgcctgactc cccgtcgtgt agataactac gatacgggag  10440
ggcttaccat ctggccccag tgctgcaatg ataccgcgag acccacgctc accggctcca  10500
gatttatcag caataaacca gccagccgga agggccgagc gcagaagtgg tcctgcaact  10560
ttatccgcct ccatccagtc tattaattgt tgccgggaag ctagagtaag tagttcgcca  10620
```

-continued

```
gttaatagtt tgcgcaacgt tgttgccatt gctacaggca tcgtggtgtc acgctcgtcg   10680
tttggtatgg cttcattcag ctccggttcc caacgatcaa ggcgagttac atgatccccc   10740
atgttgtgca aaaaagcggt tagctccttc ggtcctccga tcgttgtcag aagtaagttg   10800
gccgcagtgt tatcactcat ggttatggca gcactgcata attctcttac tgtcatgcca   10860
tccgtaagat gcttttctgt gactggtgag tactcaacca agtcattctg agaatagtgt   10920
atgcggcgac cgagttgctc ttgcccggcg tcaatacggg ataataccgc gccacatagc   10980
agaactttaa aagtgctcat cattggaaaa cgttcttcgg ggcgaaaact ctcaaggatc   11040
ttaccgctgt tgagatccag ttcgatgtaa cccactcgtg cacccaactg atcttcagca   11100
tcttttactt tcaccagcgt ttctgggtga gcaaaaacag gaaggcaaaa tgccgcaaaa   11160
aagggaataa gggcgacacg gaaatgttga atactcatac tcttcctttt tcaatattat   11220
tgaagcattt atcagggtta ttgtctcatg agcggataca tatttgaatg tatttagaaa   11280
aataaacaaa taggggttcc gcgcacattt ccccgaaaag tgccacctga cgtctaagaa   11340
accattatta tcatgacatt aacctataaa aataggcgta tcacgaggcc ctttcgtc     11398
```

<210> SEQ ID NO 10
<211> LENGTH: 11398
<212> TYPE: DNA
<213> ORGANISM: Artificial Sequence
<220> FEATURE:
<223> OTHER INFORMATION: Plasmid Sequence

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ggagatcggt acttcgcgaa     420
tgcgtcgaga tcggccgccc gggtaatacg actcactata gggacttaag atagatatta     480
atatatatct attgcactag ccttgcgcta gatttcaaac ttaacaaaac ggacttaaat     540
acctacagct ggtccccata ggtgttccat tgcagtgcac tttagtgccc tggatggcac     600
ctggccacct gtcaggtttt tgttgttaaa atatcattgt tgctggtatc actgcttgtt     660
ttgccgtgtc tcactttata catccgttgc ttgggctacc tagtatccag cgtcctacgg     720
gcgccgtggt cggttcgagt gcgaaggacc tctggttcat ctagcggtag gcgggtgtgt     780
ggaagtagcg cttcagacgt actggttctg ttgcgtgaaa cgcggggtca cctcccccca     840
catacctcta agggcttttg agcctagcgt tgggctacgt tctcgcacaa ggtcggctat     900
acgacgtttg taggggtag tgccaaacaa ccctgaggt gacaggttct ggtggtgttt     960
cgaaaacaac aatgtgtgtg ccgcataata tgcgcgttat gcattttgga gcaggtagtg    1020
ataaaggagt ggcgcctggt agtactgttc ttaaacagtg gctccccgaa ggaacactcc    1080
ttgtcgataa tgatattgta gattatgttt ctgacgcaca cgtttctgtg ctttcagatt    1140
gcaataaata taagacagag cacaagtttg atcttgtgat atctgatatg tatacagaca    1200
atgattcaaa aagaaagcat gaaggcgtga tagccaataa tggcaatgat gacgtcttca    1260
tatacctttc aagttttcta cgcaataatt tggctctggg aggcagtttt gctgtaaaat    1320
```

-continued

```
taacagagac aagttggcat gagagtttat atgacattgc acaggattgt gcatggtgga    1380
caatgttttg tacagcagtg aatgcatctt cttcagaagc attcctgatt ggtgttaatt    1440
acttgggtgc aagtgcaaag gttaaagtta gtggaaaaac actgcacgca aattatatat    1500
tttggaggaa ttgtaattat ttacaaacct ctgcttatag tatatttgat gttgctaagt    1560
ttgatttgag attgaaagca acgccagttg ttaatcttaa gactgaacaa aagacagact    1620
tagtctttaa tttgataaag tgtggtaagt tactggtaag agatgttggt aacacctctt    1680
ttactagtga ctcttttgtg tgcactatgt agtgctgctt tgtatgactc gagttcttac    1740
gtgtactact accaaagtgc cttcagacca cctgatggtt ggcatttaca tgggggtgcg    1800
tatgcggttg ttaatatttc tagtgaatct aataatgcag gctcttcatc tgggtgtact    1860
gttggtatta ttcatggtgg tcgtgttgtt aatgcttctt ctatagctat gacggcaccg    1920
tcatcaggta tggcttggtc tagcagtcag ttttgtactg catactgtaa cttttcagat    1980
actacagtgt ttgttacaca ttgttataaa catggtgggt gtcctataac tggcatgctt    2040
caacagcatt ctatacgtgt ttctgctatg aaaaatggcc agcttttcta taatttaaca    2100
gttagtgtag ctaagtaccc tacttttaaa tcatttcagt gtgttaataa tttaacatcc    2160
gtatatttaa atggtgatct tgtttacacc tctaatgaga ccacagatgt tacatctgca    2220
ggtgtttatt ttaaagctgg tggacctata acttataaag ttatgagaga agttagagcc    2280
ctggcttatt ttgttaatgg tactgcacaa gatgttattt tgtgtgatgg gtcacctaga    2340
ggcttgttag catgccagta taatactggc aatttttcag atggctttta tcctttttact    2400 aatagtagtt tagttaagca gaagtttatt gtctatcgtg aaaatagtgt taatactact    2460
tttacgttac acaatttcac ttttcataat gagactggcg ccaacccaaa tcctagtggt    2520
gtccagaata ttcaaactta ccaaacacaa acagctcaga gtggttatta taattttaat    2580
ttttcctttc tgagtagttt tgtttataag gagtctaatt ttatgtatgg atcttatcac    2640
ccaagttgta attttagact agaaactatt aataatggtt tgtggtttaa ttcactttca    2700
gttagtattg cttacggtcc tcttcaaggt ggttgcaagc aatctgtctt tagtggtaga    2760
gcaacctgtt gttatgctta ctcatatgga ggtcctttgc tgtgtaaagg tgtttattca    2820
ggtgagttag atcataattt tgaatgtgga ctgttagttt atgttactaa gagcggtggc    2880
tctcgtatac aaacagccac tgaaccgcca gttataactc aacacaatta taataatatt    2940
actttaaata cttgtgttga ttataatata tatggcagaa ctggccaggg ttttattact    3000
aatgtaaccg actcagctgt tagttataat tatctagcag acgcaggttt ggctatttta    3060
gatacatctg gttccataga catctttgtc gtacaaagtg aatatggtct taattattat    3120
aaggttaacc cttgcgaaga tgtcaaccag cagtttgtag tttctggtgg taaattagta    3180
ggtattctta cttcacgtaa tgagactggt tcccagcttc ttgagaatca gttttacatc    3240
aaaatcacta atggaacacg tcgttttaga cgttctatta ctgaaagtgt tgaaaattgc    3300
ccttatgtta gttatggtaa gttttgtata aaacctgatg gcagtattgc cacaatagta    3360
ccaaaacagt tagaacagtt tgtggcacct ttacttaatg ttactgaaaa tgtgctcata    3420
cctaacagtt ttaatttaac tgttacagat gagtacatac aaactcggat ggataaggtc    3480
caaattaatt gcctgcagta tatttgtggc aattctctgg agtgcagaaa tttgtttcaa    3540
caatatggtc ctgtttgcga caacatattg tctgtagtaa atagtgttgg tcaaaaagaa    3600
gatatggaac ttttgaattt ctattcttct actaagccgg ctggttttaa tacaccagtt    3660
```

-continued

```
cttagtaatg ttagcactgg tgagtttaat attactcttt ttttaacaac gcctagtagt      3720
cctagaaggc gttctttat tgaagacctt ctatttacaa gtgttgaatc tgttggatta       3780
ccaacagatg acgcatacaa aaattgcact gcaggtcctt taggctttct gaaagacctt      3840
gcatgtgctc gtgaatataa tggtttgctt gtgttgcctc ctattataac agcagaaatg      3900
caaactttgt atacaagctc tctagtagct tctatggctt ttggtggtat tactgcagct      3960
ggtgctatac cttttgccac acaactgcag gctagaatta atcacttggg tattacccag      4020
tcacttcttt tgaagaatca agaaaaaatt gctgcttcct ttaataaggc catcggtcat      4080
atgcaggaag gttttagaag tacatctttta gcattacaac aaattcaaga tgttgttaat      4140
aagcagagtg ctattcttac tgagactatg gcatcactta ataaaaattt tggtgccatt      4200
tcttctgtga ttcaagaaat ctaccagcaa cttgacgcca tacaagcaaa tgctcaagtg      4260
gatcgtctta taactggtag attgtcatca ctttctgttt tagcatctgc taagcaggcg      4320
gagtatatta gagtgtcaca acagcgtgag ttagctactc agaagattaa tgagtgtgtt      4380
aagtcacagt ccattaggta ctcctttttgt ggtaatggac gacatgtttt aaccataccg      4440
caaaatgcac ctaatggtat agtgtttata cacttttctt acactccaga tagttttgtt      4500
aatgttactg caatagtggg tttttgtgta aagccagcta atgctagtca gtatgcaata      4560
gtacccgcta atggtagggg tattttttata caagttaatg gtagttacta catcactgca      4620
cgagatatgt atatgccaag agctattact gcaggagata tagttacgct tacttcttgt      4680
caagcaaatt atgtaagtgt aaataagacc gtcattacta cattcgtaga caatgatgat      4740
tttgatttta atgacgaatt gtcaaaatgg tggaatgata ctaagcatga gctaccagac      4800
tttgacaaat tcaattacac agtacctata cttgacattg atagtgaaat tgatcgtatt      4860
caaggcgtta tacagggtct taatgactct ctaatagacc ttgaaaaact ttcaatactc      4920
aaaacttata ttaagtggcc ttggtatgtg tggctagcca tagcttttgc cactattatc      4980
ttcatcttaa tattaggatg ggttttcttc atgactgggt gttgtggttg ttgttgtgga      5040
tgctttggca ttatgcctct aatgagtaag tgtggtaaga aatcttctta ttacacgact      5100
tttgataacg atgtggtaac tgaacaatac agacctaaaa agtctgttta atgatccaaa      5160
gtcccactag tttcttaata gtattaattt tgctttggtg taaacttgta ctaagttgtt      5220
ttagagagtt tattattgcc cttcaacaac taacacaagt tttactccaa attatcgata      5280
gtaatttaca gtctagactg acccctttggc acagtctaga ctaatgttaa acttagaagc      5340
aattattgaa accggtgatc aagtgattca aaaaatcagt ttcaatttac agcatatttc      5400
aagtgtatta aacacagaag tatttgaccc ctttgactat tgttattaca gaggaggtaa      5460
tttttgggaa atagagtcag ctgaagattg ttcaggtgat gatgaattta ttgaataagt      5520
cgctagagga gaatggaagt tttctaacgg cactttacat atttgtagga tttttagcat      5580
tttatcttct aggtagagca cttcaagcat ttgtacaggc tgctgatgct tgttgtttat      5640
tttggtacac gtggttagta attccaggag ttaagggtac agcctttgta tacaagtata      5700
catatggtag aaaacttaac aattcggaat tagaagcagt tgttgttaac gagtttccta      5760
agaacggttg gaataataaa aatccagcaa attttcaaga tgtccaacga aacaaattgt      5820
actcttgact ttgaacagtc agttgagctt tttaaagagt ataatttatt tataactgca      5880
ttcttgttgt tcttaaccat aatacttcag tatggttatg caacgcgtag taagtttatt      5940
tatatactta aaatgatagt gttatggtgc ttttggcccc ttaacattgc agtaggtgta      6000
atttcatgta tatacccacc aaaacacagg ggtcttgtcg cagcgataat acttactgtg      6060
```

-continued

```
tttgcgtgtc tttctttttgt aggttattgg atccagagta ttagactctt taagcggtgt    6120
agatcttggt ggtcatttaa cccagaatct aacgccgtag gttcaatact cctaactaat    6180
ggtcaacaat gtaattttgc tatagagagt gtgccgatgg tgctttctcc tattataaag    6240
aatggtgttc tttattgtga gggtcagtgg cttgctaaat gtgaaccaga ccacttgcct    6300
aaagacatat ttgtatgcac accagataga cgtaatatct atcgtatggt gcagaaatac    6360
actggtgacc aaagcggaaa taagaaaagg tttgctacat ttgtctatgc aaagcagtca    6420
gtagacactg gcgagctaga aagtgtagca acaggtggaa gtagccttta cacataaatg    6480
tgtgtgtgta gagagtattt aaaattattc ttcaatagtg cctctatttt aagagcgcgg    6540
aagagtattt gttttgagga tattaatata aatcctcttt gttttgtact ctctttacaa    6600
gagttattat ttaagcaaca gtttttcctt tcctttgttt ggaagaaagt tgttgttaat    6660
ggtgtagaat ccaagtagaa aaatggaaaa gtccactacg aaggaaaccc cattttccaa    6720
aaaggttgtt gtaggttgtg gtcccattat aagaaggatt aaatggatta aaccacctac    6780
actacttact tgtaataagg gcgtttggac ttacaagcgc ttaacaaata cagacgatga    6840
aatggctgac tagttttgga agagcagtta tttcttgtta taaagcccta ctattaactc    6900
agttaagagt attagatagg ttaattttag atcacggacc aaagcgagtc ttaacgtgtg    6960
gtaggcgagt gcttttatct caattagatt tagtttatag gttggcatat acgcccaccc    7020
aatcgctggt atgaataata gtaaagataa tccttttcgc ggagcaatag caagaaaagc    7080
gcgaatttat ctgagagaag gattagagtg tgtttacttt cttaacaaag caggacaagc    7140
agagccttgt cccgcgtgta cctccctagt atttcagggg aaaacttgtg aggaacacac    7200
agataataat aatcttttgt catggcgagc ggtaagacaa ctgggaagac agacgcccca    7260
gcgccagtca tcaaactagg agggccaaaa ccacctaaag ttggttcttc tggaaatgct    7320
agctggtttc aagcactaaa agccaagaag ttaaattcac ctcctcctaa gtttgaaggt    7380
agcggcgttc ctgataatga aaatcttaaa ttaagccagc aacatgggta ctggagacgt    7440
caagccaggt acaagccagg taaaggcgga agaaaatcag tcccagatgc ttggtacttc    7500
tattacactg gaacaggacc agccgctgac ctgaattggg gtgatagcca agatggtata    7560
gtgtgggttt ctgcaaaggg tgctgatact aaatctagat ctaaccaggg tacaagggat    7620
cctgataagt ttgaccaata cccgctacga ttctcagatg gaggacctga tggtaatttc    7680
cgttgggact tcattccaat aaatcgtggt aggagtggaa gatcaacagc ggcttcatca    7740
gcagcatcta gtagagcacc gtcgcgtgat ggctcgcgtg gacgtagaag cggagctgaa    7800
gatgatctta tagctcgtgc agcaaagatc attcaggatc agcagaagaa gggttctcgc    7860
attactaaag ctaaggccga tgaaatggct catcgccggt attgtaagcg tactatccca    7920
cctggttata aggttgatca agtatttggt ccccgtacta aaggtaagga gggaaatttt    7980
ggtgatgaca agatgaatga ggagggtatt aaggatgggc gcgttacagc aatgctcaac    8040
ctagtcccta gcagccatgc ttgtcttttt ggaagtagag tgacgcccaa acttcaacca    8100
gatgggctgc acttgagatt tgaatttact actgtggttt ctaggatga tccgcagttt    8160 gataattatg tgaaaatttg tgatcagtgt gtcgatggta tagggactcg gccaaaagac    8220
gatgaaccga gaccaaagtc acgcccaaat tcaagacctg ctacaagaac aagttctcca    8280
gcgccaagac aacagcgtca aaagaaggag aagaagtcaa agaagcagga tgatgaagta    8340
gataaggcat tgacctcaga tgaggagagg aacaatgcac agctggaatt tgatgatgaa    8400
```

-continued

```
ccgaaagtga ttaactgggg ggattcagca cttggagaga atgagttgta aagctagatt      8460
tccaacttaa catcatggac gtgcgtatgc tgttttttccc tactatagac tttttagcat      8520
attatttttt gctatttgta tggtttatta caggtgaaga ttgtatgtat ttgttgtaca      8580
ctcgtatgtt ctatattatg ttttctgtag ttgttattag tgttgttctt gttcttactc      8640
tactgttctc ttttctttat tttagagtat caataagaat caaggaagat aggcatgtag      8700
tttgattacc tacatgtcta tcgccaggga aatgtctaat ctgtctactt agtagcctgg      8760
aaacgaacgg tagaccctta gattttaatt tagtttaatt tttagtttag tttaagttag      8820
tttagagtag gtataaagaa gccagtgccg gggccacgcg gagtacgatc gagggtacag      8880
cactaggacg cccactaggg gaagagctaa attttagttt aagttaagtt taattggcta      8940
agtatagtta aaatttatag gctagtatag agttagagca aaaaaaaaaa aaaaaaaaaa      9000
aaaaaaaaaa aaaaaaaaaa aaaaaaaaaa aaaaaaaaaa aaaaaaaaaa aaaaaaaaaa      9060
aaaaaaaaaa aaaaaaaaag tttaaactta attaagaatt cccttggctc gagttcgaaa      9120
tcggatgccg ggaccgacga gtgcagaggc gtgcaagcga gcttggcgta atcatggtca      9180
tagctgtttc ctgtgtgaaa ttgttatccg ctcacaattc cacacaacat acgagccgga      9240
agcataaagt gtaaagcctg gggtgcctaa tgagtgagct aactcacatt aattgcgttg      9300
cgctcactgc ccgctttcca gtcgggaaac ctgtcgtgcc agctgcatta atgaatcggc      9360
caacgcgcgg ggagaggcgg tttgcgtatt gggcgctctt ccgcttcctc gctcactgac      9420
tcgctgcgct cggtcgttcg ctgcggcga gcggtatcag ctcactcaaa ggcggtaata      9480
cggttatcca cagaatcagg ggataacgca ggaaagaaca tgtgagcaaa aggccagcaa      9540
aaggccagga accgtaaaaa ggccgcgttg ctggcgtttt tccataggct ccgcccccct      9600
gacgagcatc acaaaaatcg acgctcaagt cagaggtggc gaaacccgac aggactataa      9660
agataccagg cgtttccccc tggaagctcc ctcgtgcgct ctcctgttcc gaccctgccg      9720
cttaccggat acctgtccgc ctttctccct tcgggaagcg tggcgctttc tcatagctca      9780
cgctgtaggt atctcagttc ggtgtaggtc gttcgctcca agctgggctg tgtgcacgaa      9840
ccccccgttc agcccgaccg ctgcgcctta tccggtaact atcgtcttga gtccaacccg      9900
gtaagacacg acttatcgcc actggcagca gccactggta acaggattag cagagcgagg      9960
tatgtaggcg gtgctacaga gttcttgaag tggtggccta actacggcta cactagaaga    10020
acagtatttg gtatctgcgc tctgctgaag ccagttacct tcggaaaaag agttggtagc    10080
tcttgatccg gcaaacaaac caccgctggt agcggtggtt ttttttgtttg caagcagcag    10140 attacgcgca gaaaaaaagg atctcaagaa gatcctttga tcttttctac ggggtctgac    10200
gctcagtgga acgaaaactc acgttaaggg attttggtca tgagattatc aaaaaggatc    10260
ttcacctaga tccttttaaa ttaaaaatga agttttaaat caatctaaag tatatatgag    10320
taaacttggt ctgacagtta ccaatgctta atcagtgagg cacctatctc agcgatctgt    10380
ctatttcgtt catccatagt tgcctgactc cccgtcgtgt agataactac gatacgggag    10440
ggcttaccat ctggccccag tgctgcaatg ataccgcgag acccacgctc accggctcca    10500
gatttatcag caataaacca gccagccgga agggccgagc gcagaagtgg tcctgcaact    10560
ttatccgcct ccatccagtc tattaattgt tgccgggaag ctagagtaag tagttcgcca    10620
gttaatagtt tgcgcaacgt tgttgccatt gctacaggca tcgtggtgtc acgctcgtcg    10680
tttggtatgg cttcattcag ctccggttcc caacgatcaa ggcgagttac atgatccccc    10740
atgttgtgca aaaaagcggt tagctccttc ggtcctccga tcgttgtcag aagtaagttg    10800
```

```
gccgcagtgt tatcactcat ggttatggca gcactgcata attctcttac tgtcatgcca   10860
tccgtaagat gcttttctgt gactggtgag tactcaacca agtcattctg agaatagtgt   10920
atgcggcgac cgagttgctc ttgcccggcg tcaatacggg ataataccgc gccacatagc   10980
agaactttaa aagtgctcat cattggaaaa cgttcttcgg ggcgaaaact ctcaaggatc   11040
ttaccgctgt tgagatccag ttcgatgtaa cccactcgtg cacccaactg atcttcagca   11100
tcttttactt tcaccagcgt ttctgggtga gcaaaaacag gaaggcaaaa tgccgcaaaa   11160
aagggaataa gggcgacacg gaaatgttga atactcatac tcttcctttt tcaatattat   11220
tgaagcattt atcagggtta ttgtctcatg agcggataca tatttgaatg tatttagaaa   11280
aataaacaaa taggggttcc gcgcacattt ccccgaaaag tgccacctga cgtctaagaa   11340
accattatta tcatgacatt aacctataaa aataggcgta tcacgaggcc ctttcgtc     11398
```

<210> SEQ ID NO 11
<211> LENGTH: 1155
<212> TYPE: PRT
<213> ORGANISM: Avian infectious bronchitis virus

<400> SEQUENCE: 11

```
Met Leu Asp Lys Pro Leu Leu Leu Val Thr Leu Trp Tyr Ala Leu Cys
1               5                   10                  15

Ser Ala Leu Leu Tyr Asp Asn Asn Thr Tyr Val Tyr Tyr Gln Ser
            20                  25                  30

Ala Phe Arg Pro Gly Pro Gly Trp His Leu Tyr Gly Gly Ala Tyr Ala
        35                  40                  45

Val Asp Arg Val Phe Asn Glu Thr Asn Asn Ala Gly Ser Ala Ser Asp
    50                  55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
            100                 105                 110

His Cys Phe Lys Asn Gln Leu Gly Ser Cys Pro Leu Thr Gly Met Ile
        115                 120                 125

Pro Gln Asn His Ile Arg Ile Ser Ala Met Arg Asp Gly Val Leu Phe
        130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
                180                 185                 190

Lys Ser Gly Gly Pro Val Thr Tyr Lys Val Met Lys Glu Val Lys Ala
            195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Leu Lys Leu Thr
                260                 265                 270
```

-continued

```
Asn Phe Ser Phe Thr Asn Val Ser Asn Ala Ser Pro Asn Ser Gly Gly
        275                 280                 285

Val Asp Thr Phe Gln Leu Tyr Gln Thr Ser Thr Ala Gln Asp Gly Tyr
        290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr
        340                 345                 350

Tyr Gly Pro Ile Gln Gly Gly Cys Lys Gln Ser Val Phe Ser Asn Arg
        355                 360                 365

Ala Thr Cys Cys Tyr Ala Tyr Ser Tyr Gln Gly Pro Ser Arg Cys Lys
        370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
        420                 425                 430

Cys Val Glu Tyr Asn Ile Tyr Gly Arg Val Gly Gln Gly Phe Ile Thr
        435                 440                 445

Asn Val Thr Glu Ala Thr Ala Asn Tyr Ser Tyr Leu Ala Asp Gly Gly
        450                 455                 460

Leu Ala Ile Leu Asp Thr Ser Gly Ala Ile Asp Ile Phe Val Val Gln
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
                500                 505                 510

Ser His Asn Glu Thr Gly Ser Glu Ser Ile Glu Asn Gln Phe Tyr Ile
        515                 520                 525

Lys Leu Thr Asn Gly Thr Arg Arg Ser Arg Arg Ser Val Thr Gly Asn
        530                 535                 540

Val Thr Asn Cys Pro Tyr Val Ser Tyr Gly Lys Phe Cys Ile Lys Pro
545                 550                 555                 560

Asp Gly Ser Leu Ser Ile Ile Val Pro Gln Glu Leu Glu Gln Phe Val
                565                 570                 575

Ala Pro Leu Phe Asn Val Thr Glu His Val Leu Ile Pro Asp Ser Phe
                580                 585                 590

Asn Leu Thr Val Thr Asp Glu Tyr Ile Gln Thr Arg Met Asp Lys Val
        595                 600                 605

Gln Ile Ile Cys Leu Gln Tyr Val Cys Gly Asn Ser Ile Glu Cys Arg
        610                 615                 620

Lys Leu Phe Gln Gln Tyr Gly Pro Val Cys Asp Asn Ile Leu Ser Val
625                 630                 635                 640

Val Asn Gly Val Gly Gln Arg Glu Asp Met Glu Leu Leu Ser Phe Tyr
                645                 650                 655

Ser Ser Thr Lys Pro Ser Gly Tyr Asn Thr Pro Ile Phe Asn Asn Val
                660                 665                 670

Ser Thr Gly Asp Phe Asn Ile Ser Leu Leu Leu Thr Pro Pro Asn Ser
        675                 680                 685
```

```
Pro Thr Gly Arg Ser Phe Ile Glu Asp Leu Leu Phe Thr Ser Val Glu
    690             695             700

Ser Val Gly Leu Pro Thr Asp Glu Glu Tyr Lys Lys Cys Thr Ala Gly
705             710             715             720

Pro Leu Gly Phe Val Lys Asp Leu Val Cys Ala Arg Glu Tyr Asn Gly
            725             730             735

Leu Leu Val Leu Pro Pro Ile Ile Thr Ala Glu Met Gln Thr Met Tyr
            740             745             750

Thr Ser Ser Leu Val Ala Ser Met Ala Leu Gly Gly Ile Thr Ala Ala
        755             760             765

Gly Ala Ile Pro Phe Ala Thr Gln Leu Gln Ala Arg Ile Asn His Leu
    770             775             780

Gly Ile Thr Asn Ser Leu Leu Leu Lys Asn Gln Glu Lys Ile Ala Ala
785             790             795             800

Ser Phe Asn Lys Ala Ile Gly His Met Gln Glu Gly Phe Lys Ser Thr
            805             810             815

Ser Leu Ala Leu Gln Gln Ile Gln Asp Val Val Asn Lys Gln Ser Ser
            820             825             830

Ile Leu Thr Glu Thr Met Gln Ser Leu Asn Lys Asn Phe Gly Ala Ile
        835             840             845

Ser Ser Val Ile Gln Asp Ile Tyr Gln Gln Leu Asp Ala Ile Gln Ala
    850             855             860

Asp Ala Gln Val Asp Arg Leu Ile Thr Gly Arg Leu Ser Ser Leu Ser
865             870             875             880

Val Leu Ala Ser Ala Lys Gln Ala Glu Tyr His Arg Val Ser Gln Gln
            885             890             895

Arg Glu Leu Ala Thr Gln Lys Ile Asn Glu Cys Val Lys Ser Gln Ser
            900             905             910

Asn Arg Tyr Ser Phe Cys Gly Asn Gly Arg His Val Leu Thr Ile Pro
        915             920             925

Gln Asn Ala Pro Asn Gly Ile Val Phe Ile His Phe Thr Tyr Thr Pro
    930             935             940

Glu Ser Phe Val Asn Val Thr Ala Ile Val Gly Phe Cys Val Asn Pro
945             950             955             960

Ala Asn Ala Ser His Tyr Ala Ile Val Pro Val Asn Gly Arg Gly Val
            965             970             975

Phe Ile Glu Val Asn Gly Ser Tyr Tyr Ile Thr Ala Arg Asp Met Tyr
            980             985             990

Met Pro Arg Asp Ile Thr Ala Gly Asp Ile Val Thr Leu Thr Ser Cys
        995             1000            1005

Gln Ala Asn Tyr Val Asn Val Asn Lys Thr Val Ile Asn Thr Phe
    1010            1015            1020

Val Glu Asp Asp Asp Phe Asp Phe Tyr Asp Glu Leu Ser Lys Trp
    1025            1030            1035

Trp Asn Asp Thr Lys His Glu Leu Pro Asp Phe Asp Glu Phe Asn
    1040            1045            1050

Tyr Thr Val Pro Val Leu Asn Ile Ser Asn Glu Ile Asp Arg Ile
    1055            1060            1065

Gln Gln Val Ile Gln Gly Leu Asn Asp Ser Leu Ile Asp Leu Glu
    1070            1075            1080

Thr Leu Ser Ile Leu Lys Thr Tyr Ile Lys Trp Pro Trp Tyr Val
    1085            1090            1095

Trp Leu Ala Ile Ala Phe Leu Thr Ile Ile Phe Ile Leu Val Leu
```

-continued

```
       1100          1105          1110

Cys Trp Ile Phe Phe Met Thr Gly Cys Cys Gly Cys Cys Cys Gly
    1115          1120          1125

Cys Phe Gly Ile Ile Pro Leu Met Ser Lys Cys Gly Lys Lys Ser
    1130          1135          1140

Ser Tyr Tyr Thr Thr Phe Asp Asn Asp Val Val Thr
    1145          1150          1155

<210> SEQ ID NO 12
<211> LENGTH: 11860
<212> TYPE: DNA
<213> ORGANISM: Artificial Sequence
<220> FEATURE:
<223> OTHER INFORMATION: Plasmid Sequence

<400> SEQUENCE: 12
tcgcgcgttt cggtgatgac ggtgaaaacc tctgacacat gcagctcccg gagacggtca         60
cagcttgtct gtaagcggat gccgggagca gacaagcccg tcagggcgcg tcagcgggtg        120
ttggcgggtg tcggggctgg cttaactatg cggcatcaga gcagattgta ctgagagtgc        180
accatatgcg gtgtgaaata ccgcacagat gcgtaaggag aaaataccgc atcaggcgcc        240
attcgccatt caggctgcgc aactgttggg aagggcgatc ggtgcgggcc tcttcgctat        300
tacgccagct ggcgaaaggg ggatgtgctg caaggcgatt aagttgggta cgccagggt        360 tttcccagtc acgacgttgt aaaacgacgg ccagtgaatt ggagatcggt acttcgcgaa        420
tgcgtcgaga tgagctctaa tacgactcac tataggact taagtgtgat ataaatatat        480
atcatacata ctagccttgt gctagatttc aacttaaca aaacggactt aaataccac         540 agttggtccc tataggtgtt ccattgcagt gcactttagt gccctggatg gcacctggcc        600
acctgtcagg tttttgttat aaaataata ttgttgctgg tatcactgct tgttttgccg        660
tgtctcactt tatacatccg ttgcttgggc tacctagtat ccagcgtcct actggcgttg        720
tggtcggttc gagtgcgaag aacctctggt tcatctagcg gtacgcgggt gtgtggaagt        780
agcgcttcag acgtaccggt tctgttgcgt gaaatacggg gtcacctccc cccacatacc        840
tctaagggct tttgagccta gcgttgggct acgttctcgc acaaggtcgg ctatacggcg        900
tttgtagggg gtagtgccaa acaacccctg aggtgacagg ttctggtggt gtttcgaaaa        960
caacaatgtg tgtgccgcat aatatgcgag taatgcattt tggagcagga agtgacaaag       1020
gagtggcccc aggtagcgct gttcttaggc agtggcttcc cgaaggtaca ctccttgtcg       1080
ataatgatat tgtagattat gtatctgatg cacatgtctc tgtgctttca gattgcaata       1140
aatgtaaaac agagcacaag tttgatcttg tgatatctga tatgtataca gataatgatt       1200
caaagagaaa gcatgaaggc gttgtagcca ataacggcaa tgatgacgtc ttcatatacc       1260
tttcaaactt tcttcgtaac aatttagctc tgggaggcag ttttgccgta aaagtaacag       1320
agacaagttg gcatgagagt ttatatgaca ttgcacagga ttgtgcatgg tggacaatgt       1380
tttgtacagc agtgaatgct tcttcgtcag aagcattctt gattggtgtt aattatttgg       1440
gtgcaagtga aaaggttaga gttagtggta aaaccctgca cgcaaattat atattttgga       1500
ggaattgtaa ttatttacaa acttcagcct atagtatatt tgacgttgct aagtttgatt       1560
tgaaattaaa agcaacgcca gttgtgaatt tgaaaactga acaaaagaca gacttagtct       1620
ttaatttaat taagtgtggt aagttactgg taagagatgt tggacaaacc gcttttacta       1680
gtgactcttt ggtatgcact atgtagtgct ttgctctatg ataataatta tattggtgat      1740
```

-continued

```
tttagatgta tccagcttgt gaactcaaac ggtgctaatg ttagtgctcc aagcattagc      1800
actgagaccg ttgaagtttc acaaggcctg gggacatatt atgtgttaga tcgagtttat      1860
ttaaatgcca cattattgct tactggttac tacccggtcg atggttctaa gtttagaaac      1920
ctcgctctta cgggaactaa ctcagttagc ttgtcgtggt ttcaaccacc ctatttaagt      1980
cagtttaatg atggcatatt tgcgaaggtg cagaacctta agacaagtac gccatcaggt      2040
gcaactgcat attttcctac tatagttata ggtagtttgt ttggctatac ttcctatacc      2100
gttgtaatag agccatataa tggtgttata atggcctcag tgtgccagta taccatttgt      2160
cagttacctt acactgattg taagcctaac actaatggta ataagcttat agggttttgg      2220
cacacggatg taaaaccccc aatttgtgtg ttaaagcgaa atttcacgct taatgttaat      2280
gctgatgcat tttattttca tttttaccaa catggtggta cttttttatgc gtactatgcg      2340 gataaaccct ccgctactac gttttttgttt agtgtatata ttggcgatat tttaacacag      2400
tattatgtgt tacctttcat ctgcaaccca acagctggta gcactttttgc tccgcgctat      2460 tgggttacac ctttggttaa gcgccaatat ttgtttaatt tcaaccagaa gggtgtcatt      2520
actagtgctg ttgattgtgc tagtagttat accagtgaaa taaaatgtaa gacccagagc      2580
atgttaccta gcactggtgt ctatgagtta tccggttata cggtccaacc agttggagtt      2640
gtataccggc gtgttgctaa cctcccagct tgtaatatag aggagtggct tactgctagg      2700
tcagtcccct cccctctcaa ctgggagcgt aagacttttc agaattgtaa ttttaattta      2760
agcagcctgt tacgttatgt tcaggctgag agtttgtttt gtaataatat cgatgcttcc      2820 aaaagtgtatg gcaggtgctt tggtagtatt tcagttgata agtttgctgt accccgaagt      2880
aggcaagttg atttacagct tggtaactct ggatttctgc agactgctaa ttataagatt      2940
gatacagctg ccacttcgtg tcagctgcat tacaccttgc ctaagaataa tgtcaccata      3000
aacaaccata acccctcgtc ttggaatagg aggtatggct ttaatgatgc tggcgtctttt     3060 ggcaaaaacc aacatgacgt tgtttacgct cagcaatgtt ttactgtaag atctagttat      3120
tgcccgtgtg ctcaaccgga catagttagc ccttgcacta ctcagactaa gcctaagtct      3180
gcttttgtta atgtgggtga ccattgtgaa ggcttaggtg ttttagaaga taattgtggc      3240
aatgctgatc cacataaggg ttgtatctgt gccaacaatt catttattgg atggtcacat      3300
gatacctgcc ttgttaatga tcgctgccaa attttttgcta atatattgtt aaatggcatt      3360
aatagtggta ccacatgttc cacagatttg cagttgccta atactgaagt ggttactggc      3420
atttgtgtca aatatgacct ctacggtatt actggacaag gtgtttttaa agaggttaag      3480
gctgactatt ataatagctg gcaaaccctt ctgtatgatg ttaatggtaa tttgaatggt      3540
tttcgtgatc ttaccactaa caagacttat acgataagga gctgttatag tggccgtgtt      3600
tctgctgcat ttcataaaga tgcacccgaa ccggctctgc tctatcgtaa tataaaattgt     3660 agctatgttt ttagcaataa tatttcccgt gaggagaacc cacttaatta ctttgatagt      3720
tatttgggtt gtgttgttaa tgctgataac cgcacggatg aggcgcttcc taattgtgat      3780
ctccgtatgg gtgctggctt atgcgttgat tattcaaaat cacgcagggc tcaccgatca      3840
gtttctactg gctatcggtt aactacattt gagccataca ctccgatgtt agttaatgat      3900
agtgtccaat ccgttgatgg attatatgag atgcaaatac caaccaattt tactattggg      3960
caccatgagg agttcattca aactagatct ccaaaggtga ctatagattg tgctgcattt      4020
gtctgtggta ataacactgc atgcaggcag cagttggttg agtatggctc tttctgtgtt      4080
aatgttaatg ccattcttaa tgaggttaat aacctcttgg ataatatgca actacaagtt      4140
```

-continued

```
gctagtgcat taatgcaggg tgttactata agttcgagac tgccagacgg catctcaggc      4200
cctatagatg acattaattt tagtcctcta cttggatgca taggttcaac atgtgctgaa      4260
gacggcaatg gacctagtgc aatccgaggg cgttctgcta tagaggattt gttatttgac      4320
aaggtcaaat tatctgatgt tggctttgtc gaggcttata ataattgcac cggtggtcaa      4380
gaagttcgtg acctcctttg tgtacaatct tttaatggca tcaaagtatt acctcctgtg      4440
ttgtcagaga gtcagatctc tggctacaca accggtgcta ctgcggcagc tatgttccca      4500
ccgtggtcag cagctgccgg tgtgccattt agtttaagtg ttcaatatag aattaatggt      4560
ttaggtgtca ctatgaatgt gcttagtgag aaccaaaaga tgattgctag tgcttttaac      4620
aatgcgctgg gtgctatcca ggatgggttt gatgcaacca attctgcttt aggtaagatc      4680
cagtccgttg ttaatgcaaa tgctgaagca ctcaataact tactaaatca actttctaac      4740
aggtttggtg ctattagtgc ttctttacaa gaaattctaa ctcggcttga ggctgtagaa      4800
gcaaaagccc agatagatcg tcttattaat ggcaggttaa ctgcacttaa tgcgtatata      4860
tccaagcaac ttagtgatag tacgcttatt aaagttagtg ctgctcaggc catagaaaag      4920
gtcaatgagt gcgttaagag ccaaaccacg cgtattaatt tctgtggcaa tggtaatcat      4980
atattatctc ttgtccagaa tgcgccttat ggcttatatt ttatacactt cagctatgtg      5040
ccaatatcct ttacaaccgc aaatgtgagt cctggacttt gcattctgg tgatagagga      5100 ttagcaccta aagctggata tttttgttcaa gatgatggag aatggaagtt cacaggcagt      5160
tcatattact accctgaacc cattacagat aaaaacagtg tcattatgag tagttgcgca      5220
gtaaactaca caaaggcacc tgaagttttc ttgaacactt caatacctaa tccacccgac      5280
tttaaggagg agttagataa atggtttaag aatcagacgt ctattgcgcc tgatttatct      5340
ctcgatttcg agaagttaaa tgttactttg ctggacctga cgtatgagat gaacaggatt      5400
caggatgcaa ttaagaagtt aaatgagagc tacatcaacc tcaaggaagt tggcacatat      5460
gaaatgtatg tgaaatggcc ttggtatgtg tggcttgcca ttgcattcct taccattatt      5520
tttattctgg tactttgttg gatatttttc atgaccggtt gttgcggttg ttgttgtgga      5580
tgctttggta tcataccgtt aatgagtaag tgtggtaaga atcttcttta ctacacgact      5640
tttgataatg atgtggtaac ttaacaatac agacctaaaa agtctgttta atgattaaaa      5700
gtcccacatc ttttctaata ttattaattc ttctttggtg taaacttgca ttaagttgtt      5760
ttaaagagtg tgttataaca ctccagcaac tagtacaaat tttactccaa attattaata      5820
gtaacttaca atctagactt ctgctttggc acagtctaga ctaatgttag attttgaagc      5880
aattattgaa actggtcagc aaataactca acaaattagt ttctatttac agcatatttc      5940
aagggtgcta agtactgaat tatttgaccc ctttgaagtt tgtgtttaca gaggaggtaa      6000
ttgttgggag ttagagtcag ctgacgagtt ttcaggtgat gacgaatata ttgagtagat      6060
cgctcgagga gaacggaagt tttctaacag cggtttacgt gtttttagga tttttagcac      6120
tttatctact aggtagagcg cttcaagctt ttgtacaagc ggctgacgct tgttgtcttt      6180
tttggtatac atgggtagta gttcctggag ccaagggcac agcctttgtt tataatcata      6240
catatggtaa aaaacttaac aaaccggagt tagaaacggt tattgttaac gaatttccaa      6300
aaaacggttg gaaatatgga taataccatc aattgtactc ttggtactga acaagcagtt      6360
cagcttttta aggaatataa tctgtttgta actgcattcc tgttgttttt aaccatacta      6420
cttcagtatg gatacgcaac taggagcaag gttatttaca tactgaaaat gatagtgtta      6480
```

-continued

```
tggtgctttt ggcccccttaa cattgcagta ggtgtaatct catgtatata cccaccaaac    6540
acaggaggtc ttgtcgcagc gataattctt acagtgtttg cgtgtctttc ttttataggt    6600
tattggatcc agagtattag actttttaag cggtgcaggt catggtggtc atttaacccc    6660
gaatctaatg ccgtaggttc aatactccta actaatggtc aacaatgtaa ttttgctata    6720
gagagtgtgc cgatggtgct ttctcctatt ataaagaatg gtgctcttta ttgcgagggt    6780
cagtggcttg ctaaatgtga accagaccac ttgcctagag atatatttgt atgcacaccg    6840
gatagacgta atatctatcg tatggtgcaa aaatatactg gtgaccaaag cggaagtaag    6900
aaaaggtttg ccacatttgt ctatgcaaag cagtcagtag atactggcga gctagaaagt    6960
gtgtcagcag taggaggtag tctttacaca taaatgtgtg tgtgtagaga gtatttaaaa    7020
ttattctttg acagtgcctc cgtttttaaga gcgcggaaga gtattatttt tgaggatatt    7080
aatataaatc ctctttgttt catactctcc tttcaggagt tattatttaa aaaacagttt    7140
ttccactctt ttgtgccaaa aacaattgtt gttaatggtg taacctttca ggtagacaat    7200
ggaaaagtct actacgaagg aagaccaatt ttccaaaaag gttgttgtag tttgtggtcc    7260
aattataaga aagattagaa taattaaacc acctacaaca cttatttta caaatggcgt    7320 tttaggttac aaacgcttaa caaatacgga tgatgaaatg gctgactagt tttggaagag    7380
ctttcatctc ctgttataaa tccctattac taactcaatt aagagtatta gataggttaa    7440
ttttagatca cggacccaag cgcacattaa cgtgtgctag gcgagtgctt ttagttcaat    7500
tagatttagt ttataggttg gcttatacgc ccacccaatc gctggtatga ataatagtaa    7560
agataatcct tttcgcggag caatagcaag aaaagcgcga atttatctga gaggaggatt    7620
agattgtgtt tactttctta acaaagcagg acaagcagag ccttgtcccg cgtgtacctc    7680
cctagtattc caagggaaaa cttgtgagga acactattat aataacaatc ttttgtcatg    7740
gcaagcggta aggcaactgg aaagacagac gccccagcgc cagtcatcaa actaggagga    7800
ccaaagccac ctaaagttgg ttcttctgga aatgcatcat ggtttcaacc gataaaggcc    7860
aagaagctaa attcacctgt gcctaaattt gacggtagtg gtgttcctga aaatgaaaat    7920
ctcaagtcaa gccagcaaca tggatactgg agacgccaac acaggttaa gcctggcaaa    7980 ggtggaagaa aaccagtccc tgatgcttgg tactttact acactggaac aggaccggcc    8040
gccgacctga attggggtga aactcaagat ggtatagtgt gggttgctgc aaagggtgct    8100
gatactaaat ctagatcaaa ccagggtaca agggatcctg ataagtttga ccaatacccca    8160 ctacgattct cagatggagg accggatggt aatttccgtt gggacttcat accaataaat    8220
cgtggtagga gtgggagatc aacagcagct tcatcagcag catctagtag agcaccatct    8280
cgtgaggggt cacgtggacg tagaagcgga gttgaagatg atcttatagc tcgcgcagca    8340
aagattatac aggaccagca aaagaagggt gcgcgcatta ccaaggctaa ggctgatgaa    8400
atggctcatc gccgctattg caagcgcact atcccacctg gttataaggt tgagcaagta    8460
tttggtcccc gtactaaagg taaggaagga aattttggtg atgacaagat gaatgaggaa    8520
ggtgttaagg atgggcgtgt tacggcaatg ctcaacctag tccctagcag tcatgcttgt    8580 cttttttggaa gtaggggtgac gcccaaactg cagccagatg gtcttcacct gagatttgaa    8640
tttactactg tggtgtcacg tgatgatccg cagtttgata attatgtgaa aatttgtgat    8700
cagtgtgtcg atggtgtagg gacgcgtcca aaggacgatg aatcgagacc aaagtcacgc    8760
ccaaattcaa gacctgcaac tagaggaaat tctccagcgc cgagacaaca gcgcccaaag    8820
aaggagaaaa agcccaagaa gcaggatgat gaagtagata aggcattgac ctcagatgag    8880
```

-continued

```
gagaggaaca atgcacagct ggaatttgat gatgaaccca aggtgattaa ctggggggac    8940
tctgcactag gtgaaaatga actttgatta acataatgga cttgctgcat ttgctgtcac    9000
attttgttaa atattatttt tgtgttttac tatcaattat tacaggtatt gattgtgatt    9060
atgttcaata cttaagcttc ttctggttgc tttttgcttg ttgtattgtt gctgtgcttt    9120
ttattattgt gattctcatt agtttgcttt atcgtagaaa ttcaatagta agagttaagg    9180
aagataggca tgtagcttag cacctacatg tctatcgcca gggaaatgtc taatctgtct    9240
acttagtagc ctggaaacga acggtagacc cttagatttt aatttagttt aatttttagt    9300
ttagtttaag ttagtttaga gtaggtataa agatgccagt gccggggcca cgcgtagtac    9360
daccgagggt acagcactag gacgcccact aggggaagag ctaaatttta gtttaagtta    9420
agtttaattg gctaaatata gttaaaattt ataggctagt atagagttag agcaaaaaaa    9480
aaaaaaaaaa aaaaaaaaaa aaaaaaaaaa aaaaaaaaaa aaaaaaaaaa aaaaaaaaaa    9540
aaaaaaaaaa aaaaaaaaaa aaaaaaaaaa aaagcggccg catcggatgc cgggaccgac    9600
gagtgcagag gcgtgcaagc gagcttggcg taatcatggt catagctgtt tcctgtgtga    9660
aattgttatc cgctcacaat tccacacaac atacgagccg gaagcataaa gtgtaaagcc    9720
tggggtgcct aatgagtgag ctaactcaca ttaattgcgt tgcgctcact gcccgctttc    9780
cagtcgggaa acctgtcgtg ccagctgcat taatgaatcg gccaacgcgc ggggagaggc    9840
ggtttgcgta ttgggcgctc ttccgcttcc tcgctcactg actcgctgcg ctcggtcgtt    9900
cggctgcggc gagcggtatc agctcactca aaggcggtaa tacggttatc cacagaatca    9960
ggggataacg caggaaagaa catgtgagca aaaggccagc aaaaggccag gaaccgtaaa    10020
aaggccgcgt tgctggcgtt tttccatagg ctccgccccc ctgacgagca tcacaaaaat    10080
cgacgctcaa gtcagaggtg gcgaaacccg acaggactat aaagatacca ggcgtttccc    10140
cctggaagct ccctcgtgcg ctctcctgtt ccgaccctgc cgcttaccgg atacctgtcc    10200
gcctttctcc cttcgggaag cgtggcgctt tctcatagct cacgctgtag gtatctcagt    10260
tcggtgtagg tcgttcgctc caagctgggc tgtgtgcacg aacccccccgt tcagcccgac    10320 cgctgcgcct tatccggtaa ctatcgtctt gagtccaacc cggtaagaca cgacttatcg    10380
ccactggcag cagccactgg taacaggatt agcagagcga ggtatgtagg cggtgctaca    10440
gagttcttga gtggtggcc taactacggc tacactagaa gaacagtatt tggtatctgc    10500
gctctgctga agccagttac cttcggaaaa agagttggta gctcttgatc cggcaaacaa    10560
accaccgctg gtagcggtgg tttttttgtt tgcaagcagc agattacgcg cagaaaaaaa    10620
ggatctcaag aagatccttt gatcttttct acggggtctg acgctcagtg gaacgaaaac    10680
tcacgttaag ggattttggt catgagatta tcaaaaagga tcttcaccta gatccttta    10740 aattaaaaat gaagttttaa atcaatctaa agtatatatg agtaaacttg gtctgacagt    10800
taccaatgct taatcagtga ggcacctatc tcagcgatct gtctatttcg ttcatccata    10860
gttgcctgac tccccgtcgt gtagataact acgatacggg agggcttacc atctggcccc    10920
agtgctgcaa tgataccgcg agacccacgc tcaccggctc cagatttatc agcaataaac    10980
cagccagccg gaagggccga gcgcagaagt ggtcctgcaa ctttatccgc ctccatccag    11040
tctattaatt gttgccggga agctagagta agtagttcgc cagttaatag tttgcgcaac    11100
gttgttgcca ttgctacagg catcgtggtg tcacgctcgt cgtttggtat ggcttcattc    11160
agctccggtt cccaacgatc aaggcgagtt acatgatccc ccatgttgtg caaaaaagcg    11220
```

-continued

```
gttagctcct tcggtcctcc gatcgttgtc agaagtaagt tggccgcagt gttatcactc   11280
atggttatgg cagcactgca taattctctt actgtcatgc catccgtaag atgcttttct   11340
gtgactggtg agtactcaac caagtcattc tgagaatagt gtatgcggcg accgagttgc   11400
tcttgcccgg cgtcaatacg ggataatacc gcgccacata gcagaacttt aaaagtgctc   11460
atcattggaa aacgttcttc ggggcgaaaa ctctcaagga tcttaccgct gttgagatcc   11520
agttcgatgt aacccactcg tgcacccaac tgatcttcag catcttttac tttcaccagc   11580
gtttctgggt gagcaaaaac aggaaggcaa aatgccgcaa aaaagggaat aagggcgaca   11640
cggaaatgtt gaatactcat actcttcctt tttcaatatt attgaagcat ttatcagggt   11700
tattgtctca tgagcggata catatttgaa tgtatttaga aaaataaaca aataggggtt   11760
ccgcgcacat ttccccgaaa agtgccacct gacgtctaag aaaccattat tatcatgaca   11820
ttaacctata aaaataggcg tatcacgagg ccctttcgtc                          11860
```

<210> SEQ ID NO 13
<211> LENGTH: 6905
<212> TYPE: DNA
<213> ORGANISM: Artificial Sequence
<220> FEATURE:
<223> OTHER INFORMATION: Plasmid Sequence

<400> SEQUENCE: 13

```
ttaattaagt gtggtaagtt actggtaaga gatgttggac aaaccgcttt tactagtgac     60
tctttggtat gcactatgta gtgctttgct ctatgataat aatacttacg tttactacta    120
ccaaagtgcc tttaggcctg gtccaggttg gcacctatat gggggtgctt atgcagtaga    180
tagggttttt aatgaaacca acaatgcagg cagtgcatct gattgcactg ctggtacttt    240
ttatgaaagc cataatattt ctgcttcttc tgtagccatg acagtaccac ataatggtat    300
gtcttggtca gcttcacaat tttgtacagc tcattgtaac ttctcagact ttacagtgtt    360
cgttacgcat tgtttttaaaa atcaactcgg tagttgtccc ttgacaggta tgattcctca   420
gaatcatatt cgtatttctg ctatgagaga tggagttttg ttttataact taacagttag    480
cgtatctaaa taccctagat ttaaatcgct tcaatgtgtt agcaattcta catctgtcta    540
tgtaaatggt gaccttgttt tcacttctaa tgaaacttct tacgttacgg gtgcaggcgt    600
ttattttaaa agtggtgggc ctgtaactta taaagttatg aaagaagtta aagccctagc    660
ctactttatt aatggtaccg cacaagaggt tattttatgt gataactcac ctagaggttt    720
gcttgcatgt cagtataaca ctggtaattt ttcagatgga ttctacccct ttactaatca    780
ttctttagtt aaggataggt ttattgtata tcgagaaagt agcactaaca ctactttaaa    840
gttaactaat ttcagtttta ctaatgtaag taatgcttct cctaattcag gtggcgttga    900
tactttccaa ttatatcaaa caagtactgc tcaggatggt tattataatt ttaatttatc    960
atttctgagt agttttgtgt ataaaccatc tgatttatg tatgggtcat accacccaca    1020
ttgtaagttt agaccagaga atattaataa tggcttatgg tttaattcat tatctgtgtc    1080
acttacttac ggacccattc aaggtggttg taagcaatct gttttttagta atagagcaac   1140 ttgttgctat gcttattctt atcaagggcc tagtagatgt aagggtgttt atagagggga   1200
gctaacgcaa tactttgaat gtggacttct agtttacgta actaagagtg atggctctcg   1260
tatacaaact agaagtgaac cactggtgtt aactcaatat aattataaca acattacttt   1320
aaataagtgt gttgagtata atatatatgg tagggttggt caaggtttta ttactaatgt   1380
aactgaagca actgctaatt atagttatct agcagatggt ggtttagcta ttttagatac   1440
```

```
ctcaggagcc atagacatat ttgttgttca aggtgcatat ggtcttaatt attataaggt      1500
taatccctgt gaagatgtta accaacagtt tgtagtgtct ggtggcaact tagttggcat      1560
tcttacatct cataatgaaa caggttctga atctattgag aaccagtttt acatcaaact      1620
cactaacgga acacgtcgct ctagacgttc tgttactggg aatgttacaa attgcccta       1680 tgttagttat ggcaagtttt gtataaaacc agatggttct ttatctataa tagtaccaca      1740
agaattagaa cagtttgtgg cgcctttatt caatgttact gagcatgtgc tcatacctga      1800
tagttttaat ttaactgtca cagatgagta catacaaact cgtatggata aggttcaaat      1860
tatttgcctt cagtatgttt gtggtaattc tattgaatgc agaaagttgt ttcagcagta      1920
tggacctgtt tgtgataata tattgtctgt tgtaaatggt gtaggtcaaa gagaggatat      1980 ggaacttta agtttctatt cttctactaa acctagtggg tacaatacac caattttaa       2040 taatgttagc actggtgact ttaatatttc gctcctacta acaccaccta atagtcctac      2100
tgggcgctct tttattgaag atcttctctt tacaagtgta gaatctgttg gattaccaac      2160
tgatgaagag tataaaaagt gtacagcagg acctttaggt tttgttaaag accttgtttg      2220
tgctagagag tataatggtt tgctcgttct gcctcctatt attactgcgg aaatgcaaac      2280
catgtatact agttctttag tagcctctat ggctttaggt ggcattactg cagctggtgc      2340 tataccttt gctacacaac tgcaggccag aattaaccat ttgggtatta ctaattctct       2400
tttgttgaaa aaccaagaaa aaattgctgc ttcctttaat aaggccatcg gtcatatgca      2460
ggaagggttt aaaagtactt ctctagcatt acaacagatt caagatgttg ttaataaaca      2520
gagttctatt cttacagaga ctatgcaatc acttaataaa aattttggtg ctatttcctc      2580
tgtaattcaa gacatttacc agcaactaga tgctattcag gcagatgctc aggttgatcg      2640
tcttattaca ggtagactct cttcactatc tgttttagct tctgctaaac aggcagagta      2700
tcatagagtg tcacaacagc gtgagttggc cactcagaaa attaatgagt gtgttaagtc      2760
tcagtctaat aggtattcat tttgtggtaa tggtagacat gttctaacca taccacagaa      2820
tgcacccaat ggcatagtgt ttatacactt tacatacact ccagagagtt ttgttaatgt      2880
tacggcaata gtagggtttt gcgtaaaccc agctaatgct agtcattatg caatagtgcc      2940
tgttaatggc aggggtgttt ttatagaagt taatggtagt tactatatca ctgctcgtga      3000
tatgtatatg ccaagagata ttactgcagg agacatagtc actttgactt cttgtcaagc      3060
aaactatgtt aatgtaaata aaaccgtcat taacacttt gtggaagatg acgatttga       3120 tttttatgat gaattgtcaa aatggtggaa tgatactaag catgagctac cagattttga      3180
tgaattcaat tataccgttc cagtttttaaa tattagtaat gaaattgaca gaattcaaca     3240
ggttattcag ggattaaatg attccctaat agaccttgaa acactctcaa ttctcaaaac      3300
ttatattaaa tggccttggt atgtgtggct tgccattgca ttccttacca ttatttttat      3360
tctggtactt tgttggatat ttttcatgac cggttgttgc ggttgttgtt gtggatgctt      3420
tggtatcata ccgttaatga gtaagtgtgg taagaaatct tcttactaca cgacttttga      3480
taatgatgtg gtaacttaac aatacagacc taaaaagtct gtttaatgat taaaagtccc      3540
acatcttttc taatattatt aattcttctt tggtgtaaac ttgcattaag ttgttttaaa      3600
gagtgtgtta taacactcca gcaactagta caaatttac tccaaattat taatagtaac        3660
ttacaatcta gacttctgct ttggcacagt ctagactaat gttagatttt gaagcaatta      3720
ttgaaactgg tcagcaaata actcaacaaa ttagtttcta tttacagcat atttcaaggg      3780
```

-continued

```
tgctaagtac tgaattattt gaccccttcttg aagtttgtgt ttacagagga ggtaattgtt   3840
gggagttaga gtcagctgac gagttttcag gtgatgacga atatattgag tagatcgctc   3900
gagaatcact agtgcggccg cctgcaggtc gaccatatgg gagagctccc aacgcgttgg   3960
atgcatagct tgagtattct atagtgtcac ctaaatagct tggcgtaatc atggtcatag   4020
ctgtttcctg tgtgaaattg ttatccgctc acaattccac acaacatacg agccggaagc   4080
ataaagtgta aagcctgggg tgcctaatga gtgagctaac tcacattaat tgcgttgcgc   4140
tcactgcccg ctttccagtc gggaaacctg tcgtgccagc tgcattaatg aatcggccaa   4200
cgcgcgggga gaggcggttt gcgtattggg cgctcttccg cttcctcgct cactgactcg   4260
ctgcgctcgg tcgttcggct gcggcgagcg gtatcagctc actcaaaggc ggtaatacgg   4320
ttatccacag aatcagggga taacgcagga aagaacatgt gagcaaaagg ccagcaaaag   4380
gccaggaacc gtaaaaaggc cgcgttgctg gcgtttttcc ataggctccg cccccctgac   4440
gagcatcaca aaaatcgacg ctcaagtcag aggtggcgaa acccgacagg actataaaga   4500
taccaggcgt ttccccctgg aagctccctc gtgcgctctc ctgttccgac cctgccgctt   4560
accggatacc tgtccgcctt tctcccttcg ggaagcgtgg cgctttctca tagctcacgc   4620
tgtaggtatc tcagttcggt gtaggtcgtt cgctccaagc tgggctgtgt gcacgaaccc   4680
cccgttcagc ccgaccgctg cgccttatcc ggtaactatc gtcttgagtc caacccggta   4740
agacacgact tatcgccact ggcagcagcc actggtaaca ggattagcag agcgaggtat   4800
gtaggcggtg ctacagagtt cttgaagtgg tggcctaact acggctacac tagaagaaca   4860
gtatttggta tctgcgctct gctgaagcca gttaccttcg gaaaaagagt tggtagctct   4920
tgatccggca aacaaaccac cgctggtagc ggtggttttt ttgtttgcaa gcagcagatt   4980
acgcgcagaa aaaaaggatc tcaagaagat cctttgatct tttctacggg gtctgacgct   5040
cagtggaacg aaaactcacg ttaagggatt ttggtcatga gattatcaaa aaggatcttc   5100
acctagatcc ttttaaatta aaaatgaagt tttaaatcaa tctaaagtat atatgagtaa   5160
acttggtctg acagttacca atgcttaatc agtgaggcac ctatctcagc gatctgtcta   5220
tttcgttcat ccatagttgc ctgactcccc gtcgtgtaga taactacgat acgggagggc   5280
ttaccatctg gccccagtgc tgcaatgata ccgcgagacc cacgctcacc ggctccagat   5340
ttatcagcaa taaaccagcc agccggaagg gccgagcgca gaagtggtcc tgcaacttta   5400
tccgcctcca tccagtctat taattgttgc cgggaagcta gagtaagtag ttcgccagtt   5460
aatagtttgc gcaacgttgt tgccattgct acaggcatcg tggtgtcacg ctcgtcgttt   5520
ggtatggctt cattcagctc cggttcccaa cgatcaaggc gagttacatg atcccccatg   5580
ttgtgcaaaa aagcggttag ctccttcggt cctccgatcg ttgtcagaag taagttggcc   5640
gcagtgttat cactcatggt tatggcagca ctgcataatt ctcttactgt catgccatcc   5700
gtaagatgct tttctgtgac tggtgagtac tcaaccaagt cattctgaga atagtgtatg   5760
cggcgaccga gttgctcttg cccggcgtca atacgggata ataccgcgcc acatagcaga   5820
actttaaaag tgctcatcat tggaaaacgt tcttcggggc gaaaactctc aaggatctta   5880
ccgctgttga tccagttcga tgtaacccac tcgtgcac ccaactgatc ttcagcatct   5940
tttactttca ccagcgtttc tgggtgagca aaaacaggaa ggcaaaatgc cgcaaaaaag   6000
ggaataaggg cgacacggaa atgttgaata ctcatactct tcctttttca atattattga   6060
agcatttatc agggttattg tctcatgagc ggatacatat ttgaatgtat ttagaaaaat   6120
aaacaaatag gggttccgcg cacatttccc cgaaaagtgc cacctgatgc ggtgtgaaat   6180
```

-continued

```
accgcacaga tgcgtaagga gaaaataccg catcaggaaa ttgtaagcgt taatattttg    6240
ttaaaattcg cgttaaattt ttgttaaatc agctcatttt ttaaccaata ggccgaaatc    6300
ggcaaaatcc cttataaatc aaaagaatag accgagatag ggttgagtgt tgttccagtt    6360
tggaacaaga gtccactatt aaagaacgtg gactccaacg tcaaagggcg aaaaaccgtc    6420
tatcagggcg atggcccact acgtgaacca tcaccctaat caagtttttt ggggtcgagg    6480
tgccgtaaag cactaaatcg gaaccctaaa gggagccccc gatttagagc ttgacgggga    6540
aagccggcga acgtggcgag aaaggaaggg aagaaagcga aaggagcggg cgctagggcg    6600
ctggcaagtg tagcggtcac gctgcgcgta accaccacac ccgccgcgct taatgcgccg    6660
ctacagggcg cgtccattcg ccattcaggc tgcgcaactg ttgggaaggg cgatcggtgc    6720
gggcctcttc gctattacgc cagctggcga aggggggatg tgctgcaagg cgattaagtt    6780
gggtaacgcc agggttttcc cagtcacgac gttgtaaaac gacggccagt gaattgtaat    6840
acgactcact atagggcgaa ttgggcccga cgtcgcatgc tcccggccgc catggccgcg    6900
ggatt                                                                6905
```

<210> SEQ ID NO 14
<211> LENGTH: 11320
<212> TYPE: DNA
<213> ORGANISM: Artificial Sequence
<220> FEATURE:
<223> OTHER INFORMATION: Plasmid Sequence

<400> SEQUENCE: 14

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacg ccagtgaatt ggagatcggt acttcgcgaa     420
tgcgtcgaga tgagctctaa tacgactcac tatagggact taagtgtgat ataaatatat     480
atcatacata ctagccttgt gctagatttc caacttaaca aaacggactt aaataccta     540 agttggtccc tataggtgtt ccattgcagt gcactttagt gccctggatg gcacctggcc     600
acctgtcagg ttttttgttat taaaataata ttgttgctgg tatcactgct tgttttgccg     660
tgtctcactt tatacatccg ttgcttgggc tacctagtat ccagcgtcct actggcgttg     720
tggtcggttc gagtgcgaag aacctctggt tcatctagcg gtacgcgggt gtgtggaagt     780
agcgcttcag acgtaccggt tctgttgcgt gaaatacggg gtcacctccc cccacatacc     840
tctaagggct tttgagccta gcgttgggct acgttctcgc acaaggtcgg ctatacggcg     900
tttgtagggg gtagtgccaa acaacccctg aggtgacagg ttctggtggt gtttcgaaaa     960
caacaatgtg tgtgccgcat aatatgcgag taatgcattt tggagcagga agtgacaaag    1020
gagtggcccc aggtagcgct gttcttaggc agtggcttcc cgaaggtaca ctccttgtcg    1080
ataatgatat tgtagattat gtatctgatg cacatgtctc tgtgctttca gattgcaata    1140
aatgtaaaac agagcacaag tttgatcttg tgatatctga tatgtataca gataatgatt    1200
caaagagaaa gcatgaaggc gttgtagcca ataacggcaa tgatgacgtc ttcatatacc    1260
```

-continued

```
tttcaaactt tcttcgtaac aatttagctc tgggaggcag ttttgccgta aaagtaacag       1320
agacaagttg gcatgagagt ttatatgaca ttgcacagga ttgtgcatgg tggacaatgt       1380
tttgtacagc agtgaatgct tcttcgtcag aagcattctt gattggtgtt aattatttgg       1440
gtgcaagtga aaaggttaga gttagtggta aaaccctgca cgcaaattat atattttgga       1500
ggaattgtaa ttatttacaa acttcagcct atagtatatt tgacgttgct aagtttgatt       1560
tgaaattaaa agcaacgcca gttgtgaatt tgaaaactga acaaaagaca gacttagtct       1620
ttaatttaat taagtgtggt aagttactgg taagagatgt tggacaaacc gcttttacta       1680
gtgactcttt ggtatgcact atgtagtgct ttgctctatg ataataatac ttacgtttac       1740
tactaccaaa gtgcctttag gcctggtcca ggttggcacc tatatggggg tgcttatgca       1800
gtagataggg tttttaatga aaccaacaat gcaggcagtg catctgattg cactgctggt       1860 acttttatg aaagccataa tatttctgct tcttctgtag ccatgacagt accacataat       1920
ggtatgtctt ggtcagcttc acaattttgt acagctcatt gtaacttctc agactttaca       1980
gtgttcgtta cgcattgttt taaaaatcaa ctcggtagtt gtcccttgac aggtatgatt       2040
cctcagaatc atattcgtat ttctgctatg agagatggag ttttgtttta taacttaaca       2100
gttagcgtat ctaaataccc tagatttaaa tcgcttcaat gtgttagcaa ttctacatct       2160
gtctatgtaa atggtgacct tgtttttcact tctaatgaaa cttcttacgt tacgggtgca       2220
ggcgtttatt ttaaaagtgg tgggcctgta acttataaag ttatgaaaga agttaaagcc       2280
ctagcctact ttattaatgg taccgcacaa gaggttattt tatgtgataa ctcacctaga       2340
ggtttgcttg catgtcagta taacactggt aattttttcag atggattcta cccttttact       2400
aatcattctt tagttaagga taggtttatt gtatatcgag aaaagtagcac taacactact       2460 ttaaagttaa ctaatttcag ttttactaat gtaagtaatg cttctcctaa ttcaggtggc       2520
gttgatactt tccaattata tcaaacaagt actgctcagg atggttatta taattttaat       2580
ttatcatttc tgagtagttt tgtgtataaa ccatctgatt ttatgtatgg gtcataccac       2640
ccacattgta agtttagacc agagaatatt aataatggct tatggtttaa ttcattatct       2700
gtgtcactta cttacggacc cattcaaggt ggttgtaagc aatctgtttt tagtaataga       2760
gcaacttgtt gctatgctta ttcttatcaa gggcctagta gatgtaaggg tgtttataga       2820
ggggagctaa cgcaatactt tgaatgtgga cttctagttt acgtaactaa gagtgatggc       2880
tctcgtatac aaactagaag tgaaccactg gtgttaactc aatataatta taacaacatt       2940
actttaaata gtgtgttga gtataatata tatggtaggg ttggtcaagg ttttattact       3000
aatgtaactg aagcaactgc taattatagt tatctagcag atggtggttt agctattttta       3060 gatacctcag gagccataga catatttgtt gttcaaggtg catatggtct taattattat       3120
aaggttaatc cctgtgaaga tgttaaccaa cagtttgtag tgtctggtgg caacttagtt       3180
ggcattctta catctcataa tgaaacaggt tctgaatcta ttgagaacca gttttacatc       3240
aaactcacta acggaacacg tcgctctaga cgttctgtta ctgggaatgt tacaaattgc       3300
ccttatgtta gttatggcaa gttttgtata aaaccagatg gttctttatc tataatagta       3360
ccacaagaat tagaacagtt tgtggcgcct ttattcaatg ttactgagca tgtgctcata       3420
cctgatagtt ttaattaac tgtcacagat gagtacatac aaactcgtat ggataaggtt       3480
caaattattt gccttcagta tgtttgtggt aattctattg aatgcagaaa gttgtttcag       3540
cagtatggac ctgtttgtga taatatattg tctgttgtaa atggtgtagg tcaaagagag       3600
gatatggaac ttttaagttt ctattcttct actaaaccta gtggttacaa tacaccaatt       3660
```

-continued

```
tttaataatg ttagcactgg tgactttaat atttcgctcc tactaacacc acctaatagt   3720
cctactgggc gctcttttat tgaagatctt ctctttacaa gtgtagaatc tgttggatta   3780
ccaactgatg aagagtataa aaagtgtaca gcaggacctt taggttttgt taaagacctt   3840
gtttgtgcta gagagtataa tggtttgctc gttctgcctc ctattattac tgcggaaatg   3900
caaaccatgt atactagttc tttagtagcc tctatggctt taggtggcat tactgcagct   3960
ggtgctatac cttttgctac acaactgcag gccagaatta accatttggg tattactaat   4020
tctcttttgt tgaaaaacca agaaaaaatt gctgcttcct ttaataaggc catcggtcat   4080
atgcaggaag ggtttaaaag tacttctcta gcattacaac agattcaaga tgttgttaat   4140
aaacagagtt ctattcttac agagactatg caatcactta ataaaaattt tggtgctatt   4200
tcctctgtaa ttcaagacat ttaccagcaa ctagatgcta ttcaggcaga tgctcatgtt   4260
gatcgtctta ttacaggtag actctcttca ctatctgttt tagcttctgc taaacaggca   4320
gagtatcata gagtgtcaca acagcgtgag ttggccactc agaaaattaa tgagtgtgtt   4380
aagtctcagt ctaataggta ttcattttgt ggtaatggta gacatgttct aaccatacca   4440
cagaatgcac ccaatggcat agtgtttata cactttacat acactccaga gagttttgtt   4500
aatgttacgg caatagtagg gtttttgcgta aacccagcta atgctagtca ttatgcaata   4560
gtgcctgtta atggcagggg tgtttttata gaagttaatg gtagttacta tatcactgct   4620
cgtgatatgt atatgccaag agatattact gcaggagaca tagtcacttt gacttcttgt   4680
caagcaaact atgttaatgt aaataaaacc gtcattaaca cttttgtgga agatgacgat   4740
tttgattttt atgatgaatt gtcaaaatgg tggaatgata ctaagcatga gctaccagat   4800
tttgatgaat tcaattatac cgttccagtt ttaaatatta gtaatgaaat tgacagaatt   4860
caacaggtta ttcagggatt aaatgattcc ctaatagacc ttgaaacact ctcaattctc   4920
aaaacttata ttaaatggcc ttggtatgtg tggcttgcca ttgcattcct taccattatt   4980
tttattctgg tactttgttg gatattttc atgaccggtt gttgcggttg ttgttgtgga   5040
tgctttggta tcataccgtt aatgagtaag tgtggtaaga aatcttctta ctacacgact   5100
tttgataatg atgtggtaac ttaacaatac agacctaaaa agtctgttta atgattaaaa   5160
gtcccacatc ttttctaata ttattaattc ttctttggtg taaacttgca ttaagttgtt   5220
ttaaagagtg tgttataaca ctccagcaac tagtacaaat tttactccaa attattaata   5280
gtaacttaca atctagactt ctgctttggc acagtctaga ctaatgttag attttgaagc   5340
aattattgaa actggtcagc aaataactca acaaattagt ttctatttac agcatatttc   5400
aagggtgcta agtactgaat tatttgaccc ctttgaagtt tgtgtttaca gaggaggtaa   5460
ttgttgggag ttagagtcag ctgacgagtt ttcaggtgat gacgaatata ttgagtagat   5520
cgctcgagga gaacggaagt tttctaacag cggtttacgt gtttttagga tttttagcac   5580
tttatctact aggtagagcg cttcaagctt ttgtacaagc ggctgacgct tgttgtcttt   5640
tttggtatac atgggtagta gttcctggag ccaagggcac agcctttgtt tataatcata   5700
catatggtaa aaaacttaac aaaccggagt tagaaacggt tattgttaac gaatttccaa   5760
aaaacggttg gaaatatgga aataccatca aattgtactc ttggtactga acaagcagtt   5820 cagctttttta aggaatataa tctgtttgta actgcattcc tgttgttttt aaccatacta   5880
cttcagtatg gatacgcaac taggagcaag gttatttaca tactgaaaat gatagtgtta   5940
tggtgctttt ggcccccttaa cattgcagta ggtgtaatct catgtatata cccaccaaac   6000
```

-continued

```
acaggaggtc ttgtcgcagc gataattctt acagtgtttg cgtgtctttc ttttataggt   6060
tattggatcc agagtattag acttttaag cggtgcaggt catggtggtc atttaacccc    6120
gaatctaatg ccgtaggttc aatactccta actaatggtc aacaatgtaa ttttgctata   6180
gagagtgtgc cgatggtgct ttctcctatt ataaagaatg gtgctcttta ttgcgagggt   6240
cagtggcttg ctaaatgtga accagaccac ttgcctagag atatatttgt atgcacaccg   6300
gatagacgta atatctatcg tatggtgcaa aaatatactg gtgaccaaag cggaagtaag   6360
aaaaggtttg ccacatttgt ctatgcaaag cagtcagtag atactggcga gctagaaagt   6420
gtgtcagcag taggaggtag tctttacaca taaatgtgtg tgtgtagaga gtatttaaaa   6480
ttattctttg acagtgcctc cgttttaaga gcgcggaaga gtattatttt tgaggatatt   6540
aatataaatc ctctttgttt catactctcc tttcaggagt tattatttaa aaaacagttt   6600
ttccactctt ttgtgccaaa aacaattgtt gttaatggtg taacctttca ggtagacaat   6660
ggaaaagtct actacgaagg aagaccaatt ttccaaaaag gttgttgtag tttgtggtcc   6720
aattataaga aagattagaa taattaaacc acctacaaca cttattttta caaatggcgt   6780
tttaggttac aaacgcttaa caaatacgga tgatgaaatg gctgactagt tttggaagag   6840
ctttcatctc ctgttataaa tccctattac taactcaatt aagagtatta gataggttaa   6900
ttttagatca cggacccaag cgcacattaa cgtgtgctag gcgagtgctt ttagttcaat   6960
tagatttagt ttataggttg gcttatacgc ccacccaatc gctggtatga ataatagtaa   7020
agataatcct tttcgcggag caatagcaag aaaagcgcga atttatctga gaggaggatt   7080
agattgtgtt tactttctta acaaagcagg acaagcagag ccttgtcccg cgtgtacctc   7140
cctagtattc caagggaaaa cttgtgagga acactattat aataacaatc ttttgtcatg   7200
gcaagcggta aggcaactgg aaagacagac gccccagcgc cagtcatcaa actaggagga   7260
ccaaagccac ctaaagttgg ttcttctgga aatgcatcat ggtttcaacc gataaaggcc   7320
aagaagctaa attcacctgt gcctaaattt gacggtagtg gtgttcctga aaatgaaaat   7380
ctcaagtcaa gccagcaaca tggatactgg agacgccaac acaggtttaa gcctggcaaa   7440
ggtggaagaa aaccagtccc tgatgcttgg tactttact acactggaac aggaccggcc    7500
gccgacctga attggggtga aactcaagat ggtatagtgt gggttgctgc aaagggtgct   7560
gatactaaat ctagatcaaa ccagggtaca agggatcctg ataagtttga ccaataccca   7620
ctacgattct cagatggagg accggatggt aatttccgtt gggacttcat accaataaat   7680
cgtggtagga gtgggagatc aacagcagct tcatcagcag catctagtag agcaccatct   7740
cgtgaggggt cacgtggacg tagaagcgga gttgaagatg atcttatagc tcgcgcagca   7800
aagattatac aggaccagca aaagaagggt gcgcgcatta ccaaggctaa ggctgatgaa   7860
atggctcatc gccgctattg caagcgcact atcccacctg gttataaggt tgagcaagta   7920
tttggtcccc gtactaaagg taaggaagga aattttggtg atgacaagat gaatgaggaa   7980
ggtgttaagg atgggcgtgt tacggcaatg ctcaacctag tccctagcag tcatgcttgt   8040
ctttttggaa gtagggtgac gcccaaactg cagccagatg gtcttcacct gagatttgaa   8100
tttactactg tggtgtcacg tgatgatccg cagtttgata attatgtgaa aatttgtgat   8160
cagtgtgtcg atggtgtagg gacgcgtcca aaggacgatg aatcgagacc aaagtcacgc   8220
ccaaattcaa gacctgcaac tagaggaaat tctccagcgc cgagacaaca gcgcccaaag   8280
aaggagaaaa agcccaagaa gcaggatgat gaagtagata aggcattgac ctcagatgag   8340
gagaggaaca atgcacagct ggaatttgat gatgaaccca aggtgattaa ctgggggggac   8400
```

```
tctgcactag gtgaaaatga actttgatta acataatgga cttgctgcat ttgctgtcac    8460
attttgttaa atattatttt tgtgtttac tatcaattat tacaggtatt gattgtgatt     8520
atgttcaata cttaagcttc ttctggttgc tttttgcttg ttgtattgtt gctgtgcttt    8580
ttattattgt gattctcatt agtttgcttt atcgtagaaa ttcaatagta agagttaagg    8640
aagataggca tgtagcttag cacctacatg tctatcgcca gggaaatgtc taatctgtct    8700
acttagtagc ctggaaacga acggtagacc cttagatttt aatttagttt aatttttagt    8760
ttagtttaag ttagtttaga gtaggtataa agatgccagt gccggggcca cgcgtagtac    8820
gaccgagggt acagcactag gacgcccact aggggaagag ctaaattta gtttaagtta     8880 agtttaattg gctaaatata gttaaaattt ataggctagt atagagttag agcaaaaaaa    8940
aaaaaaaaaa aaaaaaaaaa aaaaaaaaaa aaaaaaaaaa aaaaaaaaaa aaaaaaaaaa    9000
aaaaaaaaaa aaaaaaaaaa aaaaaaaaaa aaagcggccg catcggatgc cgggaccgac    9060
gagtgcagag gcgtgcaagc gagcttggcg taatcatggt catagctgtt tcctgtgtga    9120
aattgttatc cgctcacaat tccacacaac atacgagccg gaagcataaa gtgtaaagcc    9180
tggggtgcct aatgagtgag ctaactcaca ttaattgcgt tgcgctcact gcccgctttc    9240
cagtcgggaa acctgtcgtg ccagctgcat taatgaatcg gccaacgcgc ggggagaggc    9300
ggtttgcgta ttgggcgctc ttccgcttcc tcgctcactg actcgctgcg ctcggtcgtt    9360
cggctgcggc gagcggtatc agctcactca aaggcggtaa tacggttatc cacagaatca    9420
ggggataacg caggaaagaa catgtgagca aaaggccagc aaaaggccag gaaccgtaaa    9480
aaggccgcgt tgctggcgtt tttccatagg ctccgccccc ctgacgagca tcacaaaaat    9540
cgacgctcaa gtcagaggtg gcgaaacccg acaggactat aaagatacca ggcgtttccc    9600
cctggaagct ccctcgtgcg ctctcctgtt ccgaccctgc cgcttaccgg atacctgtcc    9660
gcctttctcc cttcgggaag cgtggcgctt tctcatagct cacgctgtag gtatctcagt    9720
tcggtgtagg tcgttcgctc caagctgggc tgtgtgcacg aaccccccgt tcagcccgac    9780
cgctgcgcct tatccggtaa ctatcgtctt gagtccaacc cggtaagaca cgacttatcg    9840
ccactggcag cagccactgg taacaggatt agcagagcga ggtatgtagg cggtgctaca    9900
gagttcttga agtggtggcc taactacggc tacactagaa gaacagtatt tggtatctgc    9960
gctctgctga agccagttac cttcggaaaa agagttggta gctcttgatc cggcaaacaa    10020
accaccgctg gtagcggtgg tttttttgtt tgcaagcagc agattacgcg cagaaaaaaa    10080
ggatctcaag aagatccttt gatcttttct acggggtctg acgctcagtg gaacgaaaac    10140
tcacgttaag ggattttggt catgagatta tcaaaaagga tcttcaccta gatccttta     10200 aattaaaaat gaagttttaa atcaatctaa agtatatatg agtaaacttg gtctgacagt    10260
taccaatgct taatcagtga ggcacctatc tcagcgatct gtctatttcg ttcatccata    10320
gttgcctgac tccccgtcgt gtagataact acgatacggg agggcttacc atctggcccc    10380
agtgctgcaa tgataccgcg agacccacgc tcaccggctc cagatttatc agcaataaac    10440
cagccagccg gaagggccga gcgcagaagt ggtcctgcaa ctttatccgc ctccatccag    10500
tctattaatt gttgccggga agctagagta agtagttcgc cagttaatag tttgcgcaac    10560
gttgttgcca ttgctacagg catcgtggtg tcacgctcgt cgtttggtat ggcttcattc    10620
agctccggtt cccaacgatc aaggcgagtt acatgatccc ccatgttgtg caaaaaagcg    10680
gttagctcct tcggtcctcc gatcgttgtc agaagtaagt tggccgcagt gttatcactc    10740
```

-continued

```
atggttatgg cagcactgca taattctctt actgtcatgc catccgtaag atgctttct    10800 gtgactggtg agtactcaac caagtcattc tgagaatagt gtatgcggcg accgagttgc    10860
tcttgcccgg cgtcaatacg ggataatacc gcgccacata gcagaacttt aaaagtgctc    10920
atcattggaa aacgttcttc ggggcgaaaa ctctcaagga tcttaccgct gttgagatcc    10980
agttcgatgt aacccactcg tgcacccaac tgatcttcag catcttttac tttcaccagc    11040
gtttctgggt gagcaaaaac aggaaggcaa aatgccgcaa aaaagggaat aagggcgaca    11100
cggaaatgtt gaatactcat actcttcctt tttcaatatt attgaagcat ttatcagggt    11160
tattgtctca tgagcggata catatttgaa tgtatttaga aaaataaaca aataggggtt    11220
ccgcgcacat ttccccgaaa agtgccacct gacgtctaag aaaccattat tatcatgaca    11280
ttaacctata aaaataggcg tatcacgagg ccctttcgtc                          11320
```

<210> SEQ ID NO 15
<211> LENGTH: 6905
<212> TYPE: DNA
<213> ORGANISM: Artificial Sequence
<220> FEATURE:
<223> OTHER INFORMATION: Plasmid Sequence

<400> SEQUENCE: 15

```
ttaattaagt gtggtaagtt actggtaaga gatgttggac aaaccgcttt tactagtgac       60
tctttggtat gcactatgta gtgctttgct ctatgtaaat aatacttacg tttactacta      120
ccaaagtgcc tttaggcctg gtccaggttg gcacctatat gggggtgctt atgcagtaga      180
tagggttttt aatgaaacca acaatgcagg cagtgcatct gattgcactg ctggtacttt      240
ttatgaaagc cataatattt ctgcttcttc tgtagccatg acagtaccac ataatggtat      300
gtcttggtca gcttcacaat tttgtacagc tcattgtaac ttctcagact ttacagtgtt      360
cgttacgcat tgtttttaaaa atcaactcgg tagttgtccc ttgacaggta tgattcctca     420
gaatcatatt cgtatttctg ctatgagaga tggagttttg ttttataact aacagttag       480 cgtatctaaa taccctagat ttaaatcgct tcaatgtgtt agcaattcta catctgtcta      540
tgtaaatggt gaccttgttt tcacttctaa tgaaacttct tacgttacgg gtgcaggcgt      600
ttattttaaa agtggtgggc ctgtaactta taaagttatg aaagaagtta aagccctagc      660
ctactttatt aatggtaccg cacaagaggt tattttatgt gataactcac ctagaggttt      720
gcttgcatgt cagtataaca ctggtaattt ttcagatgga ttctacccctt ttactaatca     780 ttctttagtt aaggataggt ttattgtata tcgagaaagt agcactaaca ctactttaaa      840
gttaactaat ttcagtttta ctaatgtaag taatgcttct cctaattcag gtggcgttga      900
tactttccaa ttatatcaaa caagtactgc tcaggatggt tattataatt ttaatttatc      960
atttctgagt agttttgtgt ataaaccatc tgattttatg tatgggtcat accacccaca     1020
ttgtaagttt agaccagaga atattaataa tggcttatgg tttaattcat tatctgtgtc     1080
acttacttac ggacccattc aaggtggttg taagcaatct gtttttagta atagagcaac     1140
ttgttgctat gcttattctt atcaagggcc tagtagatgt aagggtgttt atagagggga     1200
gctaacgcaa tactttgaat gtggacttct agtttacgta actaagagtg atggctctcg     1260
tatacaaact agaagtgaac cactggtgtt aactcaatat aattataaca acattacttt     1320
aaataagtgt gttgagtata atatatatgg tagggttggt caaggtttta ttactaatgt     1380
aactgaagca actgctaatt atagttatct agcagatggg ggtttagcta ttttagatac     1440
ctcaggagcc atagacatat ttgttgttca aggtgcatat ggtcttaatt attataaggt     1500
```

-continued

```
taatccctgt gaagatgtta accaacagtt tgtagtgtct ggtggcaact tagttggcat    1560
tcttacatct cataatgaaa caggttctga atctattgag aaccagtttt acatcaaact    1620
cactaacgga acacgtcgct ctagacgttc tgttactggg aatgttacaa attgcccta    1680 tgttagttat ggcaagtttt gtataaaacc agatggttct ttatctataa tagtaccaca    1740
agaattagaa cagtttgtgg cgcctttatt caatgttact gagcatgtgc tcatacctga    1800
tagttttaat ttaactgtca cagatgagta catacaaact cgtatggata aggttcaaat    1860
tatttgcctt cagtatgttt gtggtaattc tattgaatgc agaaagttgt ttcagcagta    1920
tggacctgtt tgtgataata tattgtctgt tgtaaatggt gtaggtcaaa gagaggatat    1980
ggaactttta agtttctatt cttctactaa acctagtggt tacaatacac caattttaa    2040 taatgttagc actggtgact ttaatatttc gctcctacta acaccaccta atagtcctac    2100
tgggcgctct tttattgaag atcttctctt tacaagtgta gaatctgttg gattaccaac    2160
tgatgaagag tataaaaagt gtacagcagg acctttaggt tttgttaaag accttgtttg    2220
tgctagagag tataatggtt tgctcgttct gcctcctatt attactgcgg aaatgcaaac    2280
catgtatact agttctttag tagcctctat ggctttaggt ggcattactg cagctggtgc    2340
tatacctttt gctacacaac tgcaggccag aattaaccat ttgggtatta ctaattctct    2400
tttgttgaaa aaccaagaaa aaattgctgc ttcctttaat aaggccatcg gtcatatgca    2460
ggaagggttt aaaagtactt ctctagcatt acaacagatt caagatgttg ttaataaaca    2520
gagttctatt cttacagaga ctatgcaatc acttaataaa aattttggtg ctatttcctc    2580
tgtaattcaa gacatttacc agcaactaga tgctattcag gcagatgctc atgttgatcg    2640
tcttattaca ggtagactct cttcactatc tgtttttagct tctgctaaac aggcagagta    2700
tcatagagtg tcacaacagc gtgagttggc cactcagaaa attaatgagt gtgttaagtc    2760
tcagtctaat aggtattcat tttgtggtaa tggtagacat gttctaacca taccacagaa    2820
tgcacccaat ggcatagtgt ttatacactt tacatacact ccagagagtt ttgttaatgt    2880
tacggcaata gtagggtttt gcgtaaaccc agctaatgct agtcattatg caatagtgcc    2940
tgttaatggc aggggtgttt ttatagaagt taatggtagt tactatatca ctgctcgtga    3000
tatgtatatg ccaagagata ttactgcagg agacatagtc actttgactt cttgtcaagc    3060
aaactatgtt aatgtaaata aaaccgtcat taacactttt gtggaagatg acgattttga    3120
tttttatgat gaattgtcaa aatggtggaa tgatactaag catgagctac cagatttga    3180 tgaattcaat tataccgttc cagttttaaa tattagtaat gaaattgaca gaattcaaca    3240
ggttattcag ggattaaatg attccctaat agaccttgaa acactctcaa ttctcaaaac    3300
ttatattaaa tggccttggt atgtgtggct tgccattgca ttccttacca ttatttttat    3360
tctggtactt tgttggatat ttttcatgac cggttgttgc ggttgttgtt gtggatgctt    3420
tggtatcata ccgttaatga gtaagtgtgg taagaaatct tcttactaca cgactttga    3480 taatgatgtg gtaacttaac aatacagacc taaaaagtct gtttaatgat taaaagtccc    3540 acatctttc taatattatt aattcttctt tggtgtaaac ttgcattaag ttgtttaaa    3600 gagtgtgtta taacactcca gcaactagta caaatttac tccaaattat taatagtaac    3660
ttacaatcta gacttctgct ttggcacagt ctagactaat gttagatttt gaagcaatta    3720
ttgaaactgg tcagcaaata actcaacaaa ttagtttcta tttacagcat atttcaaggg    3780
tgctaagtac tgaattattt gacccctttg aagtttgtgt ttacagagga ggtaattgtt    3840
```

-continued

```
gggagttaga gtcagctgac gagttttcag gtgatgacga atatattgag tagatcgctc      3900
gagaatcact agtgcggccg cctgcaggtc gaccatatgg gagagctccc aacgcgttgg      3960
atgcatagct tgagtattct atagtgtcac ctaaatagct tggcgtaatc atggtcatag      4020
ctgtttcctg tgtgaaattg ttatccgctc acaattccac acaacatacg agccggaagc      4080
ataaagtgta aagcctgggg tgcctaatga gtgagctaac tcacattaat tgcgttgcgc      4140
tcactgcccg ctttccagtc gggaaacctg tcgtgccagc tgcattaatg aatcggccaa      4200
cgcgcgggga gaggcggttt gcgtattggg cgctcttccg cttcctcgct cactgactcg      4260
ctgcgctcgg tcgttcggct gcggcgagcg gtatcagctc actcaaaggc ggtaatacgg      4320
ttatccacag aatcagggga taacgcagga aagaacatgt gagcaaaagg ccagcaaaag      4380
gccaggaacc gtaaaaaggc cgcgttgctg gcgtttttcc ataggctccg cccccctgac      4440
gagcatcaca aaaatcgacg ctcaagtcag aggtggcgaa acccgacagg actataaaga      4500
taccaggcgt ttccccctgg aagctccctc gtgcgctctc ctgttccgac cctgccgctt      4560
accggatacc tgtccgcctt tctcccttcg ggaagcgtgg cgctttctca tagctcacgc      4620
tgtaggtatc tcagttcggt gtaggtcgtt cgctccaagc tgggctgtgt gcacgaaccc      4680
cccgttcagc ccgaccgctg cgccttatcc ggtaactatc gtcttgagtc caacccggta      4740
agacacgact tatcgccact ggcagcagcc actggtaaca ggattagcag agcgaggtat      4800
gtaggcggtg ctacagagtt cttgaagtgg tggcctaact acggctacac tagaagaaca      4860
gtatttggta tctgcgctct gctgaagcca gttaccttcg gaaaaagagt tggtagctct      4920
tgatccggca aacaaaccac cgctggtagc ggtggttttt ttgtttgcaa gcagcagatt      4980
acgcgcagaa aaaaggatc tcaagaagat cctttgatct tttctacggg gtctgacgct      5040
cagtggaacg aaaactcacg ttaagggatt ttggtcatga gattatcaaa aaggatcttc      5100
acctagatcc ttttaaatta aaaatgaagt tttaaatcaa tctaaagtat atatgagtaa      5160
acttggtctg acagttacca atgcttaatc agtgaggcac ctatctcagc gatctgtcta      5220
tttcgttcat ccatagttgc ctgactcccc gtcgtgtaga taactacgat acgggagggc      5280
ttaccatctg gccccagtgc tgcaatgata ccgcgagacc cacgctcacc ggctccagat      5340
ttatcagcaa taaaccagcc agccggaagg gccgagcgca gaagtggtcc tgcaacttta      5400
tccgcctcca tccagtctat taattgttgc cgggaagcta gagtaagtag ttcgccagtt      5460
aatagtttgc gcaacgttgt tgccattgct acaggcatcg tggtgtcacg ctcgtcgttt      5520
ggtatggctt cattcagctc cggttcccaa cgatcaaggc gagttacatg atcccccatg      5580
ttgtgcaaaa aagcggttag ctccttcggt cctccgatcg ttgtcagaag taagttggcc      5640
gcagtgttat cactcatggt tatggcagca ctgcataatt ctcttactgt catgccatcc      5700
gtaagatgct tttctgtgac tggtgagtac tcaaccaagt cattctgaga atagtgtatg      5760
cggcgaccga gttgctcttg cccggcgtca atacgggata ataccgcgcc acatagcaga      5820
actttaaaag tgctcatcat tggaaaacgt tcttcgggc gaaaactctc aaggatctta      5880
ccgctgttga tccagttc gatgtaaccc actcgtgcac ccaactgatc ttcagcatct      5940
tttactttca ccagcgtttc tgggtgagca aaaacaggaa ggcaaaatgc cgcaaaaaag      6000
ggaataaggg cgacacggaa atgttgaata ctcatactct tccttttca atattattga      6060 agcatttatc agggttattg tctcatgagc ggatacatat ttgaatgtat ttagaaaaat      6120
aaacaaatag gggttccgcg cacatttccc cgaaaagtgc cacctgatgc ggtgtgaaat      6180
accgcacaga tgcgtaagga gaaaataccg catcaggaaa ttgtaagcgt taatattttg      6240
```

-continued

```
ttaaaattcg cgttaaattt ttgttaaatc agctcatttt ttaaccaata ggccgaaatc      6300
ggcaaaatcc cttataaatc aaaagaatag accgagatag ggttgagtgt tgttccagtt      6360
tggaacaaga gtccactatt aaagaacgtg gactccaacg tcaaagggcg aaaaaccgtc      6420
tatcagggcg atggcccact acgtgaacca tcaccctaat caagtttttt ggggtcgagg      6480
tgccgtaaag cactaaatcg gaaccctaaa gggagccccc gatttagagc ttgacgggga      6540
aagccggcga acgtggcgag aaaggaaggg aagaaagcga aaggagcggg cgctagggcg      6600
ctggcaagtg tagcggtcac gctgcgcgta accaccacac ccgccgcgct taatgcgccg      6660
ctacagggcg cgtccattcg ccattcaggc tgcgcaactg ttgggaaggg cgatcggtgc      6720
gggcctcttc gctattacgc cagctggcga aggggggatg tgctgcaagg cgattaagtt      6780
gggtaacgcc agggttttcc cagtcacgac gttgtaaaac gacggccagt gaattgtaat      6840
acgactcact atagggcgaa ttgggcccga cgtcgcatgc tcccggccgc catggccgcg      6900
ggatt                                                                  6905
```

```
<210> SEQ ID NO 16
<211> LENGTH: 47
<212> TYPE: DNA
<213> ORGANISM: Artificial Sequence
<220> FEATURE:
<223> OTHER INFORMATION: Primer Sequence

<400> SEQUENCE: 16
ttaattaagt gtggtaagtt gcttgtaaga gatgttggta acacctc                     47

<210> SEQ ID NO 17
<211> LENGTH: 47
<212> TYPE: DNA
<213> ORGANISM: Artificial Sequence
<220> FEATURE:
<223> OTHER INFORMATION: Primer Sequence

<400> SEQUENCE: 17
ctcgagcgac ttattcaata aattcatcat taaacagact ttttagg                     47

<210> SEQ ID NO 18
<211> LENGTH: 39
<212> TYPE: DNA
<213> ORGANISM: Artificial Sequence
<220> FEATURE:
<223> OTHER INFORMATION: Primer Sequence

<400> SEQUENCE: 18
ccatacaagc aaatgctcac gtggatcgtc ttataactg                              39

<210> SEQ ID NO 19
<211> LENGTH: 19
<212> TYPE: DNA
<213> ORGANISM: Artificial Sequence
<220> FEATURE:
<223> OTHER INFORMATION: Primer Sequence

<400> SEQUENCE: 19
tgctgcttcc tttaataag                                                    19

<210> SEQ ID NO 20
<211> LENGTH: 20
<212> TYPE: DNA
<213> ORGANISM: Artificial Sequence
<220> FEATURE:
```

<223> OTHER INFORMATION: Primer Sequence

<400> SEQUENCE: 20
aacactatac cattaggtgc                                                     20

<210> SEQ ID NO 21
<211> LENGTH: 52
<212> TYPE: DNA
<213> ORGANISM: Artificial Sequence
<220> FEATURE:
<223> OTHER INFORMATION: Primer Sequence

<400> SEQUENCE: 21
cagagcacaa gtttgatctt gtgatatctg atatgtatac agacaatgat tc               52

<210> SEQ ID NO 22
<211> LENGTH: 32
<212> TYPE: DNA
<213> ORGANISM: Artificial Sequence
<220> FEATURE:
<223> OTHER INFORMATION: Primer Sequence

<400> SEQUENCE: 22
gtgttaccaa catctcttac cagtaactta cc                                      32

<210> SEQ ID NO 23
<211> LENGTH: 35
<212> TYPE: DNA
<213> ORGANISM: Artificial Sequence
<220> FEATURE:
<223> OTHER INFORMATION: Primer Sequence

<400> SEQUENCE: 23
ttactggtaa gagatgttgg taacacctct tttac                                   35

<210> SEQ ID NO 24
<211> LENGTH: 35
<212> TYPE: DNA
<213> ORGANISM: Artificial Sequence
<220> FEATURE:
<223> OTHER INFORMATION: Primer Sequence

<400> SEQUENCE: 24
ggactttgga tcattaaaca gactttttag gtctg                                   35

<210> SEQ ID NO 25
<211> LENGTH: 32
<212> TYPE: DNA
<213> ORGANISM: Artificial Sequence
<220> FEATURE:
<223> OTHER INFORMATION: Primer Sequence

<400> SEQUENCE: 25
aaagtctgtt taatgatcca aagtcccact ag                                      32

<210> SEQ ID NO 26
<211> LENGTH: 48
<212> TYPE: DNA
<213> ORGANISM: Artificial Sequence
<220> FEATURE:
<223> OTHER INFORMATION: Primer Sequence

<400> SEQUENCE: 26
cttaactcct ggaattacta accacgtgta ccaaaataaa caacaagc                     48

-continued

```
<210> SEQ ID NO 27
<211> LENGTH: 20
<212> TYPE: DNA
<213> ORGANISM: Artificial Sequence
<220> FEATURE:
<223> OTHER INFORMATION: Primer Sequence

<400> SEQUENCE: 27
tgacttggtt tgaagatggc                                                          20

<210> SEQ ID NO 28
<211> LENGTH: 20
<212> TYPE: DNA
<213> ORGANISM: Artificial Sequence
<220> FEATURE:
<223> OTHER INFORMATION: Primer Sequence

<400> SEQUENCE: 28
ccccatgtaa atgccaacca                                                          20

<210> SEQ ID NO 29
<211> LENGTH: 39
<212> TYPE: DNA
<213> ORGANISM: Artificial Sequence
<220> FEATURE:
<223> OTHER INFORMATION: Primer Sequence

<400> SEQUENCE: 29
ctattcaggc agatgctcat gttgatcgtc ttattacag                                     39

<210> SEQ ID NO 30
<211> LENGTH: 20
<212> TYPE: DNA
<213> ORGANISM: Artificial Sequence
<220> FEATURE:
<223> OTHER INFORMATION: Primer Sequence

<400> SEQUENCE: 30
tcagcgtgga catgtggtta                                                          20

<210> SEQ ID NO 31
<211> LENGTH: 20
<212> TYPE: DNA
<213> ORGANISM: Artificial Sequence
<220> FEATURE:
<223> OTHER INFORMATION: Primer Sequence

<400> SEQUENCE: 31
ccccatatag gtgccaacct                                                          20
```